United States Patent
Upton et al.

(10) Patent No.: US 10,941,104 B2
(45) Date of Patent: Mar. 9, 2021

(54) BIOMASS-DERIVED POLYMERS AND COPOLYMERS INCORPORATING MONOLIGNOLS AND THEIR DERIVATIVES

(71) Applicant: The Regents of the University of California, Oakland, CA (US)

(72) Inventors: Brianna Marie Upton, Los Angeles, CA (US); Andrea Kasko, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 137 days.

(21) Appl. No.: 15/767,309

(22) PCT Filed: Oct. 14, 2016

(86) PCT No.: PCT/US2016/057212
§ 371 (c)(1),
(2) Date: Apr. 10, 2018

(87) PCT Pub. No.: WO2017/066699
PCT Pub. Date: Apr. 20, 2017

(65) Prior Publication Data
US 2019/0062258 A1    Feb. 28, 2019

Related U.S. Application Data

(60) Provisional application No. 62/242,789, filed on Oct. 16, 2015.

(51) Int. Cl.
*C07C 67/44* (2006.01)
*C08G 69/40* (2006.01)
(Continued)

(52) U.S. Cl.
CPC .......... *C07C 67/44* (2013.01); *C07C 29/149* (2013.01); *C07C 51/00* (2013.01); *C07C 51/09* (2013.01);
(Continued)

(58) Field of Classification Search
None
See application file for complete search history.

(56) References Cited

FOREIGN PATENT DOCUMENTS

| JP | 07-089901 | 4/1995 |
| WO | 2014/194055 | 12/2014 |

OTHER PUBLICATIONS

Ouimet et al (Biodegradable Ferulic Acid-Containing Poly(anhydride-ester): Degradation Products with Controlled Release and Sustained Antioxidant Activity, Biomacromolecules 2013, 14, 854-861). (Year: 2013).*

(Continued)

*Primary Examiner* — Rachel Kahn
(74) *Attorney, Agent, or Firm* — Gates & Cooper LLP

(57) ABSTRACT

The invention includes methods and materials for forming and manipulating aromatic-based polymers and copolymers using biomass compounds as starting materials. Embodiments of the invention can be used in processes designed to replace those used in the petro-chemical industry. Typical embodiments of the invention include methods and materials for forming and/or modifying compounds including dicarboxylic acid ester dimers, benzoxazines and dicarboxylic acid ether dimers. Embodiments of the invention further provide methods and materials for utilizing these compounds to form commercially desirable polymers having structures and physical properties akin to those found in polymers formed from petroleum products.

8 Claims, 36 Drawing Sheets

(51) Int. Cl.
*C07D 265/16* (2006.01)
*C07C 51/09* (2006.01)
*C08G 69/44* (2006.01)
*C08G 73/02* (2006.01)
*C07C 67/343* (2006.01)
*C07C 67/31* (2006.01)
*C07C 67/14* (2006.01)
*C07C 67/28* (2006.01)
*C07C 29/149* (2006.01)
*C07C 51/00* (2006.01)
*C07C 51/41* (2006.01)
*C07C 67/10* (2006.01)
*C08G 69/46* (2006.01)
*C08G 69/48* (2006.01)

(52) U.S. Cl.
CPC ............ *C07C 51/412* (2013.01); *C07C 67/10* (2013.01); *C07C 67/14* (2013.01); *C07C 67/28* (2013.01); *C07C 67/31* (2013.01); *C07C 67/343* (2013.01); *C07D 265/16* (2013.01); *C08G 69/40* (2013.01); *C08G 69/44* (2013.01); *C08G 69/46* (2013.01); *C08G 69/48* (2013.01); *C08G 73/0233* (2013.01)

(56) References Cited

OTHER PUBLICATIONS

Nagata et al (Synthesis and Characterization of Photocrosslinkable Biodegradable Polymers Derived from 4-Hydroxycinnamic Acid, Macromol. Biosci. 2003, 3, No. 8, pp. 412-419) (Year: 2003).*

Tararov et al (Facile Preparation and Purification of Mono tert-Butyl Malonate, Synthetic Communications, 36: 187-191, 2006) (Year: 2006).*

Braun et al (Polymer Synthesis: Theory and Practice, 4th Edition, Springer, 2005, pp. 64-65). (Year: 2005).*

Comi, M., et al, J. Polym. Sci., Part A: Polym. Chem. 2013, 51(22), 4894-903, "Renewable Benzoxazine Monomers from "Lignin-like" Naturally Occurring Phenolic Derivatives".

PCT International Search Report & Written Opinion dated Mar. 2, 2017 for PCT Application No. PCT/US2016/057212.

Ouimet, M. A. et al., "Biodegradable Coumaric Acid-Based Poly(anhydride-ester) Synthesis and Subsequent Controlled Release", Macromol. Rapid Commun., 2013 [Epub. Jul. 9, 2013], vol. 34, No. 15, pp. 1231-1236.

Park, K. H. et al., "Synthesis and Characterization of New Soluble Aromatic Polyamides from Diaminotetraphenylimidazolin-2-One and Various Aromatic Dicarboxylic-Acid Chlorides", Journal of Polymer Science Part A: Polymer Chemistry, 1995, vol. 33, No. 7, pp. 1031-1037.

Van, A. et al., "Use of renewable resource vanillin for the preparation of benzoxazine resin and reactive monomeric surfactant containing oxazine ring", Polymer, Mar. 24, 2014 [Epub. Feb. 1, 2014], vol. 55, No. 6, pp. 1443-1451.

Shabanian, M. et al., "Synthesis and characterization of new heat resistance and organosoluble poly(ether-amide)", Bull. Chem. Soc. Ethiop., 2013, vol. 27, No. 3, pp. 413-419.

Ouimet, M. A. et al., "Biodegradable Ferulic Acid-Containing Poly(anhydride-ester): Degradation Products with Controlled Release and Sustained Antioxidant Activity", Biomacromolecules, Mar. 11, 2013 [Epub. Jan. 17, 2013], vol. 14, No. 3. pp. 854-861.

* cited by examiner

Aliphatic polyamides

R= H, OCH₃

| R | n | $M_n$ | $M_w$ | PDI |
|---|---|-------|-------|------|
| H | 3 | 7,910 | 8,350 | 1.06 |
| OCH₃ | 2 | 24,750 | 33,520 | 1.31 |
| OCH₃ | 3 | 8,420 | 8,810 | 1.05 |
| OCH₃ | 4 | 19,260 | 20,570 | 1.08 |
| OCH₃ | 5 | 23,490 | 26,060 | 1.11 |

Aromatic polyamides
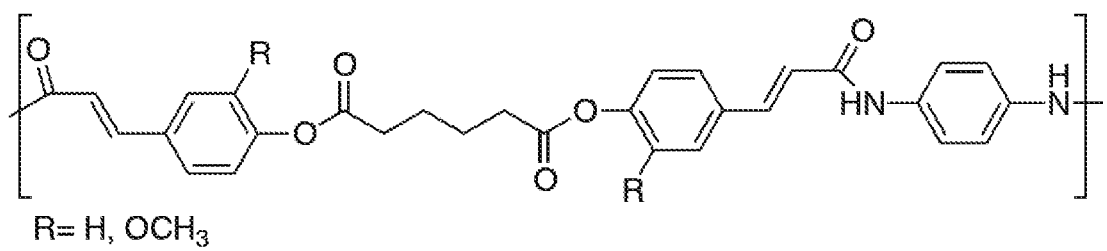
R= H, OCH₃
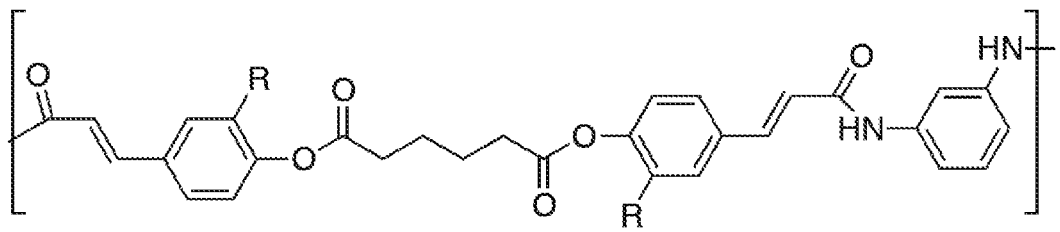
| R | *m or p* | $M_n$ | $M_w$ | PDI |
|---|---|---|---|---|
| OCH₃ | *para* | 38,480 | 50,040 | 1.30 |
| OCH₃ | *meta* | 11,760 | 19,950 | 1.19 |
FIG. 8

Thermal Stability of Aliphatic polyamides

| R | n | $T_{d10}$ | $T_{d25}$ | $T_{d50}$ |
|---|---|-----------|-----------|-----------|
| H | 3 | 280.4 | 349.9 | 442.1 |
| $OCH_3$ | 2 | | | |
| $OCH_3$ | 3 | 221.5 | 326.2 | 430.8 |
| $OCH_3$ | 4 | 415.3 | 478.4 | 566.9 |
| $OCH_3$ | 5 | 307.3 | 390.6 | 498.2 |

All temperatures given in °C. Thermogravimetric analysis was performed under oxygen, heating from 25 °C to 650 °C at a rate of 10 °C min$^{-1}$.

FIG. 9

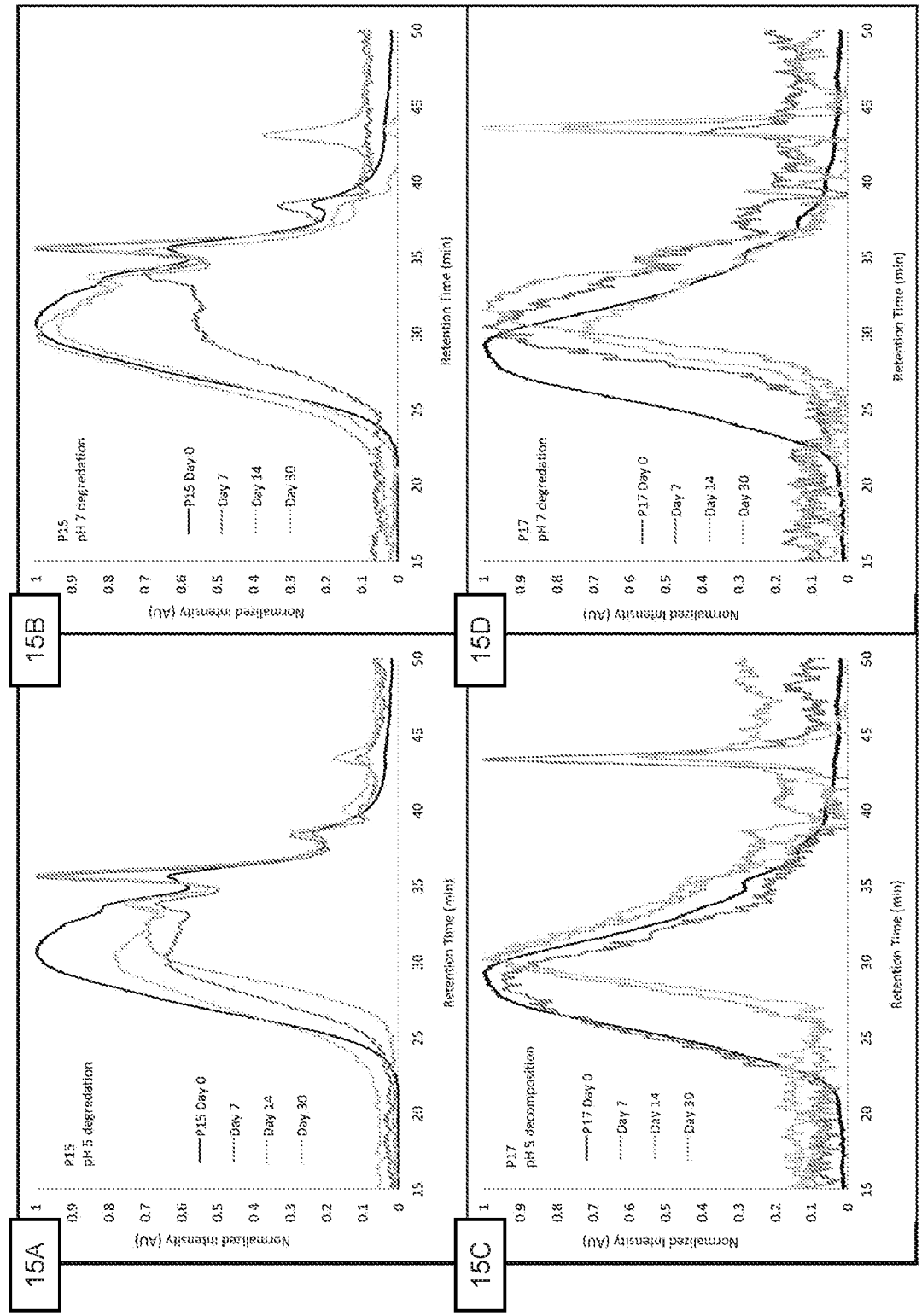
FIGS. 15A-D

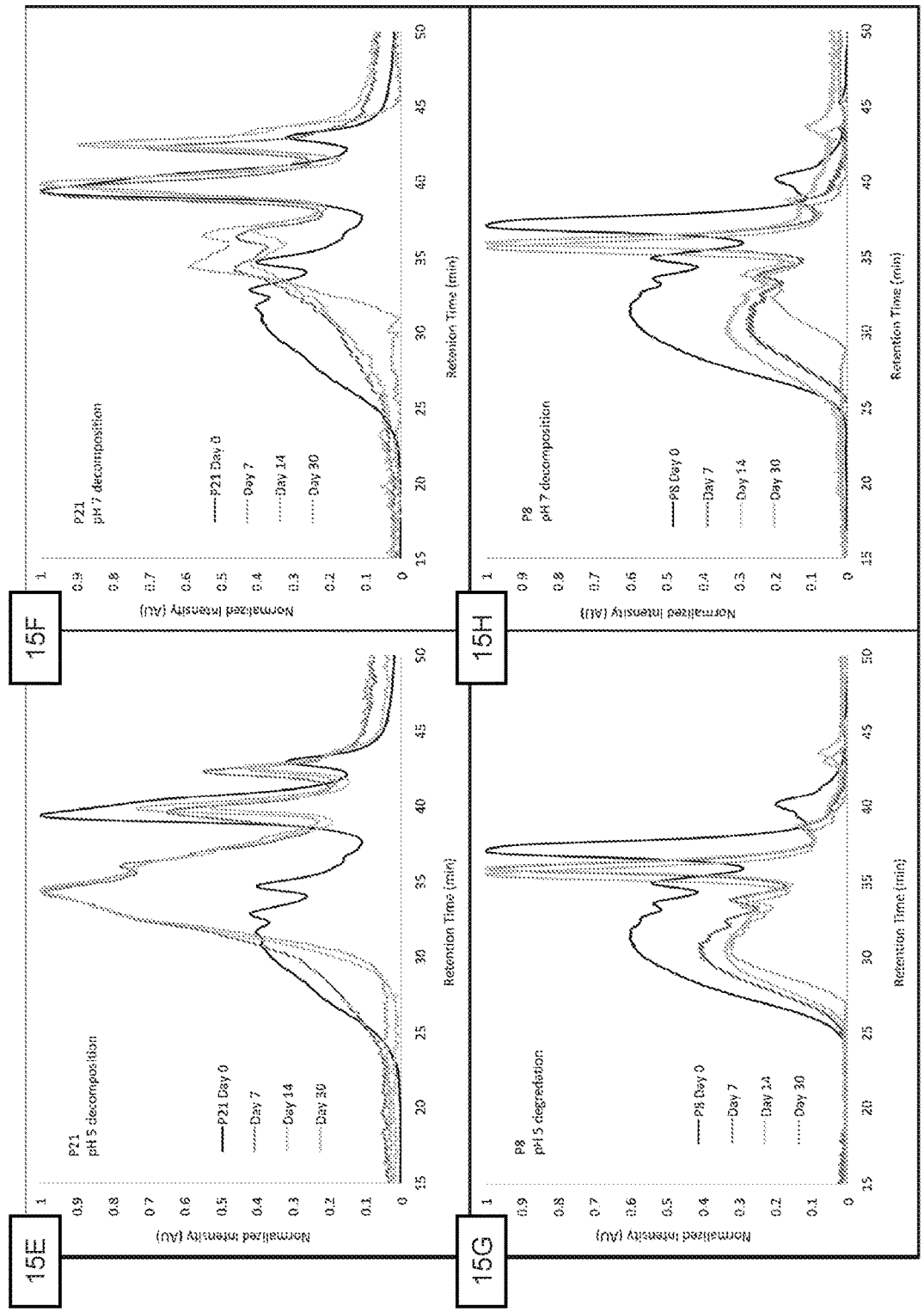
FIGS. 15E-H

BIOMASS-DERIVED POLYMERS AND COPOLYMERS INCORPORATING MONOLIGNOLS AND THEIR DERIVATIVES

CROSS REFERENCE TO RELATED APPLICATIONS

This application claims the benefit under 35 U.S.C. Section 119(e) of U.S. Provisional Patent Application Ser. No. 62/242,789, titled "BIOMASS-DERIVED POLYMERS AND COPOLYMERS INCORPORATING MONOLIGNOLS AND THEIR DERIVATIVES" filed Oct. 16, 2015, the contents of which are incorporated herein by reference.

TECHNICAL FIELD

The invention relates to methods and materials for making polymeric molecules, in particular, aromatic-based polymers and copolymers.

BACKGROUND OF THE INVENTION

Biomass-based polymeric materials have received a great deal of attention from the industrial sector in recent years in view of declining petroleum reserves. Researchers studying new green technologies have identified the targeted upgrading of biomass to commodity chemical or material products as a critical goal to offset an increasing dependence on petroleum worldwide [12]. Lignin is an abundant biological material found in biomass, particularly wood and bark. Due to its low cost, abundance, and aromatic structure, lignin offers great potential for use in polymeric products. Because of its abundance and accessibility, lignocellulosic biomass has been the key focus of environmentally-friendly alternatives to petroleum feedstocks [13].

As the second most abundant natural polymer after cellulose, lignin provides an ideal platform for the development of novel polymeric and composite materials. Lignin is abundant in industrial waste streams and easily isolated from plant materials through the industrial processing of biomass to create materials such as paper or ethanol. With several scalable methods of isolation from biomass, lignin offers many desirable properties such as biodegradability and thermal stability. In stark contrast to its benefits, lignin is generally considered a low value product and has little commercial use. In 2011, the worldwide pulp and paper industry produced 50 million tons of lignin but only 2% was used commercially while the rest was burned as a low value fuel. As the only natural aromatic polymer source, it would be extremely beneficial if lignin could be used to replace petroleum-derived aromatics in the synthesis of aromatic-based commodity polymeric materials.

The disclosure below provides methods and materials for synthesizing and manipulating lignin based polymeric materials.

SUMMARY OF THE INVENTION

The invention described herein relates to the transformation of biomass materials such as lignin into commercially desirable polymers having structures and physical properties similar to those of conventional polymers formed from petroleum products. Illustrative embodiments of the invention include compositions of matter such as aromatic-based polymers and copolymers that incorporate monolignols or functionalized monolignols as an alternative aromatic source as well as methods and materials for synthesizing such polymers. Embodiments of the invention can be used in processes designed to replace those used in petroleum-derived polymeric products. Typical embodiments of the invention include methods and materials for forming and/or modifying compounds including dicarboxylic acid ester dimers, benzoxazines and dicarboxylic acid ether dimers. Embodiments of the invention further provide methods and materials for utilizing these compounds to form commercially desirable polymers having structures and physical properties similar to those found in conventional polymers formed from petroleum products.

The invention disclosed herein has a number of embodiments. One embodiment of the invention is a method of forming a dicarboxylic acid ester dimer. This method comprises the steps of reacting an aromatic aldehyde with a malonic ester in a Doebner modification of a Knoevenagel condensation reaction so as to generate an ester compound and then reacting this ester compound with a base in situ so as to generate a salt of the ester dimer. In this method, the basic ester is then reacted with a diacid chloride or bromide in a salt metathesis reaction so as to generate an ester of a monolignol dimer; and this ester of a monolignol dimer is then converted into a carboxylic acid via a reaction with trifluoroacetic acid (TFA), so that a dicarboxylic acid ester dimer is formed. In certain embodiments of the invention, the methods can further comprise converting the dicarboxylic acid ester dirtier to a diacid chloride via a reaction with a thionyl chloride, removing excess thionyl chloride under vacuum, dissolving the diacid chloride ester dimer in a halogenated organic solvent, and then combining the halogenated organic solvent solution with an aqueous basic solution comprising a diamine in a condensation polymerization reaction so as to form a polyester-amide).

Another embodiment of the invention is a method of synthesizing a dicarboxylic acid ether dimer. This method comprises the steps of reacting an aromatic aldehyde with a malonic ester via a Doebner modification of a Knoevenagel condensation so as to generate an ester compound, and then reacting this ester compound with a base in situ so as to generate a salt of the ester compound. This method further comprises the steps of reacting this salt with a dichloroalkane or a dibromoalkane in an organic solvent while heating to reflux so as to generate a tert-butyl ester of a monolignol ether dimer. This method further comprises purifying the ether dimer via column chromatography, and then converting the ester dimer into a carboxylic acid via a reaction with trifluoroacetic acid (TFA) so that a dicarboxylic acid ether dimer is formed. Optionally the methods can further comprise polymerizing the dicarboxylic acid ether dimer so that a poly(ether-amide) is formed. In one illustrative embodiment of this, the polymerization process comprises reacting dicarboxylic acid ether dimer with thionyl chloride to generate a diacid chloride ether dimer, dissolving the diacid chloride ether dimer in an organic solvent solution, and then combining the organic solvent solution with an aqueous basic solution comprising a diamine in a polymerization reaction so as to form a poly(ether-amide).

Yet another embodiment of the invention is a method of synthesizing a benzoxazine. This method comprises the steps of reacting an aldehyde with malonic acid via a Doebner modification of a Knoevenagel condensation reaction so as to generate a carboxylic acid and then combining the carboxylic acid with a reducing agent so as to form a cinnamyl alcohol. This method then comprises performing a condensation reaction between the cinnamyl alcohol in combination with an amine and paraformaldehyde so that a benzoxazine is formed.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 8 shows the characterization of monolignol-based aromatic polyamides produced in illustrative experiments, in accordance with one or more embodiments of the invention;

FIG. 9 shows the thermal stability of monolignol-based aliphatic polyamides produced in illustrative experiments, in accordance with one or more embodiments of the invention. All temperatures are giving in ° C. Thermogravimetric analysis was performed under argon, heating from 25° C. to 650° C. at a rate of 10° C. $\text{min}^{-1}$;

FIGS. 15A-H show stacked GPC traces of poly(ester-amide) degradation, in accordance with one or more embodiments of the invention. FIG. 15A: P15 pH5 solution; FIG. 15B: P15 pH7 solution; FIG. 15C: P17 pH5 solution; FIG. 15D: P17 pH7 solution; FIG. 15E: P21 pH5 solution; FIG. 15F: P21 pH7 solution; FIG. 15G: P8 pH5 solution; FIG. 15H: P8 pH7 solution;

DETAILED DESCRIPTION OF THE INVENTION

Figure 1A:
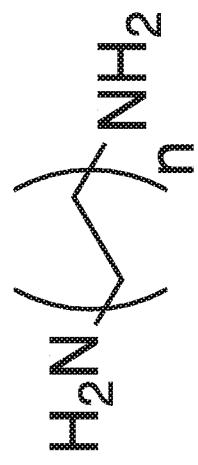
FIGS. 1A-B show aliphatic diamines used in polyamide synthesis (FIG. 1A) and aromatic diamines used in polyamide synthesis (FIG. 1B), in accordance with one or more embodiments of the invention.

Many of the techniques and procedures described or referenced herein are well understood and commonly employed using conventional methodology by those skilled in the art. In the description of the preferred embodiment, reference may be made to the accompanying drawings which form a part hereof, and in which is shown by way of illustration a specific embodiment in which the invention may be practiced. It is to be understood that other embodiments may be utilized and reagent substitutions may be made without departing from the scope of the present invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The present invention utilizes biomass to generate polymers with structures and physical properties similar to that of materials currently in use commercially. While there has been some work in identifying materials from biomass, these materials are typically mechanically weaker or suffer a reduced potential lifespan as a material. In addition, most polymers generated from biomass in the art typically use the cellulose and hemicellulose components of biomass. In contrast, the materials provided herein utilize lignin and monolignols (lignin monomers).

To utilize this natural and overlooked material as a feedstock, a series of monomers derived from monolignols have been developed for the incorporation of lignin-based monomers into polymeric materials. The resulting polymeric materials have also been systematically characterized by both material and chemical properties in illustrative experiments. These monolignol-based polymers demonstrate that lignin is useful as a replacement feedstock for the generation of alternative commodity polymeric materials from non-petroleum sources. Illustrative embodiments of this are discussed below.

The invention disclosed herein has a number of embodiments. One embodiments of the invention is a method of forming a dicarboxylic acid ester dimer. This method comprises the steps of reacting an aromatic aldehyde (e.g. vanillin, 4-hydroxybenzaldehyde, 4-hydroxy-3,5-dimethoxybenzyaldehyde or the like) with a mono-malonic ester (e.g. mono-tert-butyl malonate, mono-methyl malonate, mono-ethyl malonate, mono-benzyl malonate or the like) in a Doebner modification of a Knoevenagel condensation reaction so as to generate an ester compound; and then reacting this ester compound with a deprotonating agent (e.g. sodium hydride, sodium hydroxide, potassium carbonate, potassium hydroxide, potassium hydride or the like) in situ so as to generate a salt of the ester compound. In this method, the basic ester formed in the Doebner modification of a Knoevenagel condensation reaction is then reacted with a diacid chloride or bromide (e.g. adipoyl chloride, glutaryl chloride, succinyl chloride, pimeloyl chloride, suberoyl chloride, malonyl chloride, azelaoyl chloride, dodecanedioyl dichloride, adipoyl bromide, glutaryl bromide, succinyl bromide, pimeloyl bromide, suberoyl bromide, malonyl bromide, azelaoyl bromide, dodecanedioyl dibromide or the like) in a salt metathesis reaction so as to generate an ester of a monolignol dimer; and this ester of a monolignol dimer is then converted into a carboxylic acid via a deprotection reaction (e.g. with trifluoroacetic acid (TFA)), so that a dicarboxylic acid ester dimer is formed.

In further embodiments of the invention, the methods comprise converting the dicarboxylic acid ester dimer to a diacid chloride via a reaction with a thionyl chloride, removing excess thionyl chloride under vacuum, dissolving the diacid chloride ester dimer in a halogenated organic solvent (e.g. methylene chloride, chloroform, carbon tetrachloride or the like), and then combining the halogenated organic solvent solution with an aqueous basic solution comprising a diamine in a condensation polymerization reaction so as to form a poly(ester-amide). Typically, the reaction is an interfacial polymerization reaction. In embodiments of the invention, reaction conditions can be controlled to form materials having specific material properties, for example properties that make the invention useful in specific contexts. In certain embodiments of the invention, the poly(ester-amide) exhibits an onset of thermal decomposition ($T_{d5}$) between 220° C. and 260° C.; and/or a glass transition temperature ($T_g$) between 64.7 and 138.2° C.

In embodiments of the invention, the diamine used can be an aliphatic or aromatic diamine. Optionally, for example, the diamine is an aliphatic or aromatic diamine. Illustrative diamines useful in such methods include:

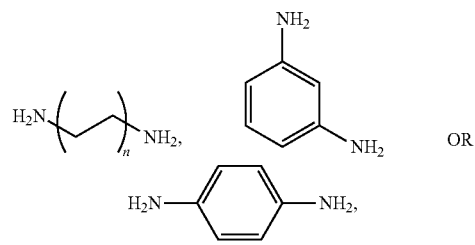

wherein n=1, 2, 3, 4 or 5.

Embodiments of the invention include methods that further purify and/or modify the poly(ester-amide) produced by the methods above. For example, this poly(ester-amide) can be modified in an atom-transfer radical-polymerization (ATRP) reaction; or a reversible addition-fragment chain transfer (RAFT) reaction. The methods can include concentrating the polyester-amide) via a precipitation process. In one such embodiment of the invention, a polyester-amide) precipitate is dissolved in a solution comprising toluene and itaconic acid or Tulipalin A, and then adding azobisisobutyronitrile (AIBN) to the solution. This solution is then degassed and then heated, and the resulting copolymer is then purified via precipitation.

Another embodiment of the invention disclosed herein is a method of synthesizing a benzoxazine. This method comprises the steps of reacting an aldehyde with malonic acid via a Doebner modification of a Knoevenagel condensation reaction so as to generate a carboxylic acid and then combining the carboxylic acid with a reducing agent (e.g. diisobutylaluminum hydride, lithium aluminum hydride, sodium borohydride or the like) so as to form a cinnamyl alcohol. This method then comprises performing a condensation reaction between the cinnamyl alcohol in combination with an amine (e.g. aniline and/or, o-toluidine, m-toluidine, p-toluidine, 1-naphthylamine, 2-aminopyridine, 3-aminopyridine, 4-aminopyridine, 8-aminoquinoline, 2-aminopurine or the like) and paraformaldehyde so that a benzoxazine is formed. Optionally this method further comprises polymerizing the benzoxazine in a ring-opening polymerization so as to form a polybenzoxazine. In certain embodiments of the invention, a thermal polymerization process is used to form a polybenzoxazine resin.

Yet another embodiment of the invention is a method of synthesizing a dicarboxylic, acid ether dimer. This method comprises the steps of reacting an aromatic aldehyde (e.g. vanillin, 4-hydroxybenzaldehyde or 4-hydroxy-3,5-dimethoxybenzyaldehyde etc.) with a malonic ester via a Doebner modification of a Knoevenagel condensation so as to generate an ester compound, and then reacting this ester compound with a base (e.g. sodium hydride, sodium hydroxide, potassium carbonate, potassium hydroxide, potassium hydride or the like) in situ so as to generate a salt. This method further comprises the steps of reacting this sodium salt compound with a dichloroalkane or a dibromoalkane (e.g. 1,4,-dibromobutane, 1,2-dibromoethane, 1,3-dibromopropane, 1,5-dibromopentane, 1,6-dibromohexane, 1,7-dibromoheptane, 1,8-dibromooctane, 1,9-dibromononane, 1,10-dibromodecane, 1,11-dibromoundecane, 1,12-dibromododecane, 1,2-dichloroethane, 1,3-dichloropropane, 1,4-dichlorobutane, 1,5-dichloropentane, 1,6-dichlorohexane, 1,7-dichloroheptane, 1,8-dichlorooctane, 1,9-dichlorononane, 1,10-dichlorodecane, 1,11-dichloroundecane, 1,12-dichlorododecane or the like) in an organic solvent while heating to reflux so as to generate a tert-butyl ester of a monolignol ether dimer. This method then comprises purifying the ether dimer via column chromatography, and then converting the ester dimer of (d) into a carboxylic acid via a deprotection reaction (e.g. with trifluoroacetic acid (TFA)) so that a dicarboxylic acid ether dimer is formed.

Optionally the methods can further comprise polymerizing the dicarboxylic acid ether dimer so that a poly(ether-amide) is formed. In one illustrative embodiment of this, the polymerization comprises reacting dicarboxylic acid ether dimer with thionyl chloride to generate a diacid chloride ether dimer, dissolving the diacid chloride ether dimer in an organic solvent solution, and then combining the organic solvent solution with an aqueous basic solution comprising a diamine (e.g. an aliphatic or aromatic diamine as discussed above) in a polymerization reaction (e.g. an interfacial polymerization reaction) so as to form a poly(ether-amide). In embodiments of the invention, reaction conditions can be controlled to form materials having specific material properties, for example properties that make the invention useful in specific contexts. In some embodiments of the invention, the poly(ester-amide) polymer exhibits an onset of thermal decomposition ($T_{d5}$) between 106° C. and 254° C.; and/or a glass transition temperature ($T_g$) between 66 and 125° C.

Artisans understand that a wide variety of permutations of the invention can be practiced using this disclosure in combination with general knowledge in the chemical arts. A number of illustrative permutations of the invention are disclosed below.

In one aspect of the present invention, a method is provided for synthesizing a polyamide. The method comprises the steps of first reacting vanillin or 4-hydroxybenzaldehyde with tert-butyl malonate via a Doebner modification of a Knoevenagel condensation to generate a tert-butyl ester. The tert-butyl ester is then reacted with sodium hydride in situ to generate a sodium salt, which is then further reacted with adipoyl chloride via a salt metathesis reaction to generate a tert-butyl ester of a monolignol dimer. The tert-butyl ester of a monolignol dimer is converted to a carboxylic acid via a reaction with trifluoroacetic acid (TFA) to generate a dicarboxylic acid monolignol dimer. In certain embodiments of the invention, the dicarboxylic acid monolignol dimer is converted to a diacid chloride via a reaction with thionyl chloride. Excess thionyl chloride is removed under vacuum and the diacid chloride is dissolved in a dichloromethane (DCM) solution. An aqueous basic solution comprising a diamine in 0.5 M NaOH is then added to the dichloromethane solution, thereby forming a polyamide as a precipitate. In one or more embodiments, the polyamide precipitate is purified via precipitation from N,N'-dimethylformamide (DMF) with methanol.

In preferred embodiments, the diamine is an aliphatic or aromatic diamine. Typically, the diamine is

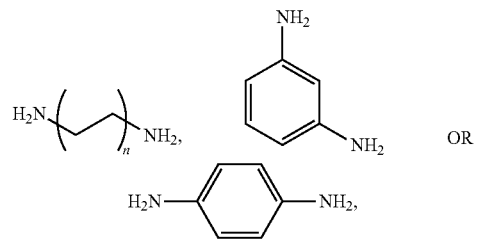

wherein n=1, 2, 3, 4 or 5. The aromatic structure of monolignols serves as a useful scaffold in monomer design.

In further embodiments, the monolignol-based polyamides are used as a polymeric backbone for a graft copolymer. In such embodiments, the method further comprises dissolving the polyamide precipitate in a solution comprising toluene along with itaconic acid or Tulipalin A. Azobisisobutyronitrile (AIBN) is added to the solution, which is then degassed via a freeze, pump or thaw method. The solution is then heated under $N_2$ to 60° C. for 12 hours. Volatiles are removed and the resulting polymer is purified via precipitation. In one or more embodiments, the polyamide is converted into an initiator with a controlled polymerization reaction. The controlled polymerization reaction may be bromination for an atom-transfer radical-polymerization (ATRP) reaction or addition of a dithiocarbonate moiety for a reversible addition-fragment chain transfer (RAFT) reaction.

In another aspect of the present invention, a method is provided for synthesizing a benzoxazine. The method comprises the steps of first reacting a vanillin or 4-hydroxybenzaldehyde with malonic acid via a Doebner modification of a Knoevenagel condensation to generate a carboxylic acid. The carboxylic acid is reduced to a monolignol with diisobutylaluminum hydride (DIBAL-H). A benzoxazine monomer is then synthesized via a condensation reaction between the monolignol with aniline and paraformaldehyde. In one or more embodiments, the condensation reaction is conducted in anisole and heated to 90° C. for 12 hours. The benzoxazine monomer may be purified via column chromatography. The benzoxazine monomer may also be thermally polymerized to a polybenzoxazine resin.

Another aspect of the present invention is a method for synthesizing a polyamide. The method comprises the steps of first reacting vanillin or 4-hydroxybenzaldehyde with tert-butyl malonate via a Doebner modification of a Knoevenagel condensation to generate a tert-butyl ester. The tert-butyl ester is then reacted with sodium hydride in situ to generate a sodium salt, which is then further reacted with adipoyl chloride via a salt metathesis reaction to generate a tert-butyl ester of a monolignol dimer. The tert-butyl ester of a monolignol dimer is converted to a carboxylic acid via a reaction with trifluoroacetic acid (TFA) to generate a dicarboxylic acid monolignol dimer. In certain embodiments of the invention, the dicarboxylic acid monolignol dimer is converted to a diacid chloride via a reaction with thionyl chloride. Excess thionyl chloride is removed under vacuum and the diacid chloride is dissolved in a dichloromethane (DCM) solution. An aqueous basic solution comprising a diamine in 0.5 M NaOH is then added to the dichloromethane solution, thereby forming a polyamide as a precipitate. In one or more embodiments, the polyamide precipitate is purified via precipitation from N,N'-dimethylformamide (DMF) with methanol.

In further embodiments, the monolignol-based polyamides are used as a polymeric backbone for a graft copolymer. In such embodiments, the method further comprises dissolving the polyamide precipitate in a solution comprising toluene along with itaconic acid or Tulipalin A. Azobisisobutyronitrile (AIBN) is added to the solution, which is then degassed via a freeze, pump or thaw method. The solution is then heated under $N_2$ to 60° C. for 12 hours. Volatiles are removed and the resulting polymer is purified via precipitation. In one or more embodiments, the polyamide is converted into an initiator with a controlled polymerization reaction. The controlled polymerization reaction may be bromination for an atom-transfer radical-polymerization (ATRP) reaction or addition of a dithiocarbonate moiety for a reversible addition-fragment chain transfer (RAFT) reaction.

In another aspect of the present invention, a method is provided for synthesizing a benzoxazine. The method comprises the steps of first reacting a vanillin or 4-hydroxybenzaldehyde with malonic acid via a Doebner modification of a Knoevenagel condensation to generate a carboxylic acid. The carboxylic acid is reduced to a monolignol with diisobutylaluminum hydride (DIBAL-H). A benzoxazine monomer is then synthesized via a condensation reaction between the monolignol with aniline and paraformaldehyde. In one or more embodiments, the condensation reaction is conducted in anisole and heated to 90° C. for 12 hours. The benzoxazine monomer may be purified via column chromatography. The benzoxazine monomer may also be thermally polymerized to a polybenzoxazine resin.

ILLUSTRATIVE WORKING EMBODIMENTS OF THE INVENTION

I. Monolignol-Based Poly(Ester-Amide)s

Figure 4A:
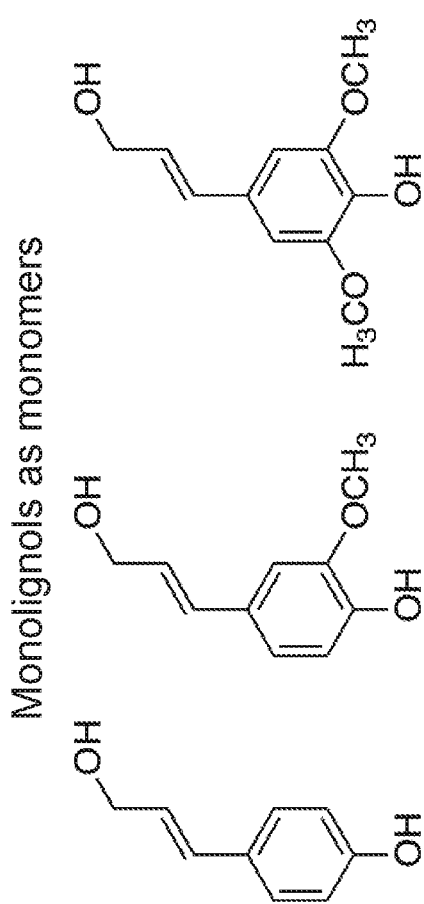
FIGS. 4A-B provide examples of monolignols (FIG. 4A) and polyamides (FIG. 4B)
Figure 4B:
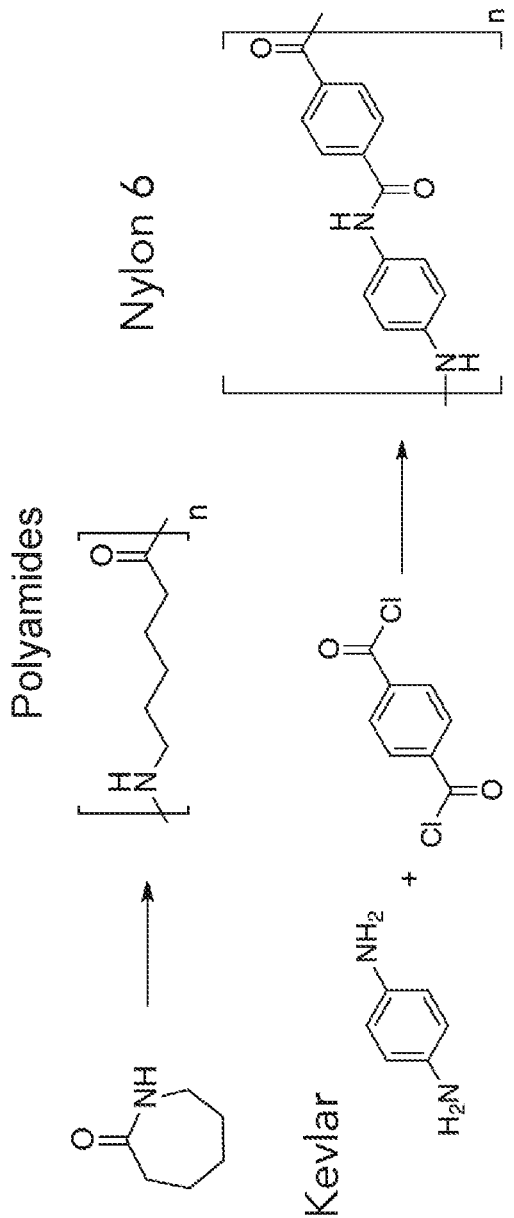

Generally, monolignols (lignin monomers) are polymerized in planta via a radical enzymatic process. Their aromatic structure with different degrees of substitution offer an interesting framework for monomer synthesis. Examples of monolignols are shown in FIG. 4A. Polyamides (see, e.g. FIG. 4B) are frequently used in commodity applications due to their high solvent resistance, strength, and melt processibility. Polyamides are most commonly produced from petroleum-based sources.

In one aspect of the invention, monolignol-based polyamides and methods for synthesizing the monolignol-based polyamides are provided. There is no knowledge of polyamides in the literature featuring this structure or synthesis process. A dicarboxylic acid monolignol dimer has been previously published by Ouimet et al. [8], however it was polymerized using triphosgene, resulting in an entirely different polymeric structure.

Figure 2:
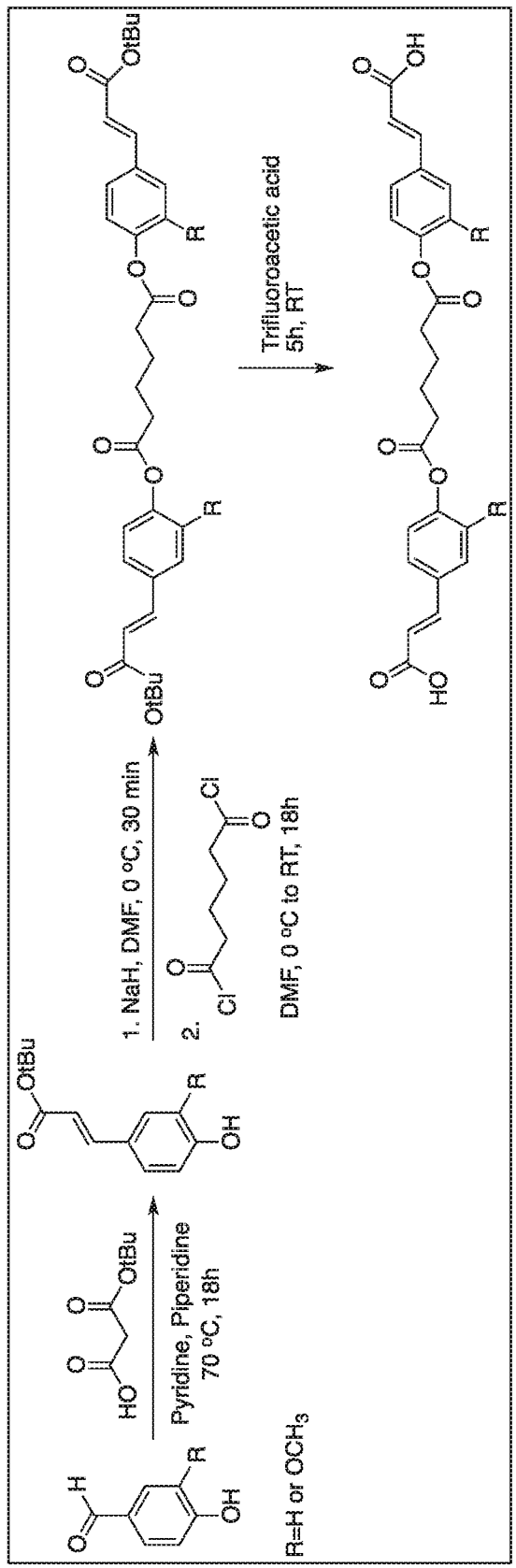
FIG. 2 shows a schematic for the synthesis of dicarboxylic acid dimer from vanillin, 4-hydroxybenzaldehyde, or 3,5-dimethoxy-4-hydroxybenzaldehyde, in accordance with one or more embodiments of the invention.
Figure 5:
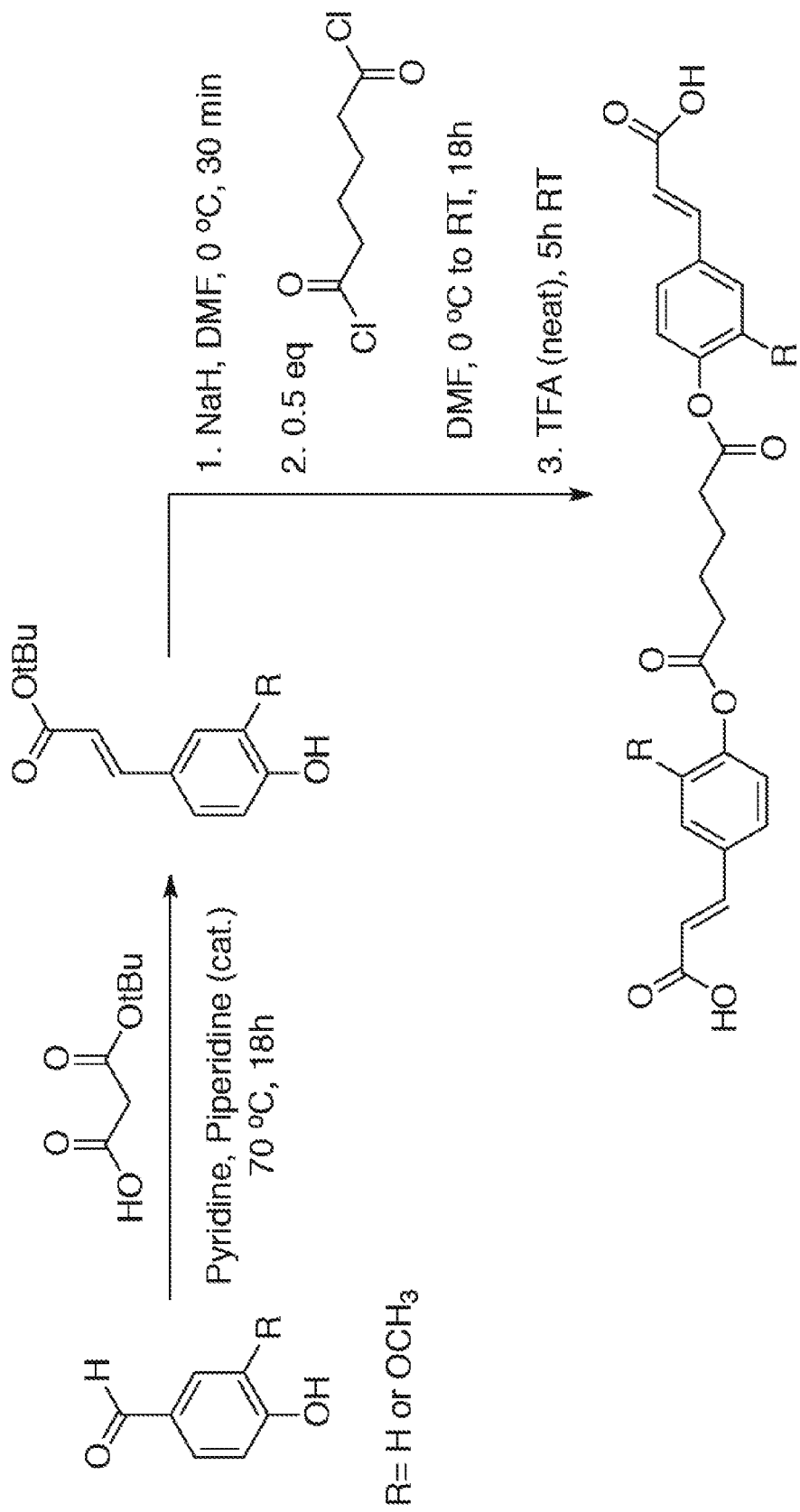
FIG. 5 shows a schematic for the synthesis of a monolignol-based dimer, in accordance with one or more embodiments of the invention.

In one or more embodiments, a dicarboxylic acid monolignol dimer is synthesized in three steps from either vanillin or 4-hydroxybenzaldehyde, as shown, for example in FIGS. 2 and 5. Vanillin or 4-hydroxybenzaldehyde is reacted with tert-butyl malonate via a Doebner modification of a Knoevenagel condensation to generate the corresponding tert-butyl ester. The sodium salt is then generated in situ via reaction with sodium hydride prior to a salt metathesis reaction with adipoyl chloride to generate the tert-butyl ester of the monolignol dimer. The tert-butyl ester is then converted to the desired carboxylic acid via reaction with trifluoroacetic acid (TFA), to generate the dicarboxylic acid monolignol dimer as the final product.

Figure 6:
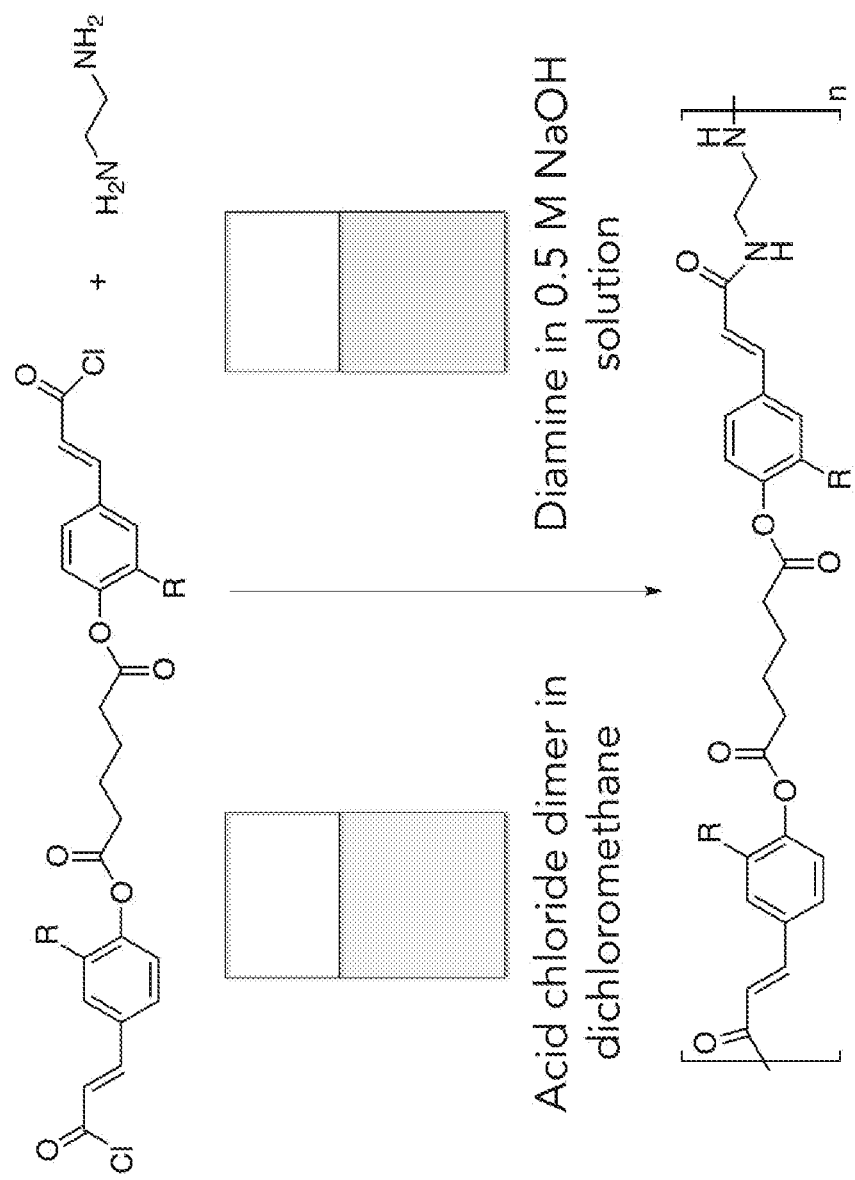
FIG. 6 shows a schematic for the synthesis of monolignol-based polyamides via interfacial polymerization, in accordance with one or more embodiments of the invention.

Synthesis of monolignol-based polyamides may be achieved via interfacial polymerization. To produce the polyamides, the dicarboxylic acid monolignol dimer is first converted to the corresponding diacid chloride via reaction with thionyl chloride. As shown in FIG. 6, after removal of excess thionyl chloride under vacuum, the resulting diacid chloride is dissolved in dichloromethane (DCM) and transferred to a 50 mL beaker with a stirbar. A separate solution of an equimolar amount of the desired diamine in 0.5 M NaOH is prepared. Once the DCM solution containing the diacid is stirring vigorously, the aqueous basic solution containing the diamine is added, immediately forming the desired polyamide as a precipitate. Specifically, the polyamides form at the interface between the two solutions of the vigorously stirred biphasic solution. The resulting polymeric solids may then be isolated via filtration and purified via precipitation from N,N'-dimethylformamide (DMF) with methanol. Polymers created by this technique have been shown to have moderate molecular weight and polydispersity as well as moderate thermal stability.

Figure 1B:
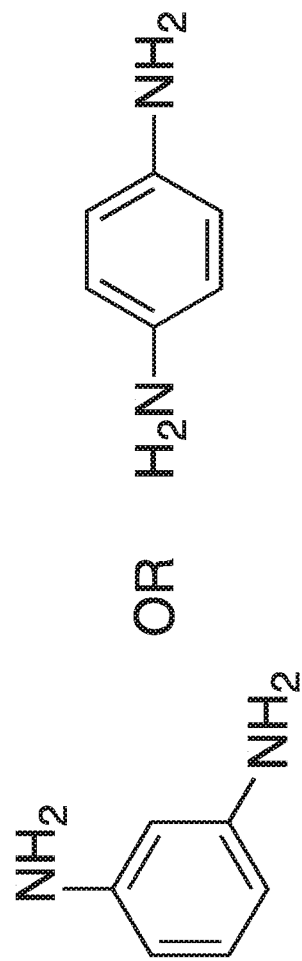
Figure 7:
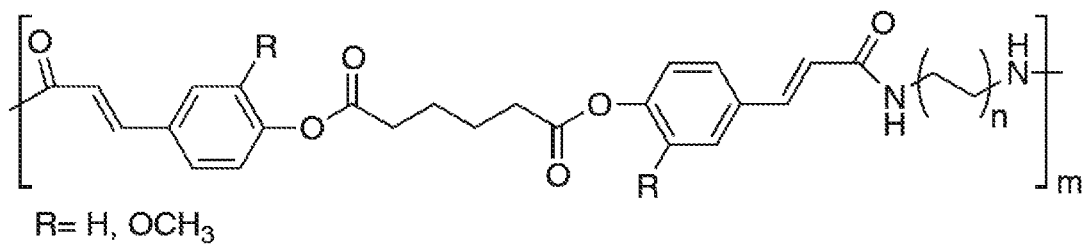
FIG. 7 shows the characterization of monolignol-based aliphatic polyamides produced in illustrative experiments, in accordance with one or more embodiments of the invention.
Figure 10:
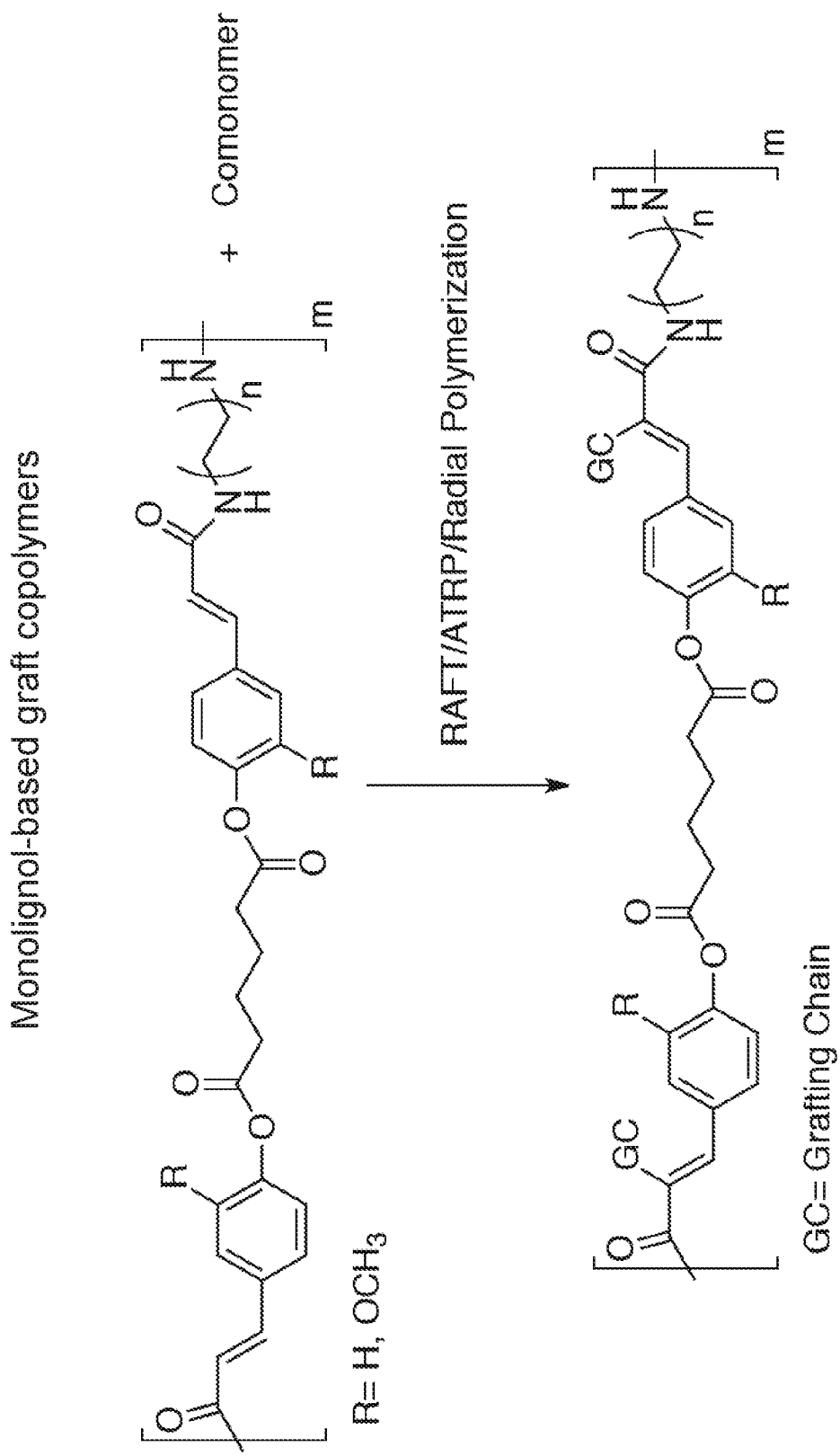
FIG. 10 shows a schematic for the synthesis of monolignol-based graft copolymers via interfacial polymerization, in accordance with one or more embodiments of the invention.

This reaction may be applied to various diamines. In certain instances, this reaction was repeated with multiple diamines, both aliphatic and aromatic (e.g. FIGS. 1A-B). In illustrative experiments, aliphatic diamines where n=2, 3 or 5 have been isolated from sugars found in biomass in relatively high yield with costs comparable to those from petroleum [10-11]. FIGS. 7-9 show the characterization of various monolignol-based polyamides synthesized in illustrative experiments. Thermogravimetric analysis was performed under oxygen, heating from 25° C. to 650° C. at a rate of 10° C. min$^{-1}$.

II. Graft-Co-Polymers from Itaconic Acid, Tulipalin A, and Monolignol-Based Polyamides Synthesis of polyamides by the above method preserves the internal alkene from the monolignol—an ideal site for grafting. Thus, in another aspect of the invention, monolignol-based polyamides are used as the polymeric backbone for the graft copolymer. As the graft-co-polymer synthesis also utilizes the polyamide as the backbone, the previous publication by Ouimet et al. [8] is also related. However, there is no knowledge of polyamide-based graft co-polymers in the literature featuring itaconic acid or Tulipalin A (shown below).

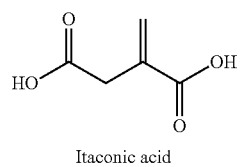
Itaconic acid

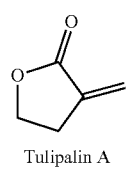
Tulipalin A

In one or more embodiments, a series of monolignol-based polyamides are synthesized as follows: A dicarboxylic acid monolignol dimer is created in three steps from either vanillin or 4-hydroxybenzaldehyde, as seen in FIG. 2. Vanillin or 4-hydroxybenzaldehyde is reacted with tert-butyl malonate via a Doebner modification of a Knoevenagel condensation to generate the corresponding tert-butyl ester. The sodium salt is then generated in situ via reaction with sodium hydride prior to a salt metathesis reaction with adipoyl chloride to generate the tert-butyl ester of the monolignol dimer. The tert-butyl ester is then converted to the desired carboxylic acid via reaction with trifluoroacetic acid (TFA), to generate the dicarboxylic acid monolignol dimer as the final product. To produce the polyamides, the dicarboxylic acid monolignol dimer is first converted to the corresponding diacid chloride via reaction with thionyl chloride. After removal of excess thionyl chloride under vacuum, the resulting diacid chloride is dissolved in dichloromethane (DCM) and transferred to a 50 mL beaker with a stirbar. A separate solution of an equimolar amount of the desired diamine in 0.5 M NaOH is prepared. Once the DCM solution containing the diacid is stirring vigorously, the aqueous basic solution containing the diamine is added, immediately forming the desired polyamide as a precipitate. This reaction may be applied to various diamines. In illustrative implementations, this reaction was repeated with multiple diamines, both aliphatic and aromatic (e.g. FIGS. 1A-B). The resulting polymeric solids may be purified via precipitation from N,N'-dimethylformamide (DMF) with methanol.

The purified polymers may then be used in grafting reactions with either itaconic acid or Tulipalin A as the comonomer. In a sample polymerization reaction, the polyamide backbone is dissolved in toluene along with itaconic acid or Tulipalin A. Azobisisobutyronitrile (AIBN), a radical initiator, is added and the solution is degassed via the freeze/pump/thaw method three times. The solution is heated under $N_2$ while heating to 60° C. for 12 hours. Volatiles are removed and the resulting polymer is purified via precipitation. This grafting from approach may also utilize controlled polymerization reactions such as atom-transfer radical-polymerization (ATRP) or reversible addition-fragment chain transfer (RAFT) by converting the initial polyamide into the appropriate initiator by either bromination for ATRP or addition of a dithiocarbonate moiety for RAFT. Selecting bio-based vinyl monomers can produce materials with desirable properties as well as interesting applications. For example, the resulting graft-copolymers may be used as flocculants in solution for the removal of heavy metals or as highly absorbent polymers due to their structural similarity to polyacrylic acid.

III. Monolignol-Based Benzoxazines and Polybenzoxazines

In another aspect of the invention, a method for synthesizing monolignol-based benzoxazines is provided. The synthesis of benzoxazines/polybenzoxazines from monolignol-derivatives has been previously reported by Comi et al. [9], however they utilized a different monolignol precursor (either the ester or carboxylic acid instead of the alcohol) and a different synthetic route. There is no knowledge other monolignol-derived benzoxazines/polybenzoxazines in literature.

Figure 3:
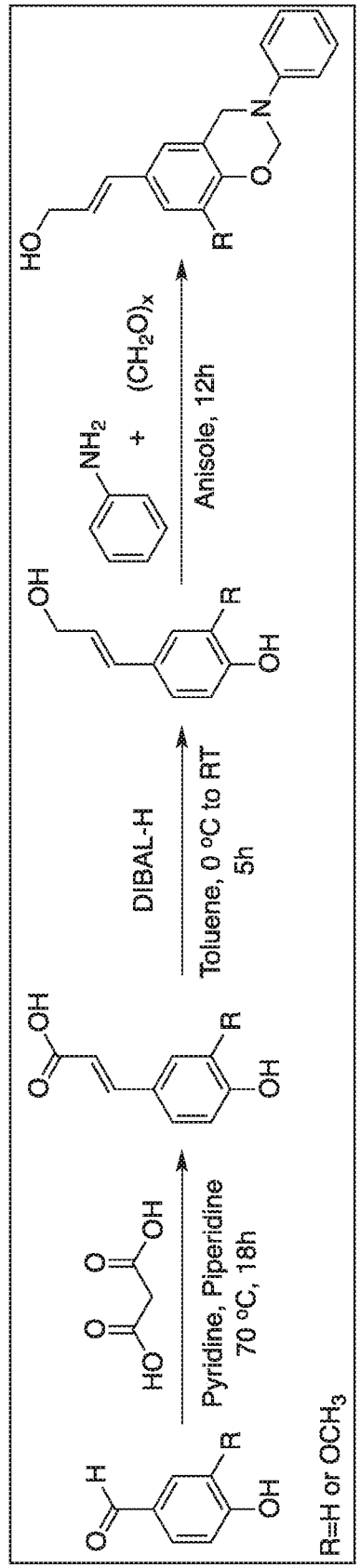
FIG. 3 shows a schematic for the synthesis of benzoxazine monomer from vanillin or 4-hydroxybenzaldehyde, in accordance with one or more embodiments of the invention.

In one or more embodiments, the monolignol-based benzoxazines are synthesized in three steps from either vanillin or 4-hydroxybenzaldehyde, as seen in FIG. 3. Vanillin or 4-hydroxybenzaldehyde is reacted with malonic acid via a Doebner modification of a Knoevenagel condensation to generate the corresponding carboxylic acid. The carboxylic acid is then reduced to the corresponding alcohol with diisobutylaluminum hydride (DIBAL-H). The resulting monolignol is then used in the synthesis of the benzoxazine monomer via a condensation reaction with aniline and paraformaldehyde. The reaction is run in anisole and heated to 90° C. for 12 hours. The resulting benzoxazine monomer is purified via column chromatography. The purified monomer may then be thermally polymerized to the corresponding polybenzoxazine resin. Both the monomer and polymer have been thermally characterized, showing both a moderate cure temperature (monomer) and moderate thermal stability (polymer).

EXAMPLES

Example 1: Monolignol-Based Benzoxazine Monomers

Polybenzoxazines have various advantages such as low water absorption, high char yield, heat and chemical resistance, and catalyst-free curing [6]. Facile synthesis of benzoxazine monomers leads to design flexibility and manipulation of material properties. Furthermore, polybenzoxazines may be used as advantageous replacements for phenolic resins (toxic chemicals in production and decomposition). An example of a polybenzoxazine is shown below:

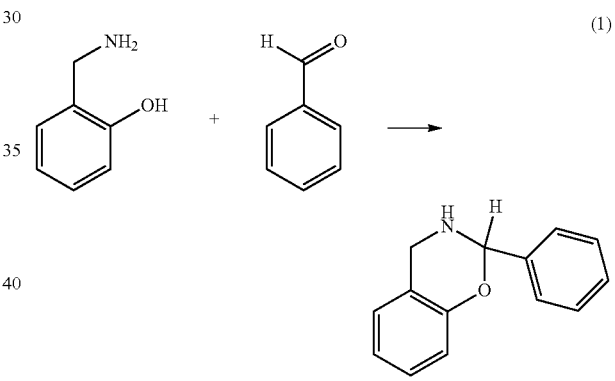

Holly, F.W. and Cope, A.C.J. Am. Chem. Soc. 1944, 66, 1875-1879

An initial route for synthesis of benzoxazines was attempted as follows:

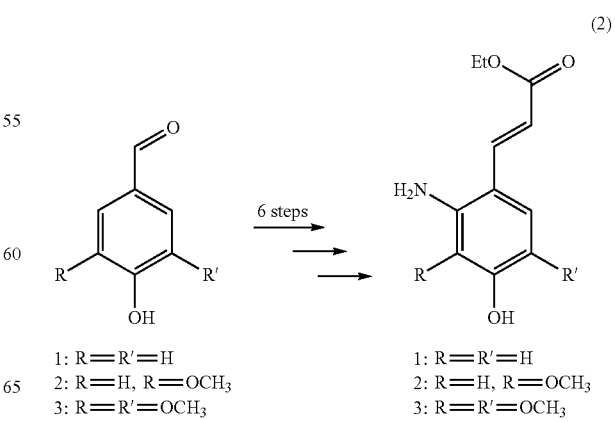

1: R=R'=H
2: R=H, R=OCH$_3$
3: R=R'=OCH$_3$

1: R=R'=H
2: R=H, R=OCH$_3$
3: R=R'=OCH$_3$

-continued

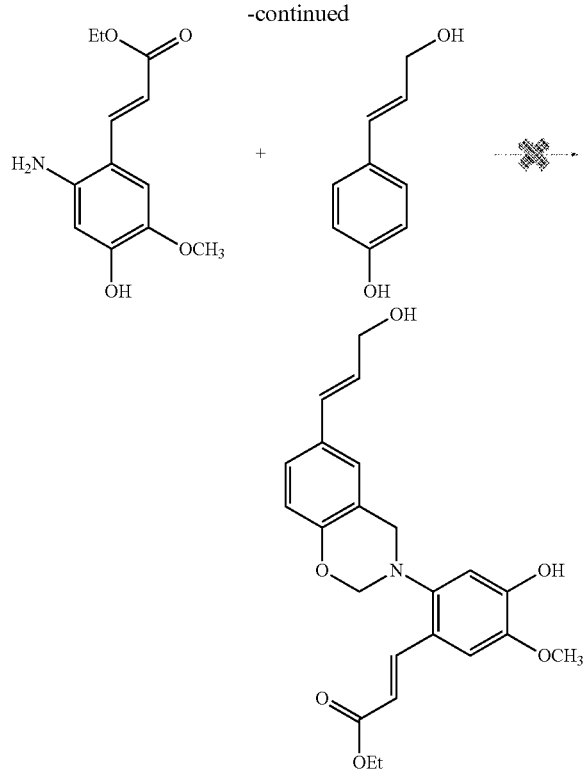

However, Mannich condensation did not yield the desired product despite several modifications of reaction conditions. This could be due to steric hindrance.

An alternative route for synthesis of benzoxazines was attempted as follows:

(3)

Here, the product was isolated in 9.8% yield. Curing and thermal stability was studied.

Polybenzoxazines were then synthesized as follows:

(4)

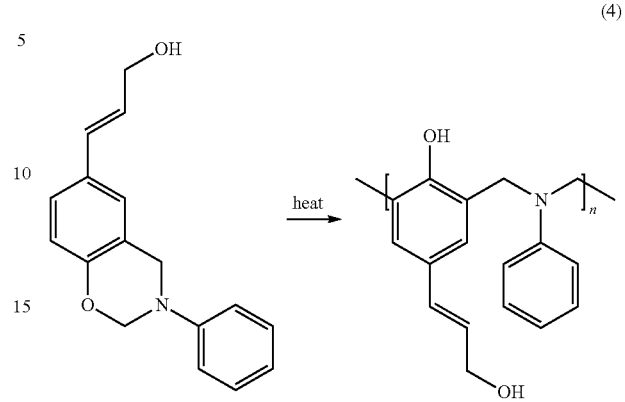

The resulting resin was characterized with DSC and TGA. The polymer was found to be sparingly soluble in organic solvents—unable to confirm product via solution-phase NMR. An onset of thermal decomposition occurred around 140° C. but there was only a 38.7% mass loss up to 361° C.

It is contemplated that a further improvement would be to modify the synthesis process to reduce synthetic steps and also to add a linker to help eliminate steric hindrance in the condensation reaction, for example:

(5)

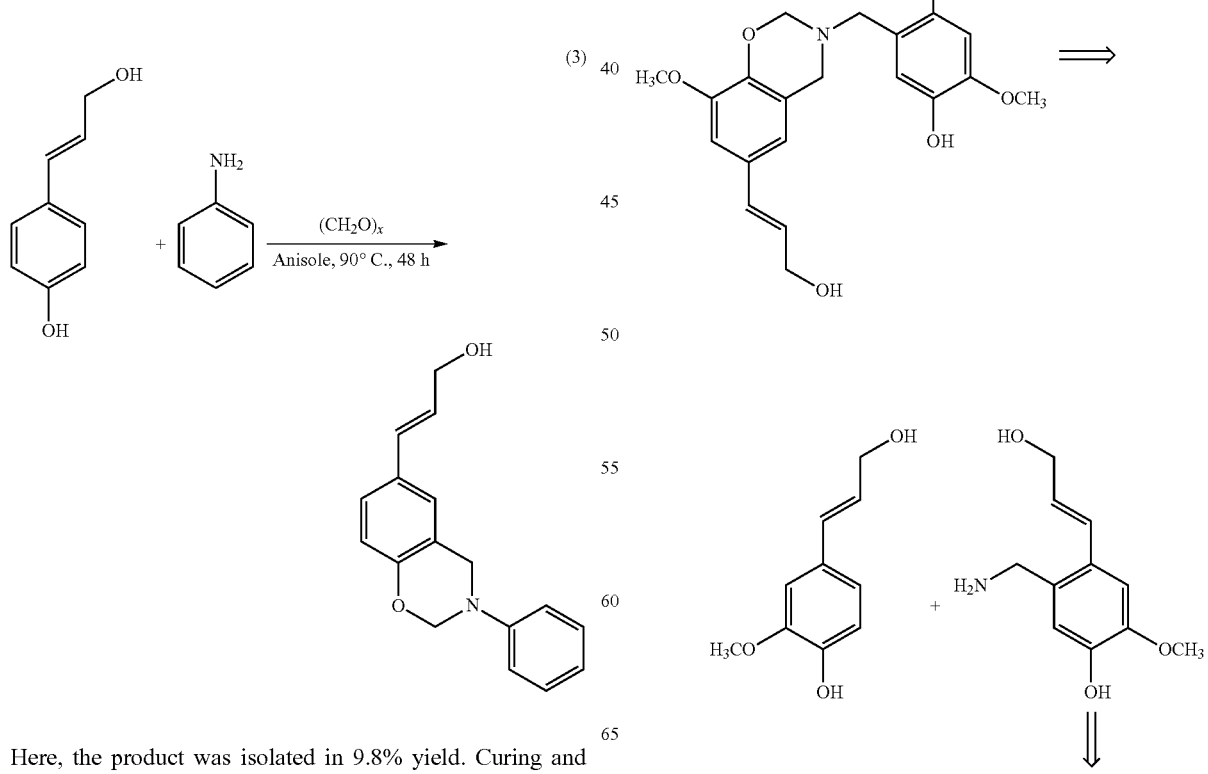

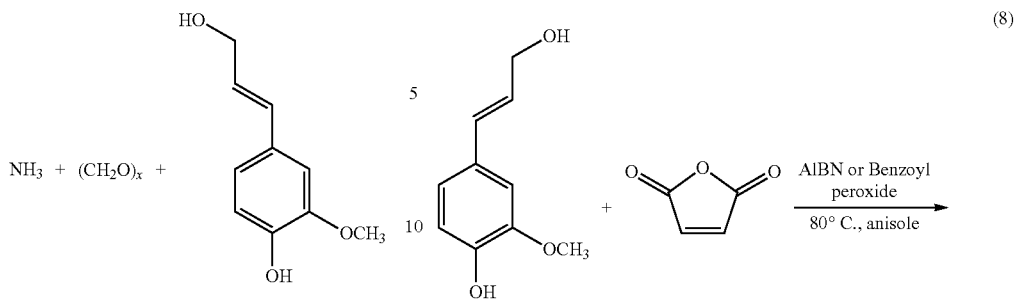

Example 2: Poly(Styrene-Co-Maleic Anhydride)

Poly(styrene-co-maleic anhydride) has various advantages such as being an alternating copolymer, optically transparent, heat resistant, and having low water absorption. Monolignols are β-substituted styrenes. RAFT has been used to control the PDI of poly(styrene-co-maleic anhydride) [7]. An example of a poly(styrene-co-maleic anhydride) is shown below:

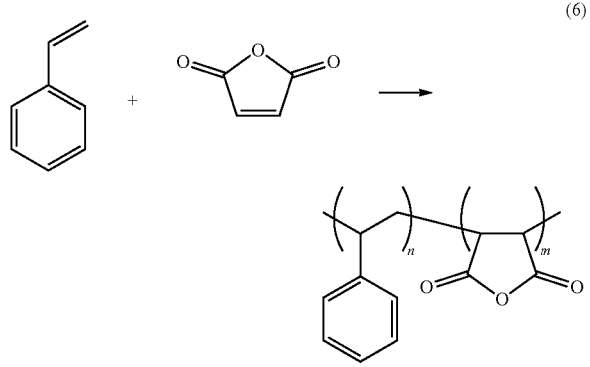

(6)

Tsuchida, E. and Tomono, T. Makromol. Chem. 1971, 141, 265-298

In a first experiment, homopolymerization of coniferyl alcohol was conducted as follows:

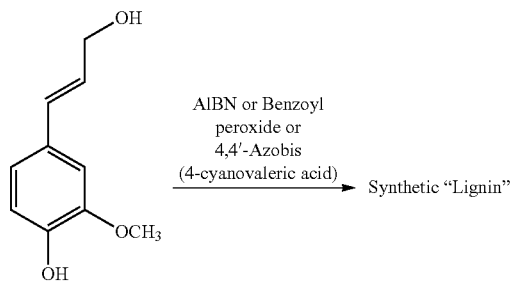

(7)

Yields were significantly lower than HRP/H$_2$O$_2$ polymerization but the isolated solid was identical in solution-phase NMR.

In a second experiment, copolymerization of coniferyl alcohol with maleic anhydride was conducted as follows:

The yield/results obtained from various conditions are shown in Table 1 below. It was found that the isolated solid was sparingly soluble in organic solvents. GPC (in THF) showed low molecular weight oligomers (Mn<1100 g/mol).

TABLE 1

| Initiator (I) | [Initiator] | Temp °C. | Time | Yield/Results |
|---|---|---|---|---|
| Benzoyl Peroxide | 1 mol % | 80° C. | 18 h | 12.2%, yellow solid precipitate |
| Benzoyl Peroxide | 5 mol % | 80° C. | 18 h | 15.1%, yellow solid precipitate |
| Benzoyl Peroxide | 1 mol % | 80° C. | 96 h* | 18.6%, yellow solid precipitate |
| Benzoyl Peroxide | 5 mol % | 80° C. | 96 h* | 23.2%, yellow solid precipitate |

*An additional eq of initiator was added every 24 hours e.g. for entry 3, 1 mol % benzoyl peroxide was added every 24 hours meaning a total of 4 mol % was added over the course of the reaction.

In a third experiment, copolymerization of coniferyl alcohol with maleic anhydride via RAFT was conducted as follows:

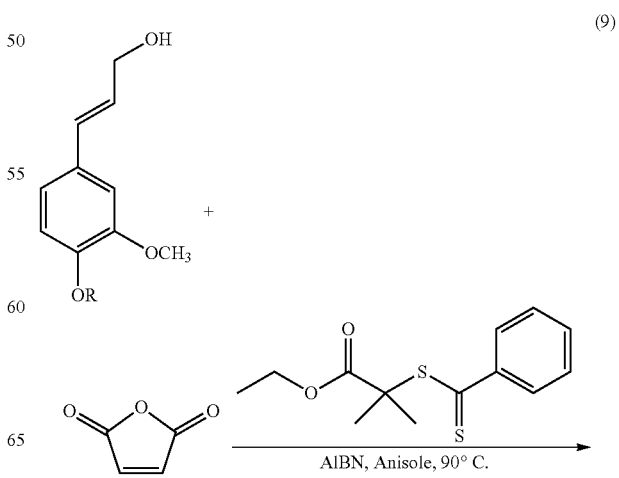

(9)

-continued

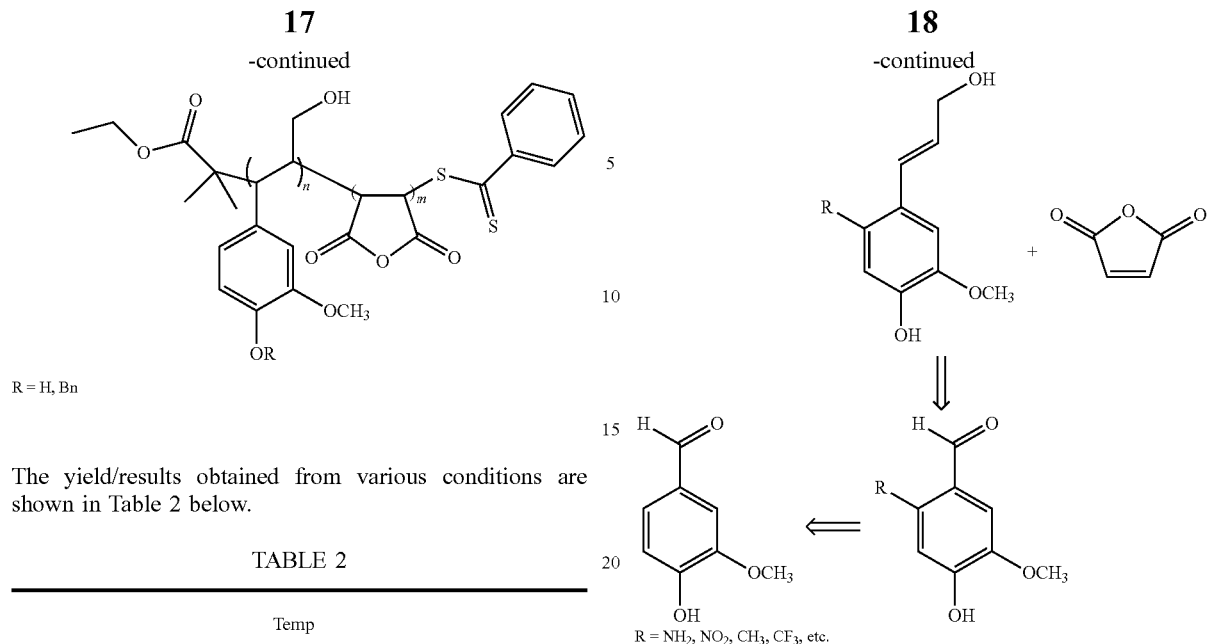

R = H, Bn

The yield/results obtained from various conditions are shown in Table 2 below.

TABLE 2

| R | Initiator | CTA | DP | Temp (° C.) | Time | Results |
|---|---|---|---|---|---|---|
| H | AIBN (1 eq) | ECPDB (0.3 eq) | 25 | 90° C. | 36 h | No precipitation during reaction. Beige solid w/ CH$_2$Cl$_2$ precipitation |
| H | AIBN (1 eq) | ECPDB (0.3 eq) | 25 | 90° C. | 84 h | No precipitation during reaction. Beige solid w/ CH$_2$Cl$_2$ precipitation |
| Bn | AIBN (1 eq) | ECPDB (0.3 eq) | 25 | 90° C. | 36 h | No precipitation during reaction. Yellow solid w/ MeOH precipitation |
| Bn | AIBN (1 eq) | ECPDB (0.3 eq) | 25 | 90° C. | 84 h | No precipitation during reaction. Yellow solid w/ MeOH precipitation |

* Bn = Benzyl; CTA = 2-(Ethoxycarbonyl)-2-propyldithiobenzoate (ECPDB); DP = Degree of polymerization for each monomer.

It is contemplated that a further improvement would be to substitute monolignol with EWD or ED groups to change copolymerization/polymerization reactivity. Standard lignin chemical degradation techniques (e.g. thioacidolysis, acidolysis) may be applied to aid in solution-phase. For example:

(10)

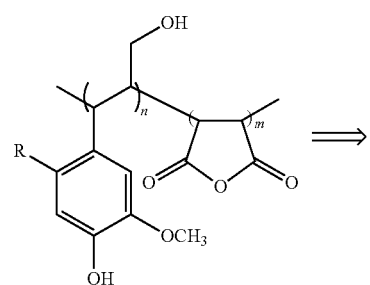

⇒

Example 3: Biodegradable Aromatic-Aliphatic Poly(Ester-Amides) from Monolignol-Based Ester Dimers Three different aromatic ester dimers, each corresponding to a different monolignol, were synthesized and characterized. The dicarboxylic acid dimers were converted to the corresponding diacid chloride in situ with thionyl chloride and a series of poly(ester-amides) were synthesized via interfacial polymerization with seven different aliphatic or aromatic diamine monomers. The thermal properties (thermal decomposition, glass transition temperature, and melting temperature) and degradation in acidic and neutral aqueous conditions of the resulting polymers were studied.

Aromatic units are typically introduced to polymers to improve the thermal and mechanical properties of the resulting material, as seen in the difference in thermo-mechanical properties of aliphatic and aromatic polyesters. Aliphatic polyesters are typically amorphous, have a low softening point, and readily degrade in both acidic or basic conditions [19]. Conversely, aromatic polyesters are known for their structural rigidity, thermal stability, and lack of biodegradation, as exemplified by polyethylene terephlatate (PET) [20]. Similar effects can also be seen in polyamides, where wholly aromatic polyamides, such as Nomex and Kevlar, feature high strength and thermal stability in comparison to aliphatic analogues, such as Nylon 6.

Poly(ester-amide)s (PEAs) are polymers which contain both an ester and amide linkage in their backbone. These materials are interesting as they commonly exhibit a mixture of properties of both polyesters and polyamides [21]. Polyesters readily degrade through hydrolysis of their ester linkage, generally feature better solubility in organic solvents, and are typically more flexible. Polyamides are thermally and mechanically robust due to hydrogen bonding between the amide linkages of individual polymer chains. Polyamides are also generally considered non-degradable, due to the slow rate of amide hydrolysis [22]. With the combination of these properties, poly(ester-amide)s are typically sought for applications that require good thermo-mechanical properties, as well as biocompatibility and biodegradation, such as biomedical applications or high-performance polymers with reduced environmental impact [23]. Poly(ester-amide)s are typically synthesized either by the polycondensation of bis-functionalized monomers [24] or by the ring-opening polymerization of depsipeptides [25,26]. While a multitude of PEAs from petroleum-based feedstocks have been synthesized and characterized, there are few examples of poly(ester-amide)s from alternative, bio-based feedstocks. Development of these materials is a critical goal to mitigate petroleum dependence. Lebarbe et al. developed a series of poly(ester-amide)s from castor oil, via the base-catalyzed condensation of C20 dimethyl esters and diols (all from methyl 10-undecenoate) [27]. The resulting polymers featured high thermal stability, with $T_{d5}>330°$ C., and semi-crystallinity. Zuo generated a series of poly (ester-amide)s from alanine-functionalized oleic acid and azelaoyl dichloride [28]. By altering the ratios of the monomers, they were able to raise or lower the $T_g$ of the materials by increasing or decreasing, respectively, the percentage of amide bonds present. Triki and coworkers described the synthesis of a series of PEAs from a bis-functional furan monomer, hexamethylenediamine, and 1,2-ethanediol [29]. The glass transition temperature of these materials was similarly shown to increase with increasing amide content, but the synthesis of these materials featured several side reactions. End-group etherification and the formation of non-reactive end groups inhibited poly(ester-amide) formation while amide-amine crosslinking lead to the formation of poorly-defined crosslinked materials. Pinilla et al. reported the synthesis of poly(ester-amide)s from a linear carbohydrate derivative of D-xylitol and commercial aromatic diacid halides [30]. Wang et al. recently reported the synthesis of a series of linear PEAs from bio-based chemicals that featured controllable degradation based on monomer feedstock ratios [31]. However, to the best of our knowledge, aromatic-aliphatic poly(ester-amide)s from bio-based feedstocks have yet to be developed.

With this in mind, we synthesized a series of twenty-one poly(ester-amide)s from monolignol-based ester dimers to study the effects of diamine linker identity and methoxy-substitution on the thermal properties and degradation of the resulting polymers. The addition of methoxy side groups should increase the hydrophilicity and therefore the increase degradation of the poly(ester-amide)s, while increased aromatic content or aliphatic chain length should increase the hydrophobicity and reduce the extent of hydrolysis. Five aliphatic and two aromatic diamine linkers were chosen for polymer synthesis, as well as three monolignol-based carboxylic acid ester dimers. Ethylene diamine, 1,4-butanediol, hexamethylenediamine, 1,8-diaminooctane, and 1,10-diaminodecane were chosen as aliphatic linkers due to their availability from biological feedstocks. The production of ethylene diamine, 1,4-butanediol, and hexamethylenediamine has been reported from C5 and C6 plant sugars [32] while 1,8-diaminooctane [33] and 1,10-diaminodecane [34] have been produced from castor oil. While neither aromatic diamine used is commercially available from biological sources yet, other small functionalized aromatics such as catechol and styrene [32] have been successfully sourced from lignin, providing encouragement that these chemicals could eventually also be biologically sourced. Additionally, these monomers were chosen so that a modular approach could be used to generate a series of polymers with tunable properties. With these starting materials in hand, a series of poly(ester-amide)s were synthesized via interfacial polymerization. The resulting family of bio-based polymers was then studied for the effects of each structural variation on thermal stability, glass transition temperature ($T_g$), melting temperature ($T_m$), and decomposition in both neutral and acidic conditions.

EXPERIMENTAL

Materials 4-hydroxybenzaldehyde (98%, TCI America), vanillin (99%, Alfa Aesar), 3,5-dimethoxy-4-hydroxybenzaldehyde (98%, Acros), malonic acid (99%, Alfa Aesar), tert-butanol (99%, Alfa Aesar), acetic anhydride (99.5%, Fisher), acetone (ACS Grade, Fisher), sulfuric acid (conc., ACS Grade, Fisher), adipoyl chloride (99%, Acros), piperidine (99%, Spectrum), trifluoroacetic acid (99.5%, Fisher) 1,4-diaminobutane (98+%, Alfa Aesar), 1,8-diaminooctane (98%, Acros), 1,10-diaminodecane (97%, Acros), p-phenylenediamine (99+%, Acros), m-phenylenediamine (99+%, Acros), sodium hydroxide (ACS Grade, Fisher), and N,N-dimethylformamide (HPLC grade, Alfa Aesar) were purchased and used as received. Pyridine (99%, Fisher) was distilled over KOH prior to use. Dichloromethane (ACS Grade, Fisher) was distilled over calcium hydride prior to use. Hexamethylene diamine (99.5%, Acros) was sublimed under reduced pressure prior to use. Ethylenediamine (98%, Acros) was distilled prior to use to remove discoloration. Meldrum's acid [35] and tert-butyl malonate [36] were synthesized according to published procedures. Silica gel 60 (230-400 mesh, Fisher) was used for column chromatography. Thin layer chromatography (TLC) was conducted with silica gel 60-F245 plates and visualized with a handheld UV lamp. NMR solvents $d_6$-DMSO, CDCl$_3$, and C$_6$D$_6$ were obtained from Cambridge Isotope Laboratories and used as received.

$^1$H, $^{13}$C, and FTIR Spectroscopy $^1$H NMR spectra were recorded on Bruker AV-300 or Bruker DRX-500 spectrometers at room temperature in $d_6$-DMSO, CDCl$_3$, or C$_6$D$_6$. Chemical shifts are reported with respect to internal solvent, 2.50 ppm ($d_6$-DMSO), 7.26 (CDCl$_3$) or 7.16 (C$_6$D$_6$) for $^1$H NMR spectra. $^{13}$C NMR spectra were recorded on a Bruker AV-500 spectrometer with a dual cryoprobe ($^{13}$C, $^1$H). Chemical shifts are reported with respect to internal solvent, 39.52 ppm ($d_6$-DMSO), 77.16 ppm (CDCl$_3$), or 128.06 (C$_6$D$_6$) for $^{13}$C NMR spectra. Infrared absorption spectra were collected using a Jasco 4210-FT/IR spectrometer from 4000 to 400 cm$^{-1}$ from KBr pellets. All samples were dried at 100° C. in a vacuum oven overnight (at least 12 h) prior to characterization.

Molecular Weight Characterization

Molecular weight ($M_n$ and $M_w$) and dispersity (Đ=$M_w$/$M_n$) were determined using gel permeation chromatography (GPC). Samples were dissolved in 10 mM LiBr in N,N-dimethylformamide (DMF) at a concentration of 1-5 mg/mL and were passed through a 0.20 µm PTFE filter before injection. GPC for all polymers was conducted on a Jasco system equipped with a refractive index detector, a UV detector, a Waters Styragel guard column, and four Waters HR Styragel 5 µm columns (100-5K, 500-30K, 50-100K, 5-600 K) using 10 mM LiBr in N,N-dimethylformamide (DMF) at 40° C. and a flow rate of 1.0 mL/min. Calibration was performed using nine near-monodisperse polystyrene standards ($M_n$=1,250 to 549,000 Da) from Jordi Laboratories and chromatograms were analyzed using ChromNAV chromatography software. For the degradation studies, due to the low sample concentration in each aliquot, raw GPC traces were smoothed using a median filter (n=15) and normalized in Microsoft Excel.

Thermal Characterization

All samples were dried at 100° C. in a vacuum oven overnight (at least 12 h) prior to all thermal characterization. Thermogravimetric analysis (TGA) was conducted on a Perkin Elmer Pyris Diamond TG/DTA Thermogravimetric/Differential Thermal Analyzer. The TGA instrument was operated under an argon atmosphere, using platinum crucibles. Samples (6-12 mg) were heated from 25 to 800° C. at a rate of 10° C./min and held at 800° C. for five minutes. Pyris Manager was used to analyze the data. Decomposition temperatures $T_{d5}$, $T_{d10}$, and $T_{d25}$ were measured at 5, 10, and 25% mass loss, respectively. Differential scanning calorimetry (DSC) was performed on a Perkin Elmer DSC 8000 to determine glass transition ($T_g$) and melting ($T_m$) temperatures, as applicable. Samples (5-8 mg) were heated from −10 to 200° C. at a rate of 10° C./min and cooled to −10° C. at a rate of 10° C./min. A minimum of two heating and cooling cycles were performed and $T_g$ and $T_m$ were measured from the second heating cycle. Pyris Manager was used to analyze the data.

Tert-Butyl Ester Monomer Synthesis p-Coumaroyl Tert-Butyl Ester (2a).

4-hydroxybenzaldehyde (6.99 g, 57.3 mmol, 1 eq) was weighed and added to a round bottom flask along with tert-butyl malonate (11.01 g, 68.7 mmol, 1.2 eq). 30.0 mL of pyridine and 0.3 mL of piperidine were added to the reaction mixture and the reaction was heated to reflux overnight. After refluxing, the reaction was cooled to room temperature and concentrated under reduced pressure. The resulting residue was dissolved in diethyl ether (70 mL) and washed with saturated sodium bicarbonate (2×70 mL), 1 M HCl (2×40 mL), and deionized water (1×40 mL). The organic layer was dried over $MgSO_4$ and solvent was removed via rotary evaporation to yield the crude product. The compound was purified on silica gel via flash column chromatography using 3:2 hexanes:ethyl acetate as the elutant. Yield: 4.04 g, 32.1% $^1$H NMR (300 MHz, $d_6$-DMSO): δH 7.67 (d, 2H, Ar—H), 7.62 (d, 1H, CCH=CHCOO(CH$_3$)$_3$), 7.20 (d, 2H, Ar—H), 6.54 (d, 1H, CCH=CHCOO(CH$_3$)$_3$), 1.48 (s, 9H, COO(CH$_3$)$_3$).

Feruloyl Tert-Butyl Ester (2b).

Yield: 6.49 g, 65.3% $^1$H NMR (300 MHz, $d_6$-DMSO): δH 7.48 (d, 1H, CCH=CHCOO(CH$_3$)$_3$), 7.27 (s, 1H, Ar—H), 7.08 (d, 1H, Ar—H), 6.80 (d, 1H, Ar—H), 6.37 (d, 1H, CCH=CHCOO(CH$_3$)$_3$), 3.81 (s, 3H, Ar—OCH$_3$), 1.47 (s, 9H, COO(CH$_3$)$_3$).

Sinapoyl Tert-Butyl Ester (2c).

3,5-dimethoxy-4-hydroxybenzaldehyde (3.17 g, 17.4 mmol, 1 eq) was weighed and added to a round bottom flask along with tert-butyl malonate (3.90 g, 24.4 mmol, 1.2 eq). 20.0 mL of pyridine and 0.2 mL of piperidine were added to the reaction mixture and the reaction was heated to reflux overnight. After refluxing, the reaction was cooled to room temperature and concentrated under reduced pressure. The resulting residue was dissolved in diethyl ether (50 mL) and washed with saturated sodium bicarbonate (2×50 mL), 1 M HCl (2×30 mL), and deionized water (1×30 mL). The organic layer was dried over $MgSO_4$ and solvent was removed via rotary evaporator to yield the product as a white solid. The compound was purified on silica gel via flash column chromatography using 3:2 hexanes:ethyl acetate as the elutant. Yield: 3.57 g, 73.1% $^1$H NMR (300 MHz, $d_6$-DMSO): δH 8.89 (s, 1H, Ar—OH), 7.47 (d, 1H, CCH=CHCOO(CH$_3$)$_3$), 6.98 (s, 2H, Ar—H), 6.44 (d, 1H, CCH=CHCOO$^t$Bu), 3.79 (s, 6H, Ar—OCH$_3$), 1.48 (s, 9H, COOC(CH$_3$)$_3$). $^{13}$C NMR (500 MHz, $d_6$-DMSO): δC 166.46 (CCH=CHCOO(CH$_3$)$_3$), 148.46 (C—OCH$_3$), 144.87 (CCH=CHCOO(CH$_3$)$_3$), 138.50 (C—OH), 124.97 (CCH=CHCOO(CH$_3$)$_3$), 117.26 (CCH=CHCOO(CH$_3$)$_3$), 106.49 (Ar C—H), 79.90 (C(CH$_3$)$_3$), 56.53 (OCH$_3$), 28.39 (C(CH$_3$)$_3$).

Tert-Butyl Ester Dimer Synthesis p-Coumaroyl tert-butyl ester dimer (3a) [37] and feruloyl tert-butyl ester dimer (3b) [38] were synthesized as reported previously by Ouimet et al.

p-Coumaroyl Tert-Butyl Ester Dimer (3a).

Yield: 2.33 g, 70.1% $^1$H NMR (300 MHz, $d_6$-DMSO): δH 7.65 (d, 2H, Ar—H), 7.61 (d, 1H, CCH=CHCOOH), 7.21 (d, 2H, Ar—H), 6.56 (d, 1H, CCH=CHCOOH), 2.69 (br s, 2H, OCH$_2$CH$_2$), 1.77 (br s, 2H, OCH$_2$CH$_2$), 1.49 (s, 9H, COO(CH$_3$)$_3$).

Feruloyl Tert-Butyl Ester Dimer (3b).

Yield: 2.61 g, 74.4% $^1$H NMR (300 MHz, $d_6$-DMSO): δH 7.50 (d, 1H, CCH=CHCOO(CH$_3$)$_3$), 7.31 (s, 1H, Ar—H), 7.20 (d, 1H, Ar—H), 6.99 (d, 1H, Ar—H), 6.46 (d, 1H, CCH=CHCOO(CH$_3$)$_3$), 3.80 (s, 3H, Ar—OCH$_3$), 2.81 (br s, 2H, OCH$_2$CH$_2$) 1.79 (br s, 2H, OCH$_2$CH$_2$), 1.48 (s, 9H, COO(CH$_3$)$_3$).

Sinapoyl Tert-Butyl Ester Dimer (3c).

Sinapoyl tert-butyl ester (4.99 g, 17.8 mmol, 2 eq) was weighed and added to a two-necked round bottom flask along with 30 mL of N,N-dimethylformamide (DMF). The reaction mixture was cooled to 0° C. and sodium hydride (0.64 g, 26.7 mmol, 3 eq) was added portionwise. After 30 minutes, a solution of adipoyl chloride (1.3 mL, 8.9 mmol) in 5 mL DMF was added dropwise over 30 minutes via an addition funnel. The reaction was allowed to slowly warm to room temperature and stir for 5 hours. After 5 hours, the reaction was diluted with ethyl acetate (70 mL) and washed with deionized water (2×70 mL). The organic layer was separated, dried over $MgSO_4$, and volatiles were removed via rotary evaporator to yield the crude product as a white solid. The product was purified on silica gel via flash column chromatography using 3:2 hexanes:ethyl acetate as the elutant. Yield: 1.89 g, 31.7% $^1$H NMR (300 MHz, $C_6D_6$): δ 7.84 (d, 1H, CCH=CHCOO(CH$_3$)$_3$), 6.52 (d+s, 3H, Ar—H+CCH=CHCOO(CH$_3$)$_3$), 3.23 (s, 6H, Ar—OCH$_3$), 2.44 (br s, 2H, OCH$_2$CH$_2$), 1.73 (br s, 2H, OCH$_2$CH$_2$), 1.52 (s, 9H, C(CH$_3$)$_3$). $^{13}$C NMR (500 MHz, $C_6D_6$): δ 170.49 (COOCCH$_2$CH$_2$), 166.04 (CCH=CHCOO(CH$_3$)$_3$), 153.19 (COCH$_3$), 143.96 (CCH=CHCOO(CH$_3$)$_3$), 132.99 (CCH=CHCOO(CH$_3$)$_3$), 131.29 (COOCCH$_2$CH$_2$), 120.69 (CCH=CHCOO(CH$_3$)$_3$), 104.74 (Ar), 80.16 (C(CH$_3$)$_3$), 55.58 (COCH$_3$), 33.73 (COOCCH$_2$CH$_2$), 28.29 (C(CH$_3$)$_3$), 24.59 (COOCCH$_2$CH$_2$).

Diacid Ester Dimer Synthesis p-Coumaryl diacid dimer (4a) [37] and ferulyl diacid dimer (4b) [38] were synthesized as reported previously by Ouimet et al.

p-Coumaryl Diacid Dimer (4a).

Yield: 1.08 g, 92.3% $^1$H NMR (300 MHz, $d_6$-DMSO): 7.67 (d, 2H, Ar—H), 7.62 (d, 1H, CCH=CHCOOH), 7.20 (d, 2H, Ar—H), 6.54 (d, 1H, CCH=CHCOOH), 2.67 (br s, 2H, OCH$_2$CH$_2$), 1.75 (br s, 2H, OCH$_2$CH$_2$).

Ferulyl Diacid Dimer (4b).

Yield: 1.12 g, 94.8% $^1$H NMR (300 MHz, $d_6$-DMSO): 7.51 (d, 1H, CCH=CHCOO(CH$_3$)$_3$), 7.29 (s, 1H, Ar—H), 7.20 (d, 1H, Ar—H), 6.98 (d, 1H, Ar—H), 6.46 (d, 1H, CCH=CHCOO(CH$_3$)$_3$), 3.82 (s, 3H, Ar—OCH$_3$), 2.82 (br s, 2H, OCH$_2$CH$_2$) 1.78 (br s, 2H, OCH$_2$CH$_2$).

Sinapyl Diacid Dimer (4c).

Sinapoyl tert-butyl ester dimer (1.69 g, 2.5 mmol, 1 eq) was weighed and added to a round bottom flask along with trifluoroacetic acid (7.7 mL, 100.6 mmol, 40 eq). Reaction was stirred at room temperature for 4 hours. Volatiles were removed via rotary evaporation to yield the product as a white solid. Yield: 1.31 g, 93.1% $^1$H NMR (300 MHz, $d_6$-DMSO): δ 7.59 (d, 1H, CCH=CHCOOH), 7.09 (s, 2H, Ar—H), 6.64 (d, 1H, CCH=CHCOOH), 3.79 (s, 6H, COCH$_3$), 2.62 (br s, 2H, OCH$_2$CH$_2$), 1.77 (br s, 2H, OCH$_2$CH$_2$) $^{13}$C NMR (500 MHz, $d_6$-DMSO): δ 170.54 (COOCH$_2$CH$_2$), 167.63 (CCH=CHCOOH), 151.98 (COCH$_3$), 143.82 (CCH=CHCOOH), 132.63 (CCH=CHCOOH), 129.43 (COOCCH$_2$CH$_2$), 119.71 (CCH=CHCOOH), 105.18 (Ar), 56.14 (COCH$_3$), 32.74 (COOCCH$_2$CH$_2$), 23.83 (COOCCH$_2$CH$_2$).

Poly(Ester-Amide) Synthesis

General Polymerization Procedure.

The desired diacid dimer (1 eq) was weighed and added to a round bottom flask. Thionyl chloride (20 eq) was added to the flask along with a drop of DMF, and the reaction was heated to reflux for 6 hours. Volatiles were removed, under vacuum, to yield the diacid chloride dimer. The desired diamine (3 eq) was weighed and added to a 100 mL beaker along with 15 mL of 0.5 M NaOH and a stir bar. The isolated diacid chloride dimer was dissolved in 15 mL of distilled dichloromethane and added quickly to the rapidly stirring diamine solution. A solid precipitate formed immediately and the resulting slurry was allowed to stir for two minutes. The slurry was transferred to an Eppendorf tube and centrifuged at $4.4\times10^3$ rpm for 20 minutes. The biphasic solution was decanted from the Eppendorf tube and the residual solid was washed with water (2×15 mL). After each washing, the slurry (water & polymer) was centrifuged at $4.4\times10^3$ rpm for 10 minutes. The resulting solid was dried under reduced pressure to yield the corresponding polymer as a pale yellow solid. The resulting polymers were insoluble to common solvents and sparingly soluble in DMF.

Results and Discussion

Dimer Synthesis

Figure 11:
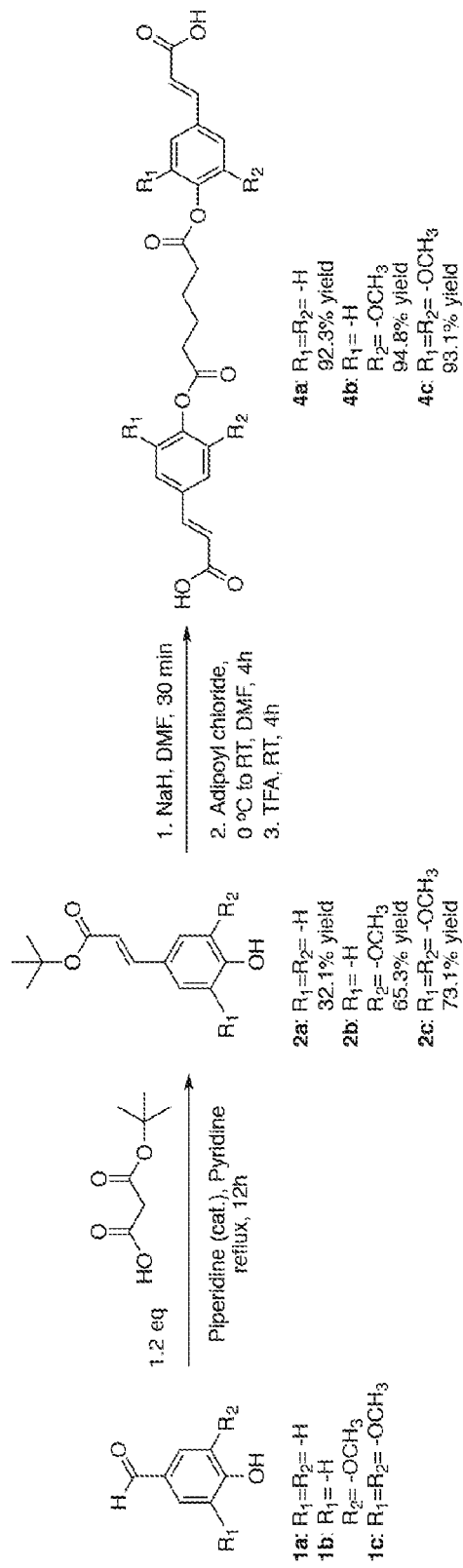
FIG. 11 shows a schematic for the synthesis of monolignol-based carboxylic acid ester dimers from precursor aldehydes in three steps via Knoevenagel condensation, dimerization with adipoyl chloride, and deprotection with trifluoroacetic acid, in accordance with one or more embodiments of the invention.

Petroleum-based polymers are the majority of commodity polymeric materials currently on the market, despite the decline of petroleum reserves. While some bio-based polymers, such as polylactide (PLA), polyhydroxyalkanoates (PHA), and thermoplastic starch, have been developed and are produced commercially [39], there are only a few examples of well-defined, scalable, aromatic-aliphatic polymers from plant-based sources [40-42]. To add to this new class of aromatic-aliphatic materials, we sought to utilize monolignols as a scaffold for polymer synthesis. In particular, we were interested in developing a series of poly(ester-amide)s due to their thermo-mechanical stability and degradability, which could increase their potential as a replacement for current commodity materials. Three monolignol-based carboxylic acid ester dimers were generated in three steps from the precursor aldehyde (FIG. 11).

Two dimers, starting from either 4-hydroxybenzaldehyde [37] or vanillin [38], had been previously reported by Ouimet et al., however we were unable to replicate the reported one-pot synthesis of 2a and 2b from Meldrum's acid in high yield. Instead, we isolated tert-butyl malonate, as reported by Smith et al. [36], prior to the Doebner-modified Knoevenagel condensation to form 2a, 2b, and 2c. While this condensation reaction was generally low yielding, the increasing degrees of methoxy-substitution increased the yield significantly. Additionally, previous reports required significant excess of the malonate (as high as 2.5 equivalents) for the Knoevenagel condensation, but we obtained similar yields when lowering the quantity of tert-butyl malonate to 1.2 equivalents. After isolation of each cinnamic tert-butyl ester monomer, the sodium salt of each monomer was generated in situ and then dimerized via a salt metathesis reaction with adipoyl chloride to afford protected dimers 3a, 3b, and 3c. The dimers were then deprotected, in near quantitative yield, with trifluroroacetic acid (TFA) to yield the dicarboxylic acid monomers 4a, 4b, and 4c. The reaction time for this deprotection had to be closely monitored and optimized, as the ester dimer could also be cleaved under the deprotection conditions.

Poly(Ester-Amide) Synthesis

Inspired by work by Kwolek and Morgan [43], we sought to generate a series of aromatic-aliphatic poly(ester-amide)s from monolignol-based acid chloride ester dimers via interfacial polymerization. Interfacial polymerization is a useful polymerization technique as it is usually done under mild reaction conditions, only requires short polymerization times, is less influenced by impurities, and does not require a strict adherence to stoichiometry [44]. The largest limitation to this polymerization method is the possibility of acid chloride hydrolysis, which will limit polymerization and decrease both the molecular weight and yield of any polymer generated. However, due to the hydrophobicity of our aromatic monolignol-based acid chloride ester dimer, we believed the hydrolysis side-reaction would be minimal and not greatly affect the polymerization reaction. We first attempted to draw a single fiber from the interface, similar to the *Nylon Rope Trick* [43], but the poly(ester-amide)s formed proved to be too brittle to permit this. Additionally, allowing the poly(ester-amide) to form as a film at the interface led to low conversion and low molecular weight polymers. During polymerization, the poly(ester-amide)s rapidly precipitated from solution, limiting their ability to react and generate high molecular weight polymers [45]. To eliminate solubility and brittleness issues, the solution was rapidly stirred during the interfacial polymerization reaction to maximize surface area and eliminate mechanical dependence on polymer formation.

Figure 12:
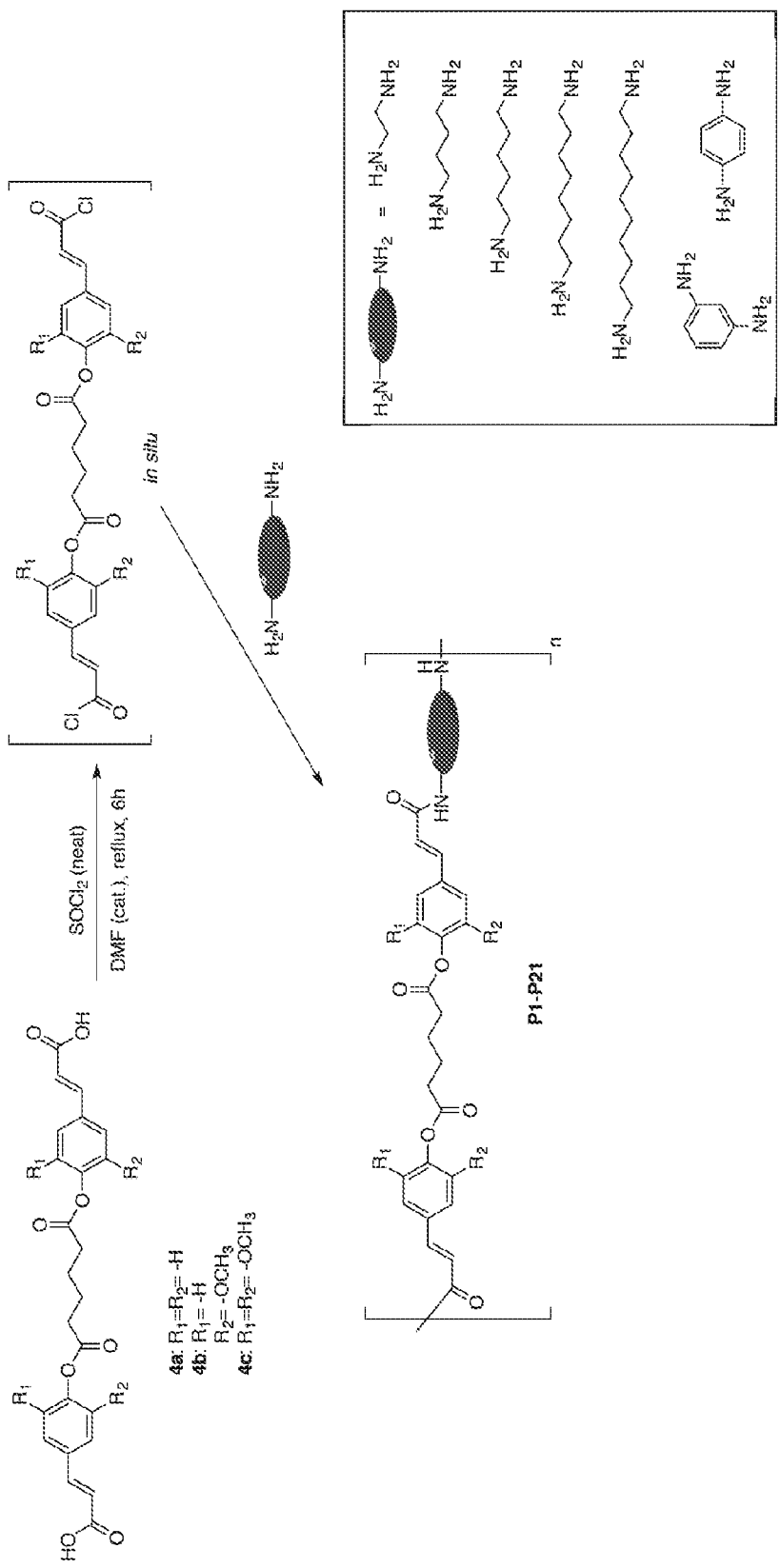
FIG. 12 shows a schematic for the interfacial polymerization of poly(ester-amide)s via monolignol-based diacid chloride monomers and seven different diamines, in accordance with one or more embodiments of the invention.
Figure 13:
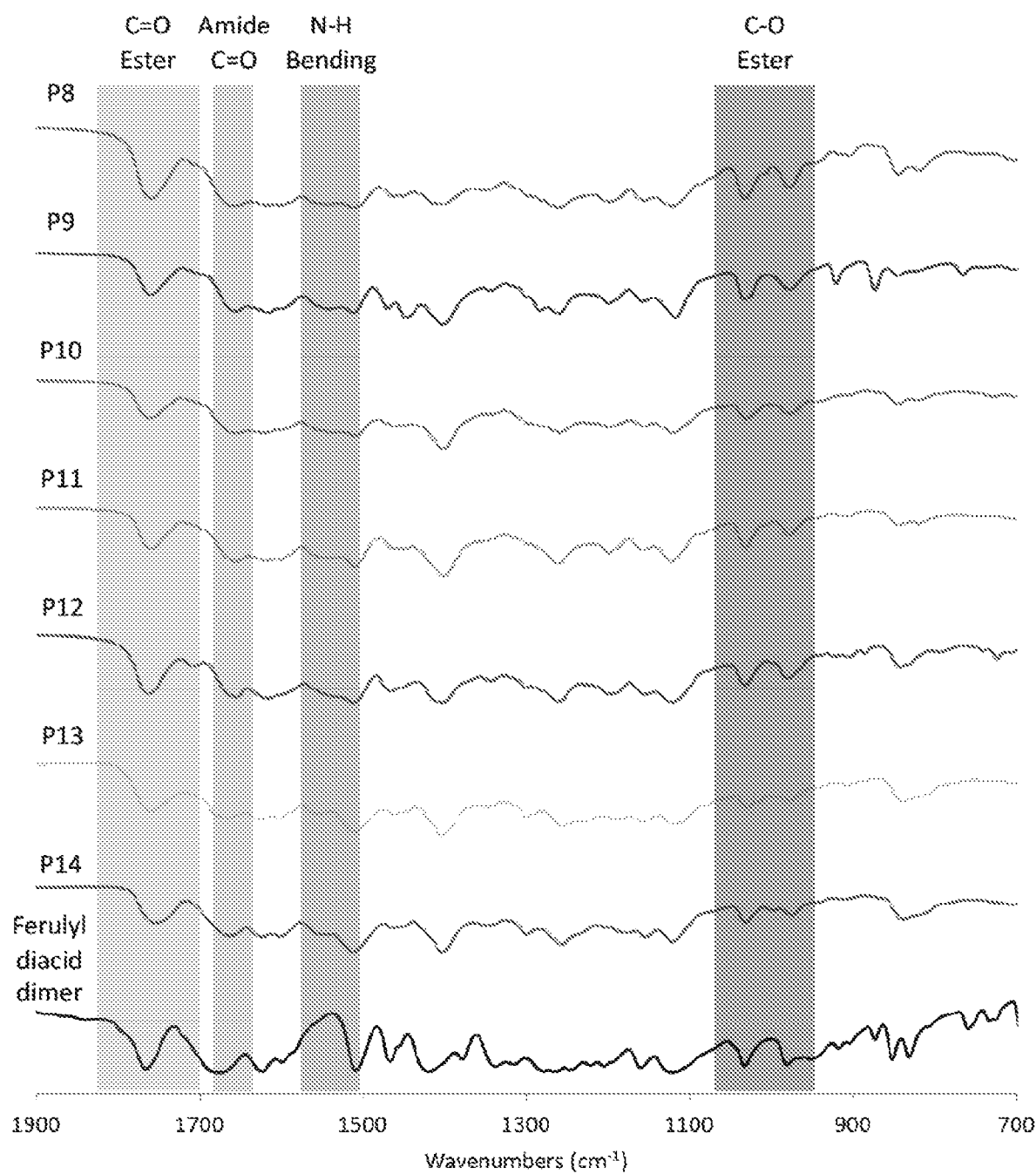
FIG. 13 shows the fingerprint region of IR spectra of ferulic-acid based poly(ester-amide)s (P8-P14) in comparison to the ferulic acid-based dimer, in accordance with one or more embodiments of the invention.

Interfacial polymerization was conducted with the desired aliphatic or aromatic diamine and desired monolignol-based diacid chloride ester dimer (FIG. 12). The diacid chloride dimer was generated in situ, via refluxing in thionyl chloride for six hours. After the reaction time was complete, volatiles were removed under reduced pressure and the diacid chloride ester dimer was used without further purification or characterization. The diacid chloride ester dimer was dissolved in distilled methylene chloride and added to a rapidly stirring, dilute sodium hydroxide solution containing the diamine. Poly(ester-amide)s were isolated as pale yellow powders from the biphasic solution. The resulting polymers were insoluble in standard organic solvents (i.e. acetone, diethyl ether, tetrahydrofuran) and only sparingly soluble in N,N-dimethylformamide (DMF). For P1, P5, P9, P11, P12, P16, and P20, more than 50% of the polymer sample was insoluble in DMF after 24 hours, with some polymers featuring insolubility as high as 76.3% (P20). The other polymers in the series were slightly more soluble, mostly between 50 and 35% insoluble after 24 hours. This insolubility affected the ability to perform standard solution phase characterization and limited characterization to solid-phase techniques. Formation of amide linkages was confirmed by IR spectroscopy, with the shift of the carboxylic acid C=O stretch to lower wavenumbers (1665-1650 cm$^{-1}$) with amide bond formation and the appearance of N—H bending (1540-1550 cm$^{-1}$), as seen in FIG. 13. As expected, the C=O (1765-1750 cm$^{-1}$) and C—O stretches (1030-1025 cm$^{-1}$ and 980-975 cm$^{-1}$) from the dimer ester bonds remain largely unchanged between the dimer starting material and final polymeric product, confirming the dimer remains intact throughout the polymerization procedure.

Molecular Weight Characterization

As mentioned previously, the series of poly(ester-amide)s were insoluble in common organic solvents and only sparingly soluble in DMF, hindering the characterization of the resulting materials. While poly(ester-amide)s are generally considered more soluble than polyamides, they are also known to be largely insoluble in common organic solvents [46], depending on the polymeric structure. Due to the amount of polymeric material not soluble in DMF, we speculate that the poly(ester-amide)s produced could be of even higher molecular weight than those reported below. In general, the poly(ester-amide)s generated in this example were of moderate molecular weight (by GPC) and, as expected due to the polymerization method, featured moderate dispersity. As seen in Table 3, the number-average molecular weight ($M_n$) and weight-average molecular weight ($M_w$) of each polymer in the series varies greatly depending on the identity of both the monolignol-based ester dimer and the diamine linker.

TABLE 3

Molecular weight characterization of poly(ester-amide)s by gel permeation chromatography

| Polymer | Dimer | Diamine | $M_n^a$ | $M_w^a$ | $Ð^b$ |
|---|---|---|---|---|---|
| P1 | p- | Ethylene diamine | 8,580 | 16,490 | 1.92 |
| P2 | Coumaryl | 1,4-diaminobutane | 4,050 | 9,320 | 2.32 |
| P3 | | Hexamethylenediamine | 7,830 | 12,660 | 1.62 |
| P4 | | 1,8-diaminooctane | 9,500 | 11,730 | 1.24 |
| P5 | | 1,10-diaminodecane | 9,190 | 11,410 | 1.24 |
| P6 | | m-phenylenediamine | 18,770 | 54,540 | 2.90 |
| P7 | | p-phenylenediamine | 7,560 | 29,850 | 3.95 |
| P8 | Ferulyl | Ethylene diamine | 11,300 | 16,910 | 1.50 |
| P9 | | 1,4-diaminobutane | 16,710 | 28,430 | 1.70 |
| P10 | | Hexamethylenediamine | 16,280 | 29,440 | 1.81 |
| P11 | | 1,8-diaminooctane | 8,552 | 9,562 | 1.12 |
| P12 | | 1,10-diaminodecane | 9,280 | 15,020 | 1.62 |
| P13 | | m-phenylenediamine | 13,720 | 58,230 | 4.24 |
| P14 | | p-phenylenediamine | 11,880 | 24,561 | 2.07 |
| P15 | Sinapyl | Ethylene diamine | 18,450 | 36,700 | 1.99 |
| P16 | | 1,4-diaminobutane | 13,110 | 19,170 | 1.46 |
| P17 | | Hexamethylenediamine | 27,470 | 65,780 | 2.39 |
| P18 | | 1,8-diaminooctane | 17,010 | 31,420 | 1.84 |
| P19 | | 1,10-diaminodecane | 5,130 | 9,750 | 1.90 |
| P20 | | m-phenylenediamine | 8,170 | 25,460 | 3.12 |
| P21 | | p-phenylenediamine | 4,780 | 22,260 | 4.66 |

$^a$Determined by GPC, 10 mM LiBr in DMF, 40° C., 1.0 mL/min;
$^b Ð = M_w/M_n$

While the majority of the polymers generated were of moderate molecular weight, several polymers featured molecular weights lower than what would be typically expected utilizing interfacial polymerization. With the lack of any methoxy-substituents, p-coumaryl derivatives either precipitate more quickly from solution, generating polymers of lower molecular weight, or the isolate polymers feature drastically reduced solubility in DMF. Both scenarios would drastically lower the molecular weight observed by GPC. Polymers synthesized from 1,8-diaminooctane or 1,10-diaminodecane, regardless of the identity of the monolignol-based ester dimer, were typically of lower molecular weight, due to the reduced solubility of long aliphatic diamines in the basic aqueous solution. Reducing the amount of soluble diamine present in solution to react during polymerization likely reduced the molecular weight of the polymer generated.

Thermal Properties.

The thermal stability of the poly(ester-amide)s were examined using thermogravimetic analysis (TGA). Samples were heated from 30 to 800° C. at 10° C./min under nitrogen. All polymers featured good thermal stability, with the onset of decomposition (To) typically between 220 and 260° C. (Table 4). The high degree of thermal stability makes these materials likely candidates for melt processing. Most commercial thermoplastics are processed between 100 and 250° C., depending on their melting temperature [47]. While thermogravimetric analysis cannot identify the melting point of each polymer, the overall thermal stability of these materials is a key aspect to consider when selecting a processing method.

Figure 14:
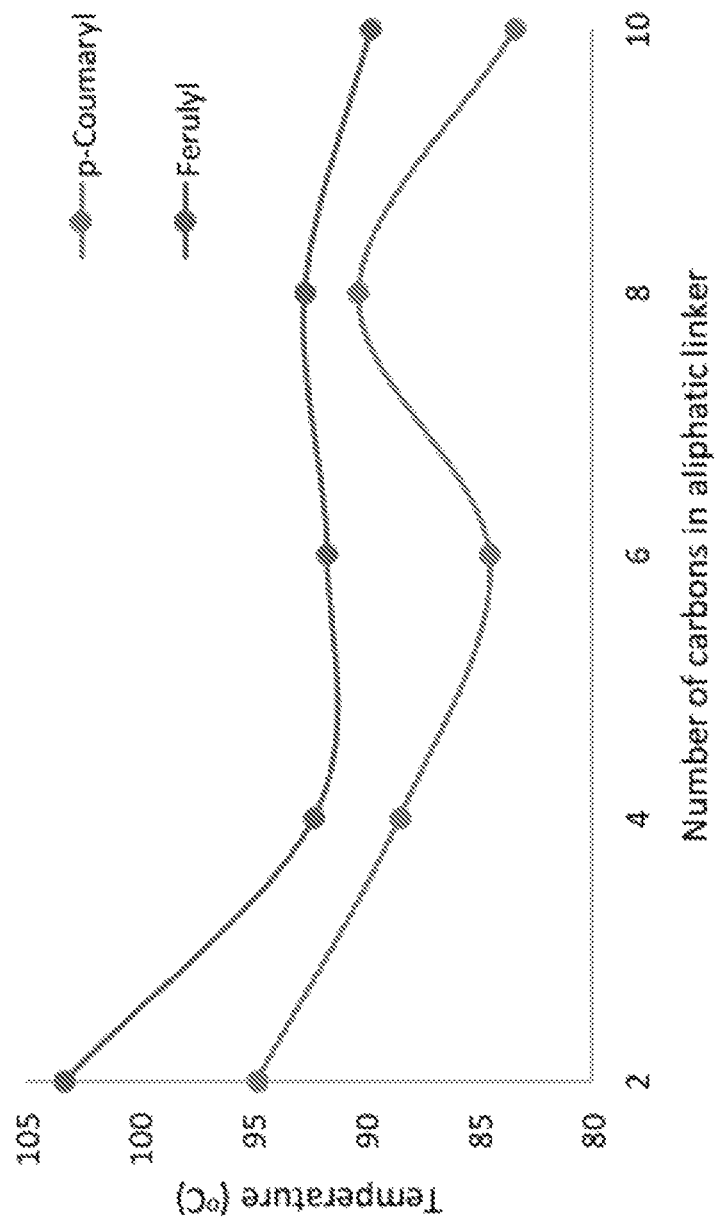
FIG. 14 show glass transition temperature ($T_g$) as a function of aliphatic linker length, in accordance with one or more embodiments of the invention.

Amorphous aliphatic polymers typically exhibit lower glass transition temperatures in comparison to aromatic amorphous polymers, due to high chain flexibility. Furthermore, the addition of bulky side groups to both aliphatic and aromatic amorphous polymers commonly increases the glass transition temperature, due to reduced chain flexibility. As the poly(ester-amide)s in this system feature both aromatic and aliphatic components as well as varying degrees of methoxy substitution, $T_g$ should increase with increasing aromatic content and substitution due to reduced backbone flexibility. While methoxy groups are hardly considered bulky substituents, this addition could affect the observed thermal properties of the poly(ester-amide)s. As shown in Table 4, the majority of this series of polymers is amorphous in nature, exhibiting $T_g$ between 64.7 and 138.2° C. Glass transition temperature should also decrease as the length of the aliphatic chain increases, due to increased flexibility of the polymer backbone. While the majority of the polymers follow this trend, there are several notable exceptions (FIG. 14). Poly(ester-amide)s containing 1,8-diaminooctane (P4, P11) exhibit increased glass transition temperatures. The eight carbon aliphatic spacer offers flexibility and optimal spacing between the amide and ester linkages to allow for increased intermolecular and intramolecular interactions between the chains. A similar effect was seen by Wang et al. in their synthesis of aromatic-aliphatic poly(ester-amide)s containing different length polyethylene glycol (PEG) spacers [48]. The polymers showed increasing $T_g$ as the length of PEG spacer increased, due to decreased molecular mobility with increased interactions. The addition of an aromatic linker, instead of an aliphatic linker, had varied effects on the glass transition temperature. P6, P7, P20, and P21 feature glass transition temperatures comparable to their aliphatic analogues. High glass transition temperatures associated with aromatic polyamides arise from interchain hydrogen bonding, which can be facilitated by π-π interactions. With these poly(ester-amide)s, the increased aromatic content provides structural rigidity, but does not have strong π-π interactions, limiting the formation of strong hydrogen bonding interactions. This can be seen even more directly in the effect of aromatic substitution on glass transition temperature. For example, P6, which is synthesized with m-phenylenediamine, has a $T_g$ 12.1° C. lower than P7, which is synthesized with p-phenylenediamine. The meta-substitution prevents the formation of additional π-π interactions and thus interchain interactions, lowering the observed glass transition temperature.

TABLE 4

Thermal characterization of poly(ester-amide)s by DSC and TGA

| Polymer | $T_g$ (° C.)$^a$ | $T_m$ (° C.)$^a$ | $T_{d5}$ (° C.)$^{b,c}$ | $T_{d10}$ (° C.)$^{b,d}$ | $T_{d25}$ (° C.)$^{b,e}$ |
|---|---|---|---|---|---|
| P1 | 94.5 | — | 255.4 | 297.8 | 371.9 |
| P2 | 88.5 | — | 251.2 | 307.1 | 369.5 |
| P3 | 84.5 | — | 264.2 | 314.4 | 410.3 |
| P4 | 90.3 | — | 294.1 | 324.8 | 394.6 |
| P5 | 83.4 | — | 260.2 | 302.1 | 357.6 |
| P6 | 79.3 | — | 233.3 | 300.0 | 358.3 |
| P7 | 91.4 | — | 252.5 | 321.6 | 364.5 |
| P8 | 103.3 | — | 266.9 | 286.6 | 340.3 |
| P9 | 92.3 | — | 255.8 | 287.9 | 343.9 |
| P10 | 91.7 | — | 249.5 | 298.3 | 353.8 |
| P11 | 92.7 | — | 253.9 | 283.0 | 330.8 |
| P12 | 89.8 | — | 255.4 | 297.8 | 371.9 |
| P13 | 119.7 | — | 231.2 | 290.1 | 356.0 |
| P14 | 125.9 | — | 240.1 | 273.4 | 332.9 |
| P15 | 95.9 | — | 235.6 | 272.9 | 322.7 |
| P16 | 71.3 | — | 246.9 | 285.1 | 378.6 |
| P17 | — | 63.6 | 256.3 | 277.4 | 340.9 |
| P18 | 84.3 | 127.9 | 252.1 | 291.8 | 376.9 |
| P19 | — | 141.9 | 222.4 | 279.5 | 396.1 |
| P20 | 91.3 | — | 221.8 | 254.6 | 385.8 |
| P21 | 67.8 | — | 203.0 | 220.1 | 303.8 |

$^a$Determined by DSC, scanned from −10 to 200° C. at 10° C./min;
$^b$Determined by TGA, heated from 30 to 800° C. at 10° C./min;
$^c$$T_{d5}$ = temperature at 5% mass loss;
$^d$$T_{d10}$ = temperature at 10% mass loss;
$^e$$T_{d25}$ = temperature at 25% mass loss While the degree of methoxy-substitution has little effect on the glass transition temperature, it affects the crystallinity of several poly(ester-amide)s. P17 and P19 exhibit only a single melting temperature ($T_m$) and no observable glass transition temperature, while P18 exhibits both a $T_m$ and a $T_g$. The dimethoxy-substitution of the sinapyl-acid based ester dimer in addition to the increased length of the aliphatic linkers allowed for the formation of a crystalline phase upon cooling from the first heating cycle in DSC. While the insolubility of the poly(ester-amide)s would render solution-phase processing difficult, the observed melting temperatures and high thermal stability should allow for heat processing with minimal decomposition. While only P17, P18, and P19 have clearly defined melting temperatures, the other polymers in this series could be expected to have a similar melting points for melt processing. The glass transition temperatures for the majority of the polymers are similar to commodity aromatic polymers, such as polyethylene terephthalate ($T_g$=70° C.) [49] or polystyrene ($T_g$=100° C.) [50], rendering these materials potentially suitable replacements for commodity materials.

Degradation of Poly(Ester-Amide)s

While aliphatic poly(ester-amide)s are typically capable of degradation under a variety of enzymatic and non-enzymatic conditions, wholly aromatic poly(ester-amide)s are generally considered less degradable than aliphatic analogues [51]. Due to the aromatic-aliphatic structure of our system, we were interesting in studying the degradation of our polymers in both neutral and acidic conditions. Additionally, varying the degree of methoxy substituents should affect the hydrophilicity and therefore the hydrolysis of each respective polymer. Due to the large number of polymers in this study, P15 to P21 (sinapyl acid-based) were compared to determine the role of diamine linker identity in degradation, while P1, P8, and P15 were compared to determine the role of degree of methoxy-substitution in degradation. As mentioned previously, all polymer samples feature moderate dispersity due to the non-controlled, bulk polymerization method utilized and therefore contain both higher and lower molecular weight fractions. Polymer samples were stirred in either pH 5.00 sodium acetate buffer or pH 7.04 water for 30 days, at a concentration of 10 mg/mL. 0.1 mL aliquots of each suspension were taken on day 7, 14, and 30, diluted to a concentration of 1 mg/mL with DMF before analysis by GPC. Due to the low signal intensity in each aliquot, traces were smoothed and normalized for comparison to non-decomposed polymers. As seen in FIGS. 15A-H, all samples did undergo decomposition at both pH 5 and 7, however some large molecular weight fractions remained even after 30 days and increased degradation was observed in the pH 7 solution.

Increasing the length of aliphatic linker decreased the amount of degradation in both solutions. This can be seen in the comparison of P15 (FIGS. 15A and 15B), synthesized with ethylene diamine, to P17 (FIGS. 15C and 15D), synthesized with hexamethylenediamine. The increased length of the aliphatic linker increases the hydrophobicity of the polymer, thus reducing its ability to undergo hydrolysis. The use of an aromatic diamine linker also shows increased resistance to hydrolysis for higher molecular weight fractions. As seen in FIG. 15E, the amount of lower molecular weight polymer in solution decreases relative to the higher molecular weight polymer, suggesting that the lower molecular weight fractions are more soluble and thus more readily undergo hydrolysis while the larger molecular weight polymers remain intact.

The degree of methoxy substitution affects solubility and thus the degree of hydrolysis. The ferulic acid (P8; FIGS. 15G and 15H) and p-coumaryl analogues (P1) featured minimal hydrolysis, in comparison to sinapyl-based polymers, even after 30 days in both acidic and neutral solutions. Overall, the degradation of the poly(ester-amide)s was moderate, suggesting that these materials would be appropriate for single use applications requiring good thermal properties and biodegradation. Other bio-based materials, such as poly(lactic acid), undergo hydrolysis too rapidly for widespread commercial use, which would not be a limitation of this system. If an increased rate of hydrolysis was desired, the aliphatic ester linkage could be replaced with an ethylene glycol linker to increase hydrophilicity and the rate of degradation, as seen in work by Ouimet et al. [52]

In this example, we have described the synthesis and characterization of a series of aromatic-aliphatic poly(ester-amide)s from monolignol-based ester dimers. The interfacial condensation polymerization of diamines and monolignol-based carboxylic acid ester dimers yielded a series of twenty-one polymers with varying molecular weights and dispersity. By selecting this method of polymerization and readily interchangeable structural components, we were able to rapidly generate a full series of polymers with tunable properties in a high-throughput manner. Further tuning of this system could yield additional materials with different properties. Moreover, this system is unique as it contains two unreacted double bonds per monolignol-based dimer, allowing it to be further modified, such as the addition of hydrophilic or hydrophobic groups, used as a backbone for graft-co-polymers, or cross-linked into a polymer network. Further research in our group will focus on the development of new applications and functionalization of this poly(ester-amide) system.

Example 4: Aromatic-Aliphatic Poly(Ether-Amides) from Monolignol-Based Ether Dimers Introduction The synthesis of bio-based polymers centers on the direct production of bio-polymers or bio-monomers from biological sources [53]. The demand for bio-based polymers has surged recently, due to declining petroleum reserves and an increased public awareness of the environmental issues surrounding the accumulation of petroleum-based plastic waste [54]. Commercial products produced from bio-based polymers are available, but generally feature weak thermo-mechanical properties in comparison to other commodity materials. Some bio-based materials exhibiting useful properties, similar to those of petroleum-based materials, have been produced but analogues of specialty polymers have yet to be developed. Specifically, few bio-based equivalents to commodity, aromatic polymers [55,56] have been produced, in stark contrast to the vast number of bio-based aliphatic polymeric materials available [57-59]. The difficulty in the production of these bio-based materials results from a lack of sources for biologically-derived aromatic monomers.

Lignin is the only naturally-occurring, aromatic polymer and is one of three components of lignocellulosic biomass. Unlike cellulose and hemicellulose, lignin is regularly isolated and discarded as a byproduct of several industrial processes. Polymerized in plant cell walls by the oxidative radical polymerization of p-hydroxycinnamyl alcohol monomers, lignin contains both ether and carbon-carbon linkages. Due to the uncontrolled polymerization method and functional groups present that are capable of chain transfer, the resulting polymeric structure is poorly defined and highly varying. In turn, the unpredictable polymeric structure makes utilizing lignin in polymers or composites difficult. However, as an aromatic polymer, lignin features commercially relevant properties, such as high strength and thermal stability [60-62]. While lignin itself is poorly defined, its monomers (monolignols) are well-defined, aromatic small molecules, making them ideal starting materials for polymer synthesis, without the difficulties associated with using lignin.

Figure 16:
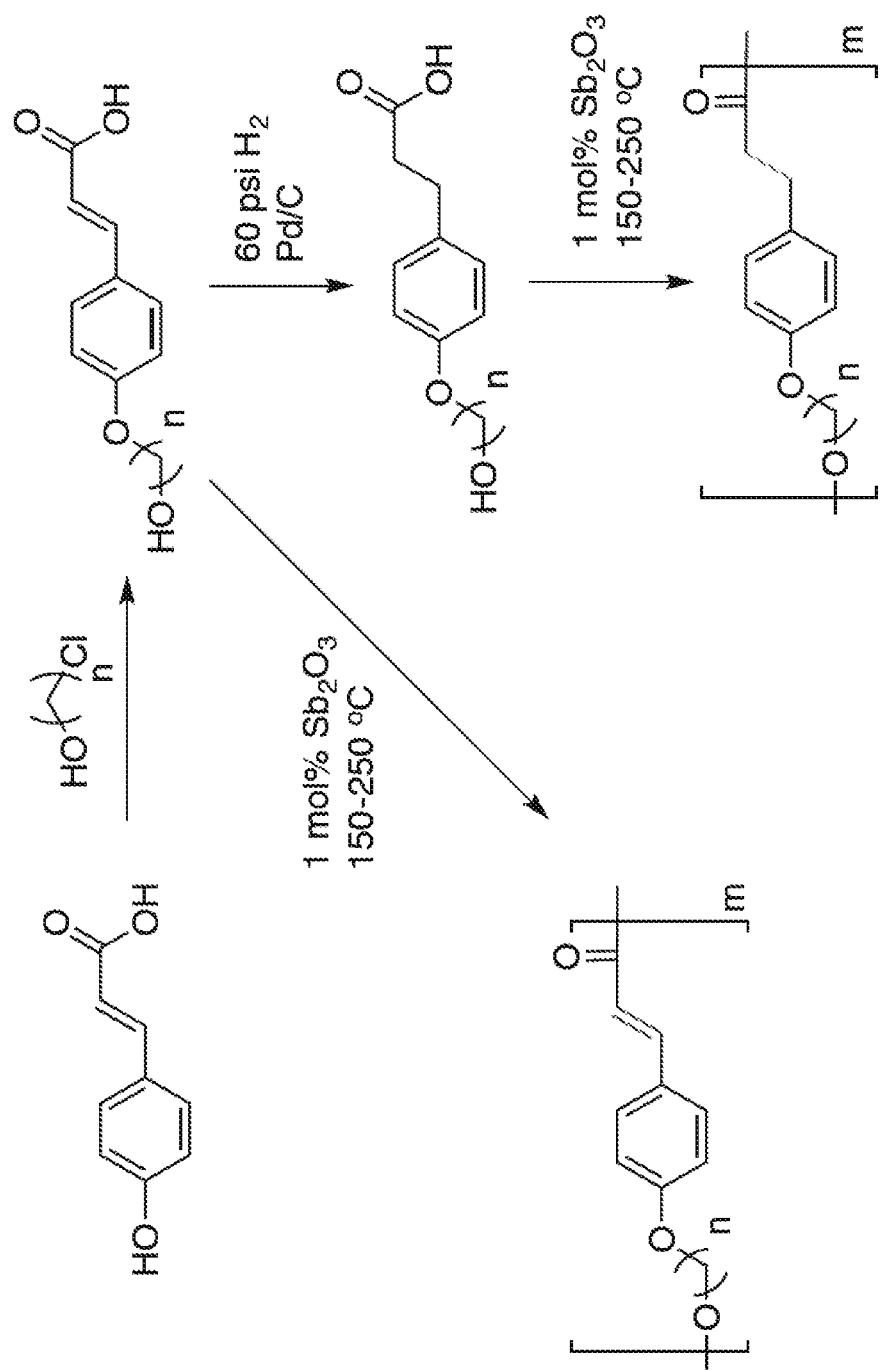
FIG. 16 shows a schematic of the synthesis and characterization of polyesters containing modified and unmodified monolignols by Nguyen et al.[15]

Modified monolignol-precursors have been used to synthesize polyesters [55,63,64], poly(ester-urethane)s [65,66], and poly(anhydride-ester)s. [67-69] Before incorporation, monolignols are commonly reduced to remove the unsaturation in their aliphatic side chain. A notable exception by Nguyen et al. features the comparison between polyesters with either modified or unmodified monolignols (FIG. 16) [70]. Copolymers from both monolignol variations were also synthesized. Retention of the double bond increased the glass transition temperature ($T_g$) of the resulting materials. $T_g$ of polymers containing unsaturated monomers was higher due to the limited rotational freedom about the sp$^2$ carbon-carbon bonds. Additionally, when unmodified monolignols were incorporated into copolymers in desired ratios, the $T_g$ could be tuned to match that of commodity materials.

Figure 17:
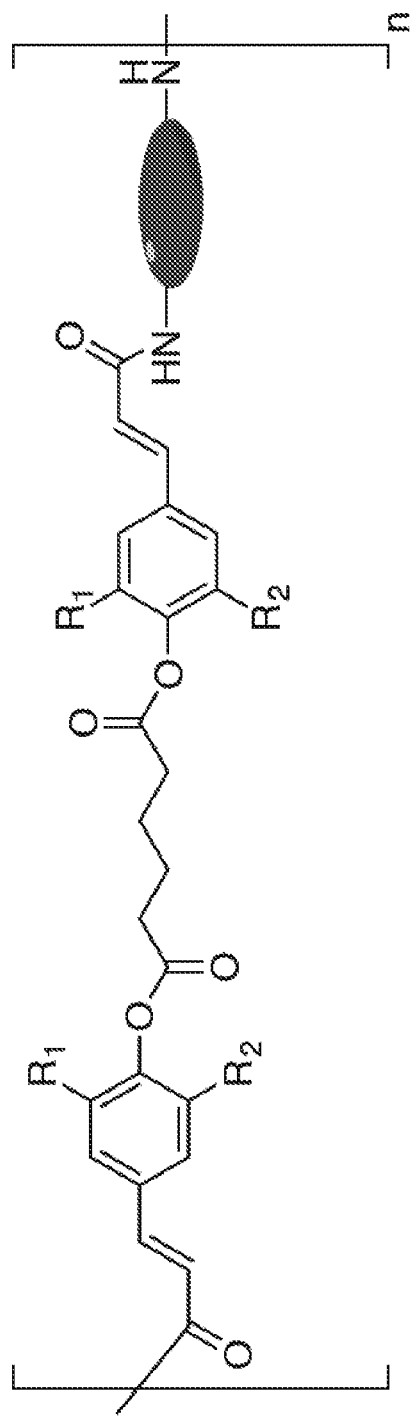
FIG. 17 shows a synthesized and characterized monolignol-based poly(ester-amide)s, in accordance with one or more embodiments of the invention.

Our group recently reported the synthesis and characterization of a series of monolignol-based poly(ester-amide)s as bio-based, biodegradable analogues to commodity aramids (FIG. 17). The aromatic-aliphatic poly(ester-amide)s were insoluble in common organic solvents, had moderate thermal stability, and were generally amorphous. Only three polymers in the series were crystalline, showing single melting temperatures on the second heating cycle in differential scanning calorimetry (DSC). The melting temperature of these polymers was between 70 and 140° C., which is within temperatures typically used for thermal processing. When considered in addition to the thermal stability of these polymers, poly(ester-amide)s synthesized in that study offer promise for use in melt processing applications. While these polymers had useful physical properties, they were subject to degradation over an extended period of time, due to hydrolysis of the ester linkages. Depending on the targeted application, the degradation pathway could limit these materials to only short-term applications and create issues with shelf-life and/or storage. As an expansion of our previous work, we were interested in the synthesis and characterization of a series of poly(ether-amide)s from monolignols, replacing the ester linker in the dimer with an ether unit, to eliminate degradation, improve the observed thermal properties, and improve polymer solubility.

Poly(ether-amide)s are polymers that feature both ether and amide linkages in their backbone. The most common example of these types of polymers are block co-polymers featuring rigid polyamide segments and flexible polyether segments, yielding materials with highly tunable properties [71]. Depending on both the identity and equivalents of each segment used, the resulting material can be tailored for use in a diverse range of applications. Aliphatic-aromatic poly (ether-amide)s are of particular interest, as adding ether linkages, pendant groups, or flexible linkers are mechanisms frequently used to increase the solubility and lower the $T_g$ of aromatic polyamides while maintaining their desirable thermal properties [72-76]. Garcia et al. studied the thermal and physical properties of a series of aliphatic-aromatic poly (ether-amide)s by adding short polyethylene glycol (PEG) chains between aromatic diamines [77,78]. The resulting properties varied, but control over $T_g$ and $T_m$ was achieved by varying the length of the aliphatic spacer. Additionally, the use of different aromatic substitutions (para versus meta) was shown to affect both $T_g$ and $T_m$. The use of meta-substituted linkers was shown to decrease the observed $T_g$ due to reduced interchain interactions.

Figure 18:
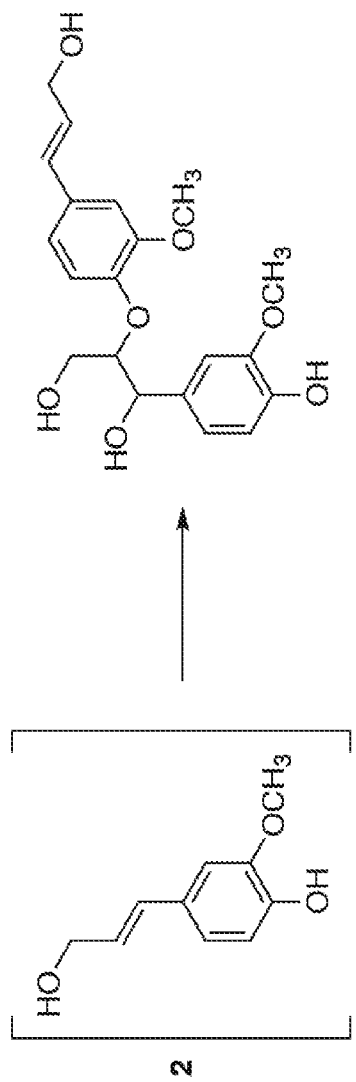
FIG. 18 shows a dimerization of coniferyl alcohol leading to the formation of a β-O-4 linkage, in accordance with one or more embodiments of the invention.

With this in mind, we synthesized a series of 21 poly (ether-amide)s from three monolignol-based carboxylic acid ether dimers and a series of seven aliphatic or aromatic diamines. While amide linkages are susceptible to hydrolysis over extended time scales, the degradation of these bonds is slow enough that amides are typically considered non-degradable in aqueous conditions. Additionally, the incorporation of an ether linkage into the monolignol dimer eliminates hydrolysis of the polymer backbone as a degradation mechanism, as ethers are only cleavable under harsh chemical conditions. β-O-4 ether linkages are the most common polymeric linkage found in native lignin (FIG. 18). The high degree of incorporation of this chemically-resistant bond aids in the observed chemical and thermal robustness of lignin. We speculate that the incorporation of a structurally similar linkage into the poly(ether-amide) backbone, should impart additional durability to the isolated materials. We also hypothesized that the incorporation of an ether linkage would not only lower the $T_g$ of the resulting materials with increased chain flexibility, but also improve polymer solubility by reducing interchain interactions.

Results and Discussion

Dimer Synthesis.

Figure 19:
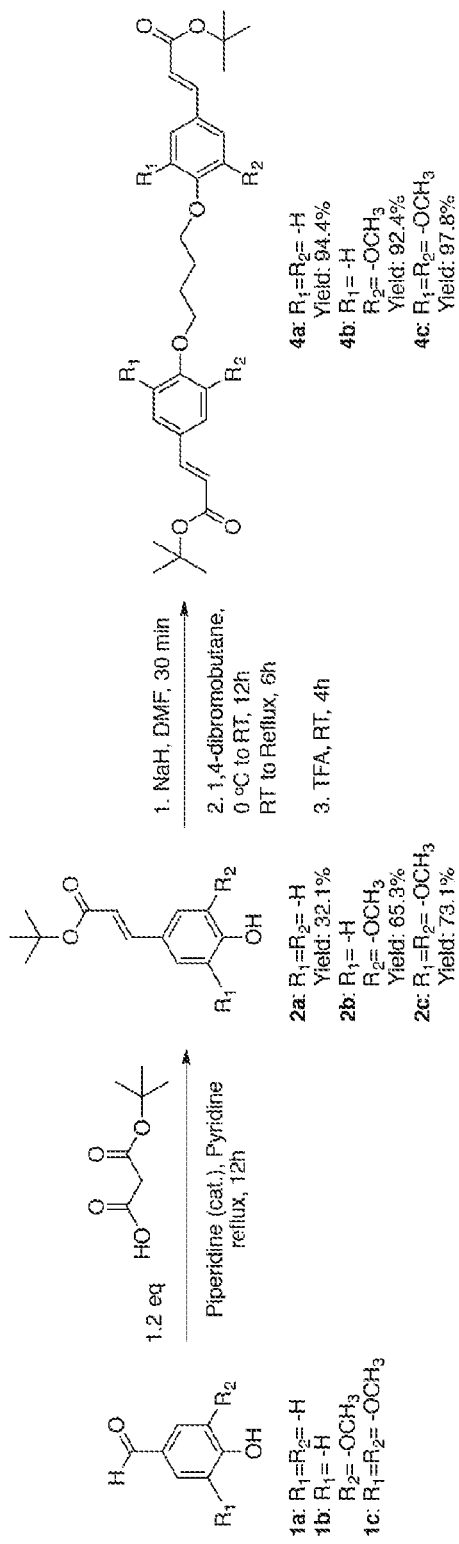
FIG. 19 shows a schematic of the synthesis of monolignol-based ether dimers from precursor aldehydes 1a, 1b, and 1c, in accordance with one or more embodiments of the invention.
Figure 20:
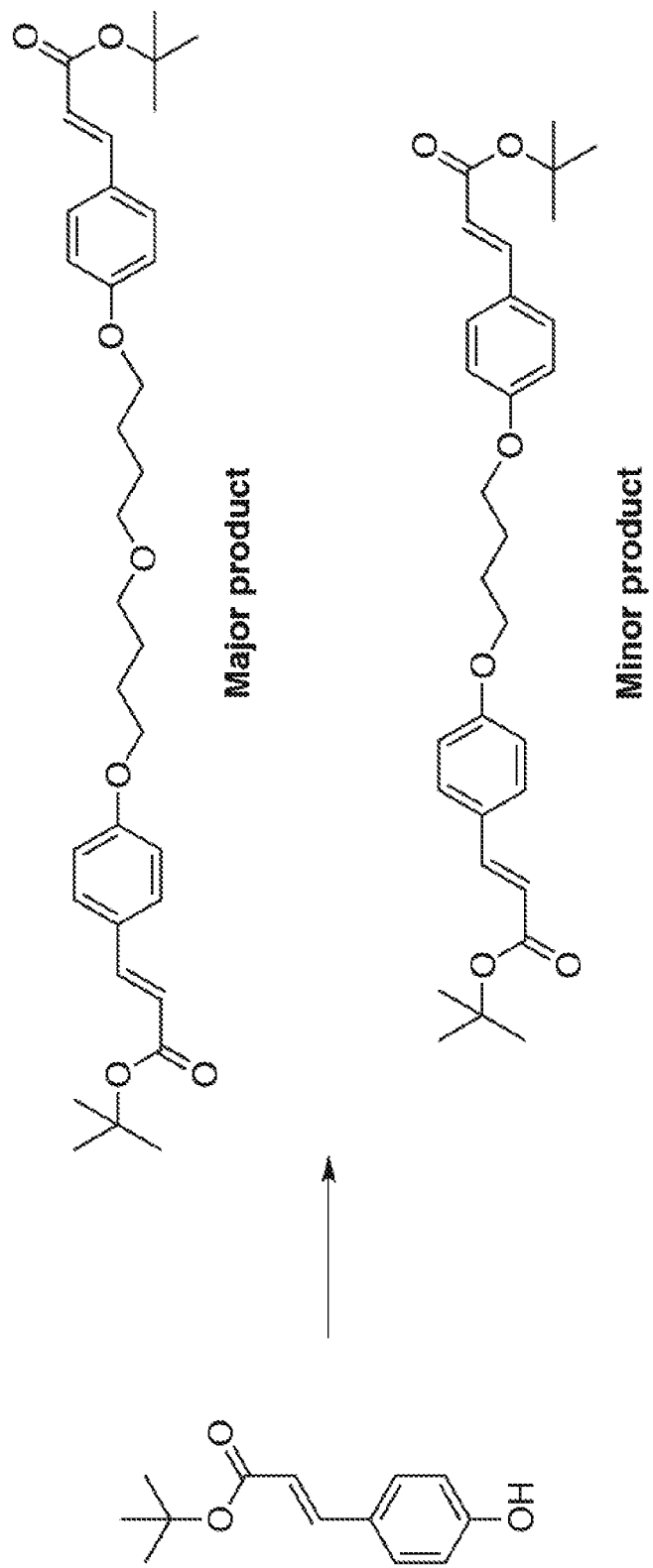
FIG. 20 shows a schematic of how non-optimized reaction conditions led to the formation of side products over the desired ether dimer.

Based on our previous work synthesizing a series of monolignol-based poly(ester-amide)s, we sought to create a set of monolignol-based poly(ether-amide)s that would be resistant to hydrolysis, feature increased solubility in common organic solvents, and exhibit lower melting and glass transition temperatures while retaining thermal stability. Towards this goal, we envisioned the synthesis of a series of monolignol-based ether dimers and their polycondensation with a series of diamine linkers to yield the desired polymers. A series of three monolignol-based ether dimers were synthesized in three steps from the precursor aldehydes (1a, 1b, and 1c). As shown in FIG. 19, the tert-butyl protected esters (2a, 2b, and 2c) were synthesized in one step from a Doebner-modified Knoevenagel condensation with tert-butyl malonate and 4-hydroxybenzaldehyde, vanillin, or 3,5-dimethoxy-4-hydroxybenzaldehyde, respectively. While the yields for this condensation reaction were lower than expected, the yield increased with increasing methoxy substitution. While the electronic effects of aldehyde substitution are rarely discussed for Knoevenagel condensation reactions, the inclusion of electron donating groups clearly affected the yield of the isolated enolates. The sodium salt of the protected ester monomers was synthesized with sodium hydride and then dimerized with 1,4-dibromobutane in N,N-dimethylformamide (DMF). The dimerization reaction did not proceed to completion at room temperature after 18 hours, so it was subsequently heated to reflux, in an attempt to increase conversion to the desired product. After heating to reflux for six hours, the reaction still did not reach full conversion, however increasing the reaction time led to the formation of undesired side products. Alternative methods (such as using a different base to deprotonate the protected ester monomers) were also attempted. These modifications increased the yield of side products (dimers with the addition of multiple ether linkers) rather than the desired ether dimer (FIG. 20). Despite the lack of full conversion, the desired ether dimers (3a, 3b, and 3c) were achieved in moderate yield (48.6% to 52.5%) after purification via column chromatography. Additionally, the unreacted tert-butyl ester monomers were also recovered via column chromatography, allowing their use in later reactions. The pure ether dimers were then deprotected using trifluroro-acetic acid (TFA), to yield 4a, 4b, and 4c, in nearly quantitative yield. Similar to the previously synthesized ester analogues, a key structural property of these ether dimers is the retention of the degree of unsaturation in their aliphatic side chain. The retention of this functionality should increase the thermal stability and glass transition temperature of the resulting poly(ether-amide)s [70]. We hypothesize that the balance between the rigidity associated with carbon-carbon double bond and the flexibility associated with ether linkages should generate a series of materials with tunable physical properties.

Poly(Ether-Amide) Synthesis.

In the literature, poly(ether-amide)s are commonly aliphatic block co-polymers synthesized by condensation reactions of aliphatic polyether and polyamide segments. While aliphatic materials are useful, they typically feature low thermal stability and glass transition temperatures, due to high chain flexibility and minimal interchain interactions. In contrast to these materials, we were interested in isolating aromatic-aliphatic poly(ether-amide)s, as bio-based mimics to aramids, such as Kevlar or Nomex. We hypothesized utilizing monolignol-based dimers would yield polymers with physical strength similar to aramids, while utilizing aliphatic diamine linkers would increase the solubility and processibility of the isolated polymers. Commercial aramids are typically produced via solution-phase methods, however due to difficulty identifying a common solvent, we utilized interfacial polymerization for poly(ether-amide) synthesis. Interfacial polymerization is an ideal polymerization technique as it does not require strict stoichiometric conditions, is less sensitive to impurities, requires short reaction times, and is commonly performed under mild reaction conditions [79]. Two immiscible monomer solutions, typically one aqueous and one non-aqueous, are prepared and carefully combined for polycondensation either by drawing a fiber from the interface, as utilized in the 'Nylon Rope Trick' [80], or as a precipitate from a vigorously stirring solution. Acid chloride hydrolysis is the largest limiting factor for this polymerization method, however due to the hydrophobic nature of the aromatic carboxylic acid ether dimer used, hydrolysis should be minimal. We initially attempted to draw fibers from the interface between the two solutions, but the poly(ether-amide)s produced were too brittle for isolation by this method. When polymers were allowed to form at the interface of the two solutions without stirring, the insolubility of the poly(ether-amide)s caused the resulting polymers to precipitate too rapidly to yield high molecular weight products. Due to these issues, we determined vigorous stirring was required during polycondensation to form high molecular weight poly(ether-amide)s [81].

Figure 21:
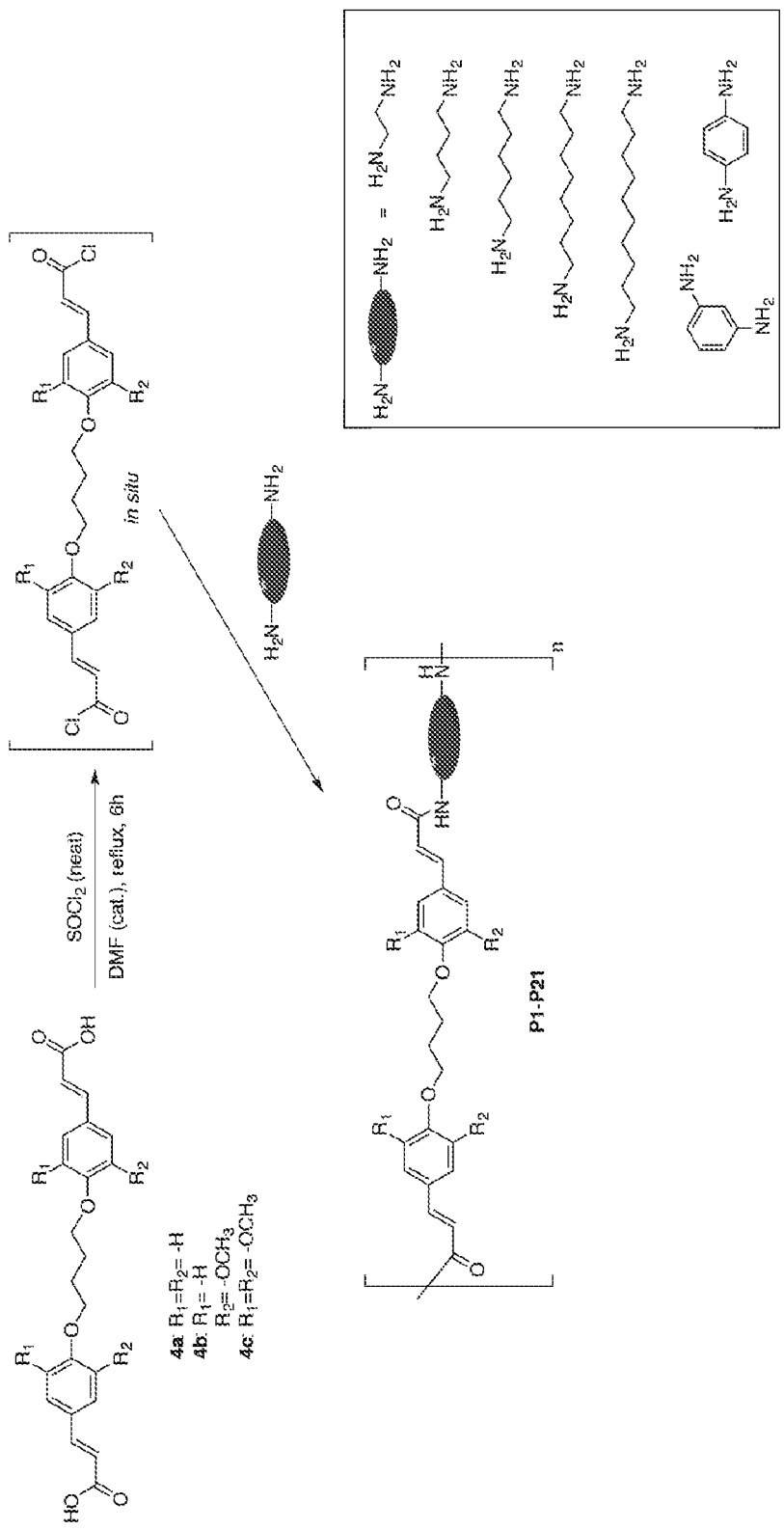
FIG. 21 shows a schematic of the synthesis of poly(ether-amides) from monolignol-based ether dimers and diamine linkers via interfacial polymerization, in accordance with one or more embodiments of the invention.
Figure 22:
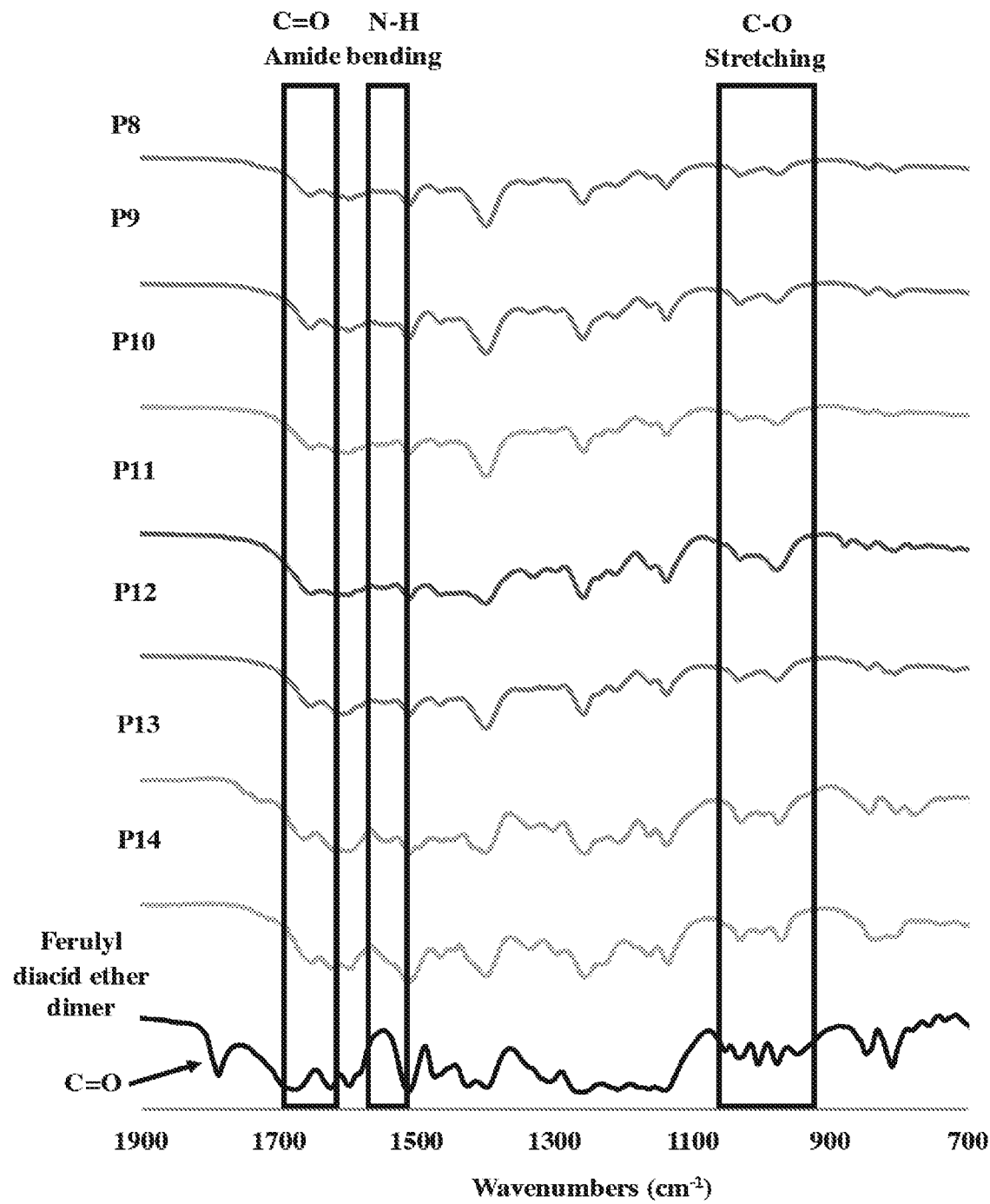
FIG. 22 shows an IR fingerprint region of P8-P14 and the corresponding ferulyl dimer starting material showing the formation of the amide linkage and presence of the ether linkage in the dimer, in accordance with one or more embodiments of the invention.
Figure 25:
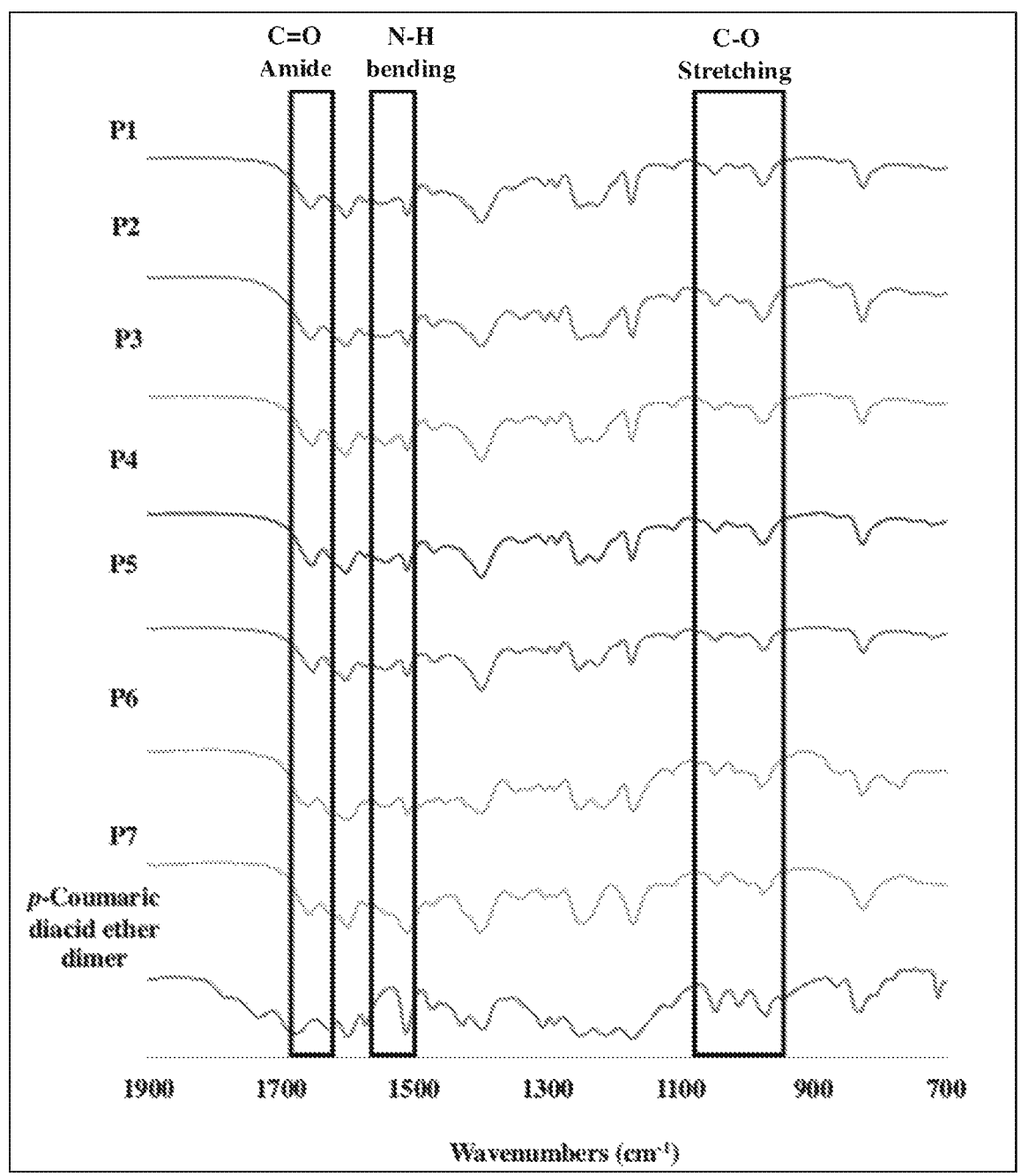
FIG. 25 shows the IR fingerprint region of p-Coumaryl-based poly(ether-amide)s (P1-P7), in accordance with one or more embodiments of the invention.
Figure 26:
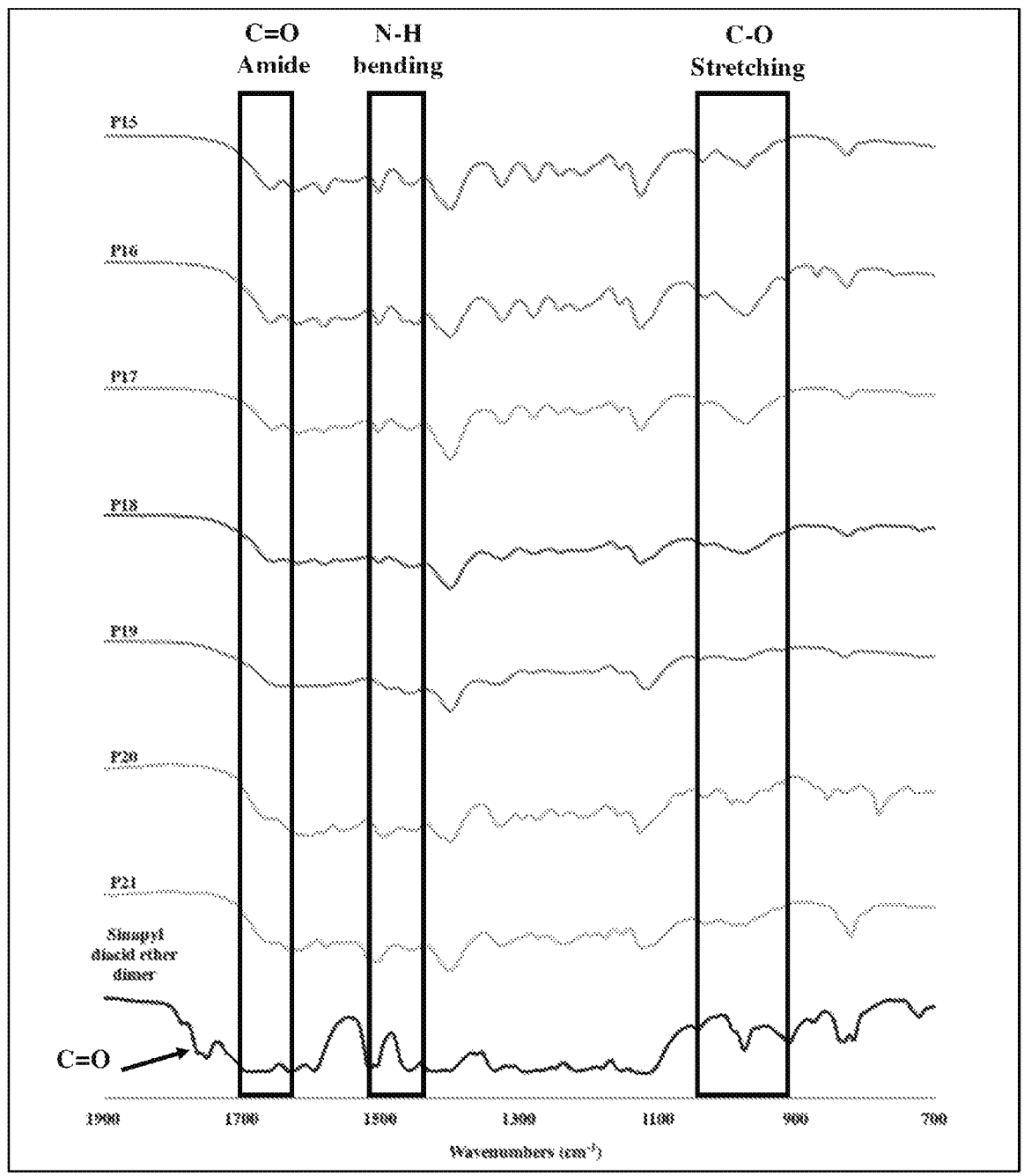
FIG. 26 shows the IR fingerprint region of Sinapyl-based poly(ether-amide)s (P15-P21), in accordance with one or more embodiments of the invention.
Figure 27:
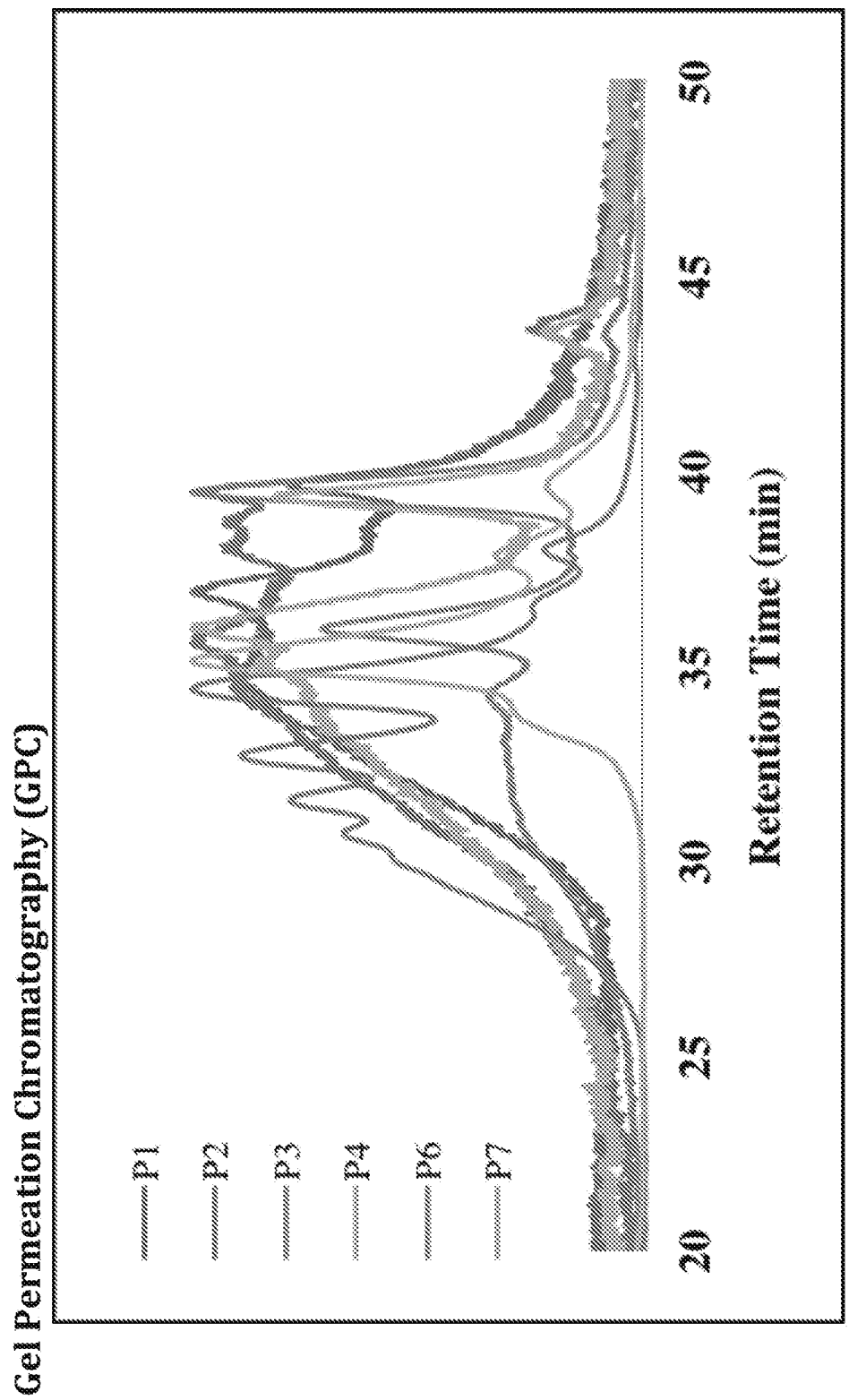
FIG. 27 shows the stacked GPC traces of p-Coumaryl-based poly(ether-amide)s (P1-P7), in accordance with one or more embodiments of the invention.
Figure 28:
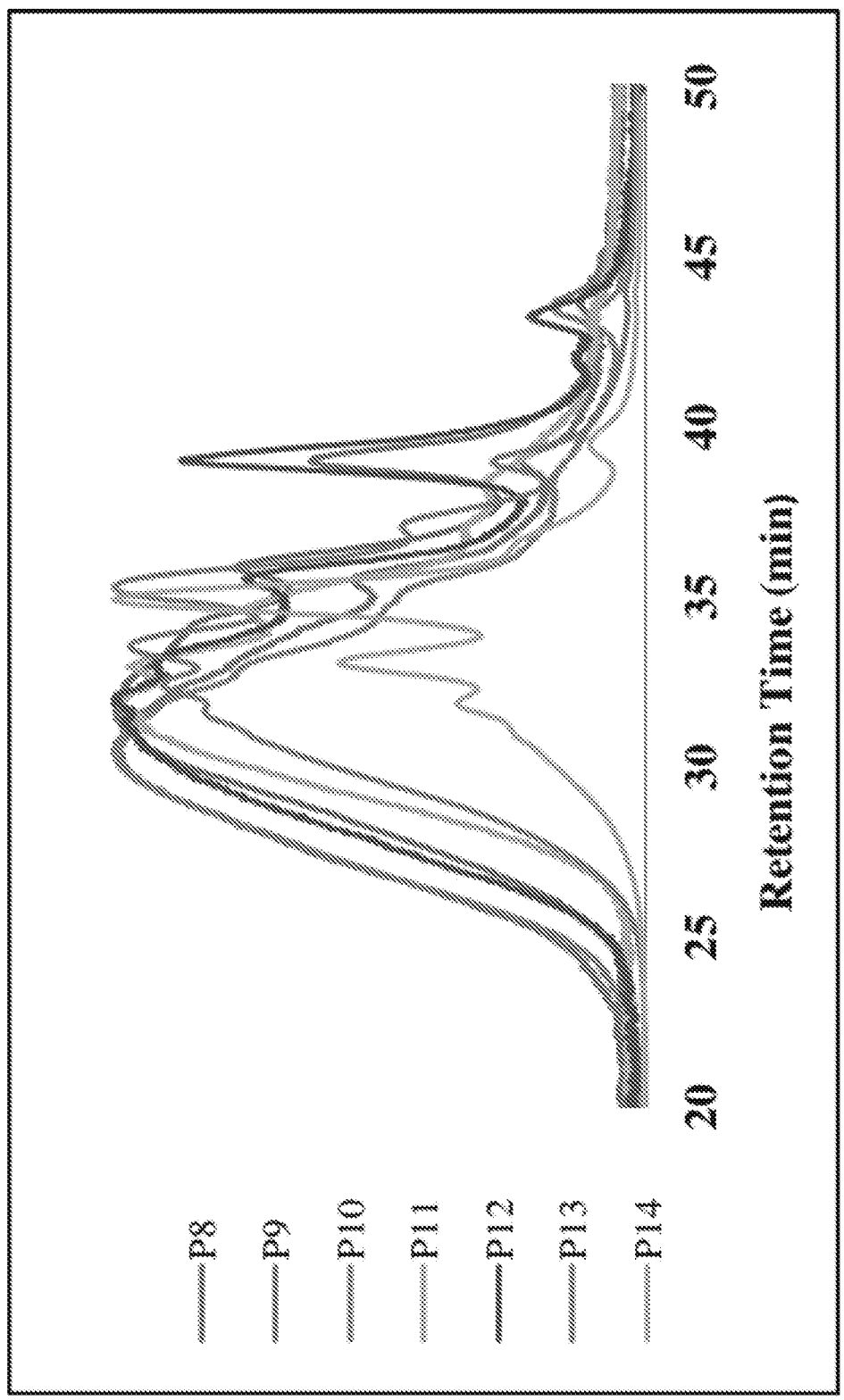
FIG. 28 shows the stacked GPC traces of ferulyl-based poly(ether-amide)s (P8-P14), in accordance with one or more embodiments of the invention.
Figure 29:
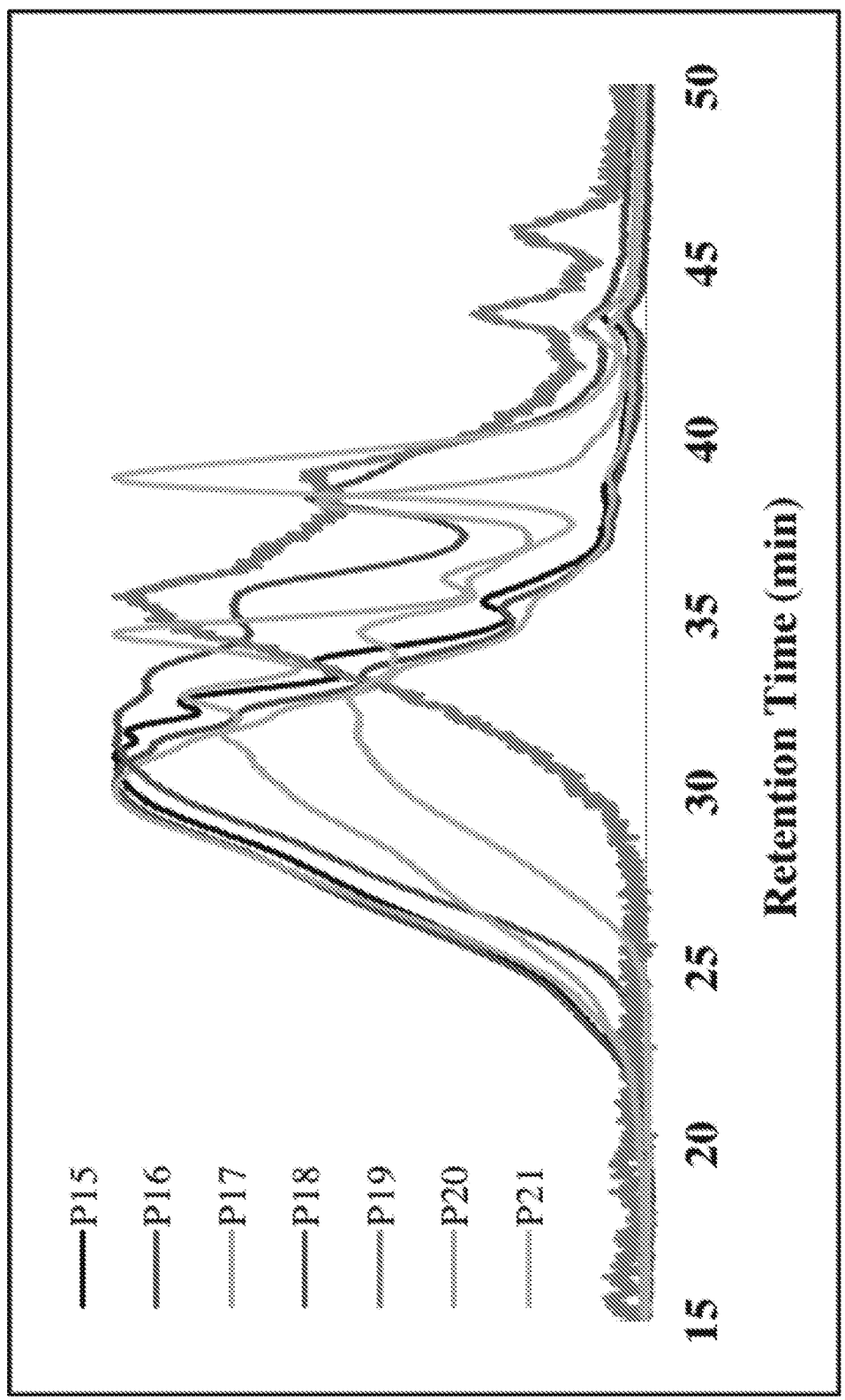
FIG. 29 shows the stacked GPC traces of sinapyl-based poly(ether-amide)s (P15-P21), in accordance with one or more embodiments of the invention.
Figure 30:
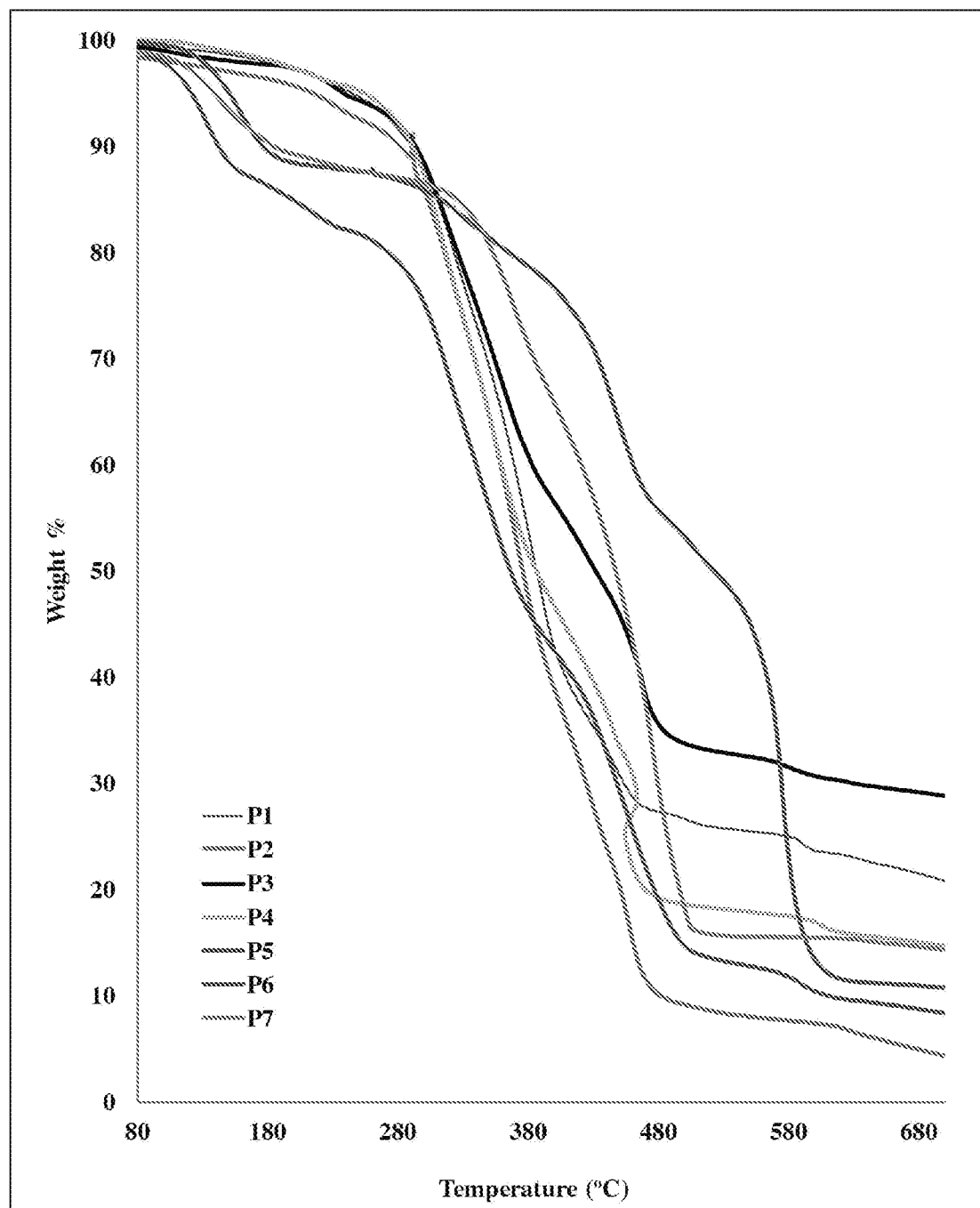
FIG. 30 shows the stacked TGA traces of p-Coumaryl-based poly(ether-amide)s (P1-P7), in accordance with one or more embodiments of the invention.
Figure 31:
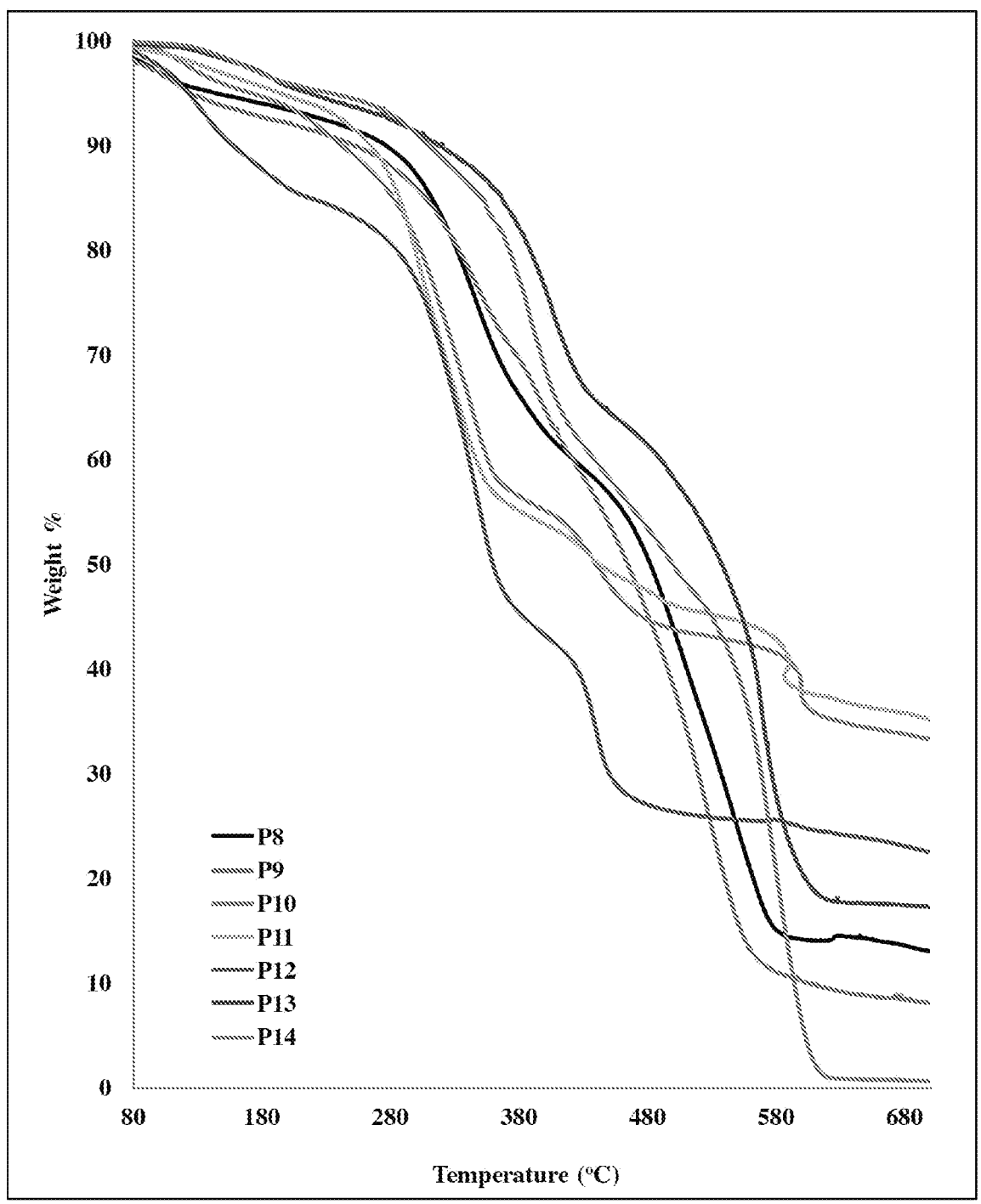
FIG. 31 shows the stacked TGA traces of ferulyl-based poly(ether-amide)s (P8-P14), in accordance with one or more embodiments of the invention.
Figure 32:
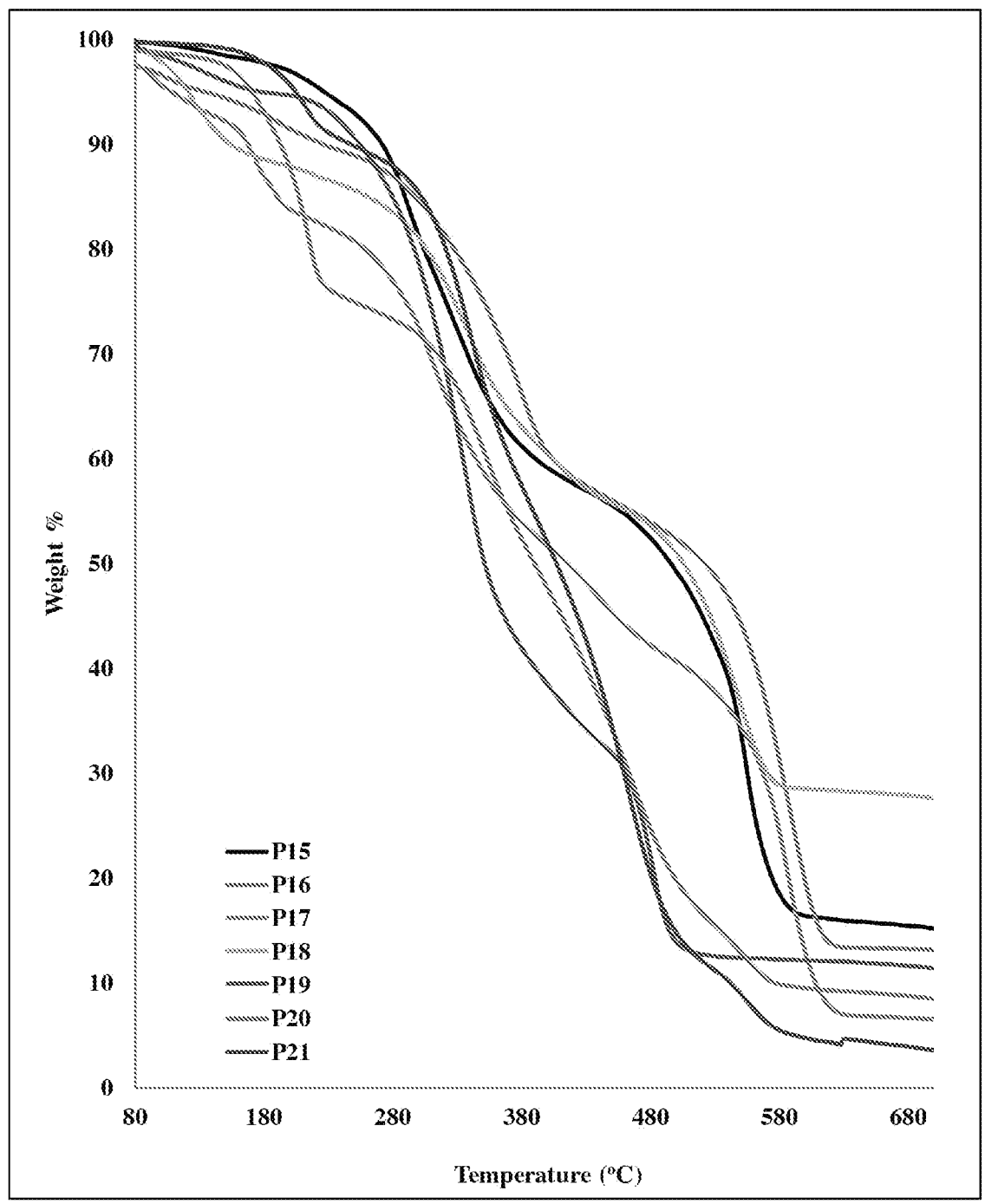
FIG. 32 shows the stacked TGA traces of sinapyl-based poly(ether-amide)s (P15-P21), in accordance with one or more embodiments of the invention.

Three acid chloride ether dimers were generated in situ by refluxing the carboxylic acid ether dimer in thionyl chloride for six hours. After removal of excess thionyl chloride, the acid chloride dimers were then dissolved in distilled dichloromethane and added to a dilute sodium hydroxide solution containing the desired diamine (FIG. 21). The condensation polymerizations yielded twenty-one different aromatic-aliphatic poly(ether-amide)s. The resulting polymers were insoluble in most common organic solvents, but were sparingly soluble in DMF at room temperature. Poly(ether-amide)s from p-coumaryl acid and aliphatic diamines (P1-P5) featured exceedingly limited solubility in DMF, due to the lack of methoxy substitution. Even after soxhlet extraction in DMF for 24 hours, P1-P5 remained largely intractable. Due to poly(ether-amide) insolubility, polymerization was confirmed (P1-P21) using FT-IR spectroscopy. As seen in FIG. 22, the C=O stretch in the ferulic acid carboxylic acid ether monomer shifted from ~1786 $cm^{-1}$ to 1650-1660 $cm^{-1}$ in P8-P14, confirming formation of the amide linkage. Additionally, N—H bending was seen from 1530-1560 $cm^{-1}$ and C—O stretching was seen from 1033-968 $cm^{-1}$, confirming formation of amide bonds as well as the retention of the ether dimer throughout the polymerization reaction. Similar stretching frequencies can be seen in both the sinapyl and p-coumaryl-based polymers (FIGS. 25 & 26), confirming formation of the series of poly(ether-amide)s.

Molecular Weight Characterization.

Figure 23:
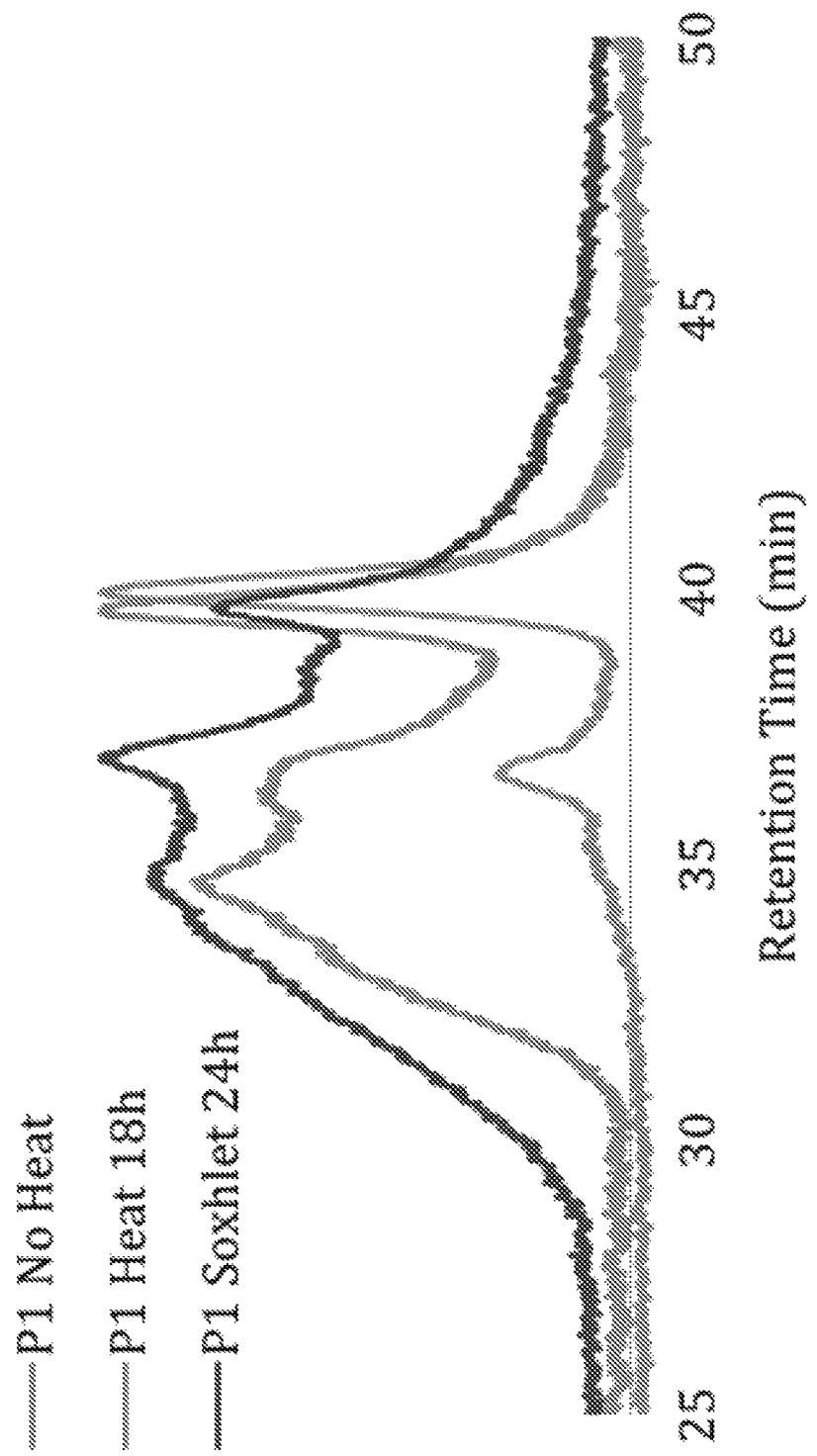
FIG. 23 shows GPC traces of P1 using different extraction techniques to improve high molecular weight polymer solubility, in accordance with one or more embodiments of the invention.

The number and weight average molecular weights ($M_n$ and $M_w$, respectively) of P1-P21 were determined using gel permeation chromatography (GPC) (Table 5). As mentioned previously, the isolated poly(ether-amide)s were sparingly soluble in DMF (Table 6), with a large fraction remaining intractable. This insolubility suggests that the molecular weights of the poly(ether-amide)s are higher than those determined by GPC, as GPC only characterizes the soluble fraction. This is clearly demonstrated in polymers P1-P5, which exhibited extremely low molecular weights by GPC ($M_n$: 3 to 6 kDa) when the polymers were added to DMF at room temperature. A similar effect was seen by Kwolek and Morgan, in the synthesis and characterization of aromatic-aliphatic polyamides [82]. In their work, polyamides containing aliphatic linkers less than nine carbons in length or aromatic units without functional groups, were insoluble in all common organic solvents, even DMF. Suspensions of the aromatic-aliphatic p-coumaryl-based polymers were heated using several different methods to improve the solubility of high molecular weight components. Boiling DMF was added to each polymer sample and stirred until the suspension had cooled to room temperature. After filtration, GPC traces showed that the addition of heated DMF resulted in a slight increase in the solubility of higher molecular weight fractions (FIG. 23). To determine if additional heating improved solubility, a 24-hour extraction with a soxhlet extractor was performed. Samples prepared via this method exhibited a significant increase in the observed molecular weight of P1-P4, as seen in Table 5. However, even after utilizing soxhlet extraction, molecular weights observed for P5 were still low. Limited molecular weights were also observed for ferulyl and sinapyl-based polymers synthesized with 1,10-diaminodecane, P12 and P19 respectively. Because P19 was the most soluble of the series, its overall molecular weight (soluble+insoluble) was likely lower than P5 or P12, which had larger insoluble fractions. One explanation for these lower molecular weights is the reduced solubility of 1,10-diaminodecane in the aqueous solution, as only lower molecular weight polymers were isolated for P5, P12, and P19. Similar results were seen in our previously studied poly(ester-amide) system.

TABLE 5

Molecular weight characterization of poly(ether-amide)s by gel permeation chromatography

| Polymer | Dimer | Diamine | $M_n{}^a$ | $M_w{}^a$ | $Đ^b$ |
|---|---|---|---|---|---|
| P1 | p-Coumaryl | Ethylene diamine | 3,700 | 5,060 | 1.37 |
|  |  |  | $6,740^c$ | $11,020^c$ | $1.64^c$ |
| P2 |  | 1,4-diaminobutane | 3,950 | 5,680 | 1.44 |
|  |  |  | $5,620^c$ | $15,780^c$ | $2.80^c$ |
| P3 |  | Hexamethylenediamine | 6,330 | 9,240 | 1.46 |
|  |  |  | $6,280^c$ | $16,500^c$ | $2.62^c$ |
| P4 |  | 1,8-diaminooctane | 6,410 | 9,130 | 1.42 |
|  |  |  | $8,110^c$ | $38,360^c$ | $4.73^c$ |
| P5 |  | 1,10-diaminodecane | 3,650 | 4,380 | 1.20 |
|  |  |  | $4,060^c$ | $5,130^c$ | $1.26^c$ |
| P6 |  | m-phenylenediamine | 15,210 | 21,800 | 1.43 |
| P7 |  | p-phenylenediamine | 7,690 | 9,460 | 1.23 |
| P8 | Ferulyl | Ethylene diamine | 12,780 | 24,830 | 1.94 |
| P9 |  | 1,4-diaminobutane | 18,490 | 37,470 | 2.03 |
| P10 |  | Hexamethylenediamine | 19,420 | 38,510 | 1.98 |
| P11 |  | 1,8-diaminooctane | 13,870 | 21,900 | 1.58 |
| P12 |  | 1,10-diaminodecane | 12,800 | 26,630 | 2.08 |
| P13 |  | m-phenylenediamine | 12,920 | 20,080 | 1.55 |
| P14 |  | p-phenylenediamine | 12,220 | 16,430 | 1.34 |
| P15 | Sinapyl | Ethylene diamine | 26,640 | 47,560 | 1.79 |
| P16 |  | 1,4-diaminobutane | 28,270 | 51,060 | 1.81 |
| P17 |  | Hexamethylenediamine | 28,630 | 49,050 | 1.71 |
| P18 |  | 1,8-diaminooctane | 12,160 | 26,300 | 2.16 |
| P19 |  | 1,10-diaminodecane | 7,550 | 10,600 | 1.40 |
| P20 |  | m-phenylenediamine | 14,580 | 34,730 | 2.38 |
| P21 |  | p-phenylenediamine | 8,430 | 19,290 | 2.29 |

$^a$Determined by GPC, 1.0 mLmin$^{-1}$, 0.01M LiBr in DMF;
$^bĐ = M_w/M_n$;
$^c$Molecular weight determined after soxhlet extraction, 24 h, with 0.01M LiBr in DMF Generally, the poly(ether-amide)s exhibited weight average molecular weights ($M_w$) between 20 and 40 kDa and dispersities between 1.5 and 2.2. The highest molecular weight polymers were produced from sinapyl acid-based ether dimers, likely due its increased solubility with the dimethoxy substitution pattern. The broad diversity of polymers obtained show the effectiveness of this polymerization method for the rapid generation of a series of polymers with tunable properties. Based on the polymerization method used, the dispersity of the resulting materials is not well controlled. However, values obtained are within acceptable values for commercial applications, suggesting that this polymerization method could be appropriate for use in an industrial setting.

TABLE 6

Insolubility of poly(ether-amide)s in DMF after 24 h$^a$

|  | Polymer | Wt % insoluble$^a$ |
|---|---|---|
| p-coumaryl | P1 | 62.3 |
|  | P2 | 32.0 |
|  | P3 | 38.5 |
|  | P4 | 47.5 |
|  | P5 | 52.5 |
|  | P6 | 23.3 |
|  | P7 | 46.6 |
| ferulyl | P8 | 49.7 |
|  | P9 | 67.4 |
|  | P10 | 18.5 |
|  | P11 | 74.3 |
|  | P12 | 57.3 |
|  | P13 | 25.4 |
|  | P14 | 26.7 |
| sinapyl | P15 | 27.2 |
|  | P16 | 64.8 |
|  | P17 | 45.8 |
|  | P18 | 39.2 |
|  | P19 | 45.2 |
|  | P20 | 76.3 |
|  | P21 | 40.8 |

$^a$1.0 mL of 10 mM LiBr in DMF was added to weighed polymer samples (10 mg) and allowed to sit at room temperature for 24 h. Solvent was decanted and the residual solid was dried in a vacuum oven overnight. Solid was weighed to determine wt % insoluble.

Thermal Properties.

The thermal behavior of polymers P1-P21 were studied using both differential scanning calorimetry (DSC) and thermogravimetric analysis (TGA). Generally, aromatic polymers exhibit higher glass transition temperatures ($T_g$) than aliphatic polymers due to a lack of rotation about bonds between aromatic monomers, in comparison to aliphatic sp$^3$ bonds. This lack of rotational freedom causes reduced chain mobility and backbone flexibility. Additionally, with the inclusion of bulky side groups, $T_g$ should also increase, as these modifications cause decreased chain mobility by limiting rotation about bond in the backbone. As the polymers in this study feature both aromatic and aliphatic components, as well as varying degrees of methoxy substitution, structural effects on $T_g$ are complex.

TABLE 7

Thermal characterization of poly(ether-amide)s by DSC and TGA

|  | Polymer | $T_g$ (° C.)$^a$ | $T_{d5}$ (° C.)$^{b,c}$ | $T_{d10}$ (° C.)$^{b,d}$ | $T_{d25}$ (° C.)$^{b,e}$ |
|---|---|---|---|---|---|
| p-coumaryl | P1 | 90.8 | 243.6 | 290.3 | 335.8 |
|  | P2 | 91.8 | 213.3 | 280.9 | 327.0 |
|  | P3 | 84.3 | 238.3 | 294.0 | 340.4 |
|  | P4 | 80.6 | 254.4 | 291.7 | 328.1 |
|  | P5 | 66.2 | 121.6 | 142.4 | 301.0 |
|  | P6 | 79.1 | 150.3 | 175.9 | 410.8 |
|  | P7 | 112.3 | 139.1 | 185.1 | 368.9 |
| ferulyl | P8 | 103.1 | 143.9 | 276.7 | 344.5 |
|  | P9 | 92.4 | 123.5 | 251.9 | 353.9 |
|  | P10 | 98.1 | 170.9 | 241.6 | 317.9 |
|  | P11 | 110.1 | 194.2 | 264.8 | 310.8 |
|  | P12 | 82.3 | 123.3 | 157.6 | 307.5 |
|  | P13 | 108.3 | 216.5 | 317.9 | 404.3 |
|  | P14 | 124.7 | 233.7 | 310.9 | 386.5 |
| sinapyl | P15 | 106.9 | 226.5 | 271.4 | 317.7 |
|  | P16 | 102.3 | 133.5 | 225.5 | 350.3 |
|  | P17 | 85.2 | 106.2 | 166.7 | 289.4 |
|  | P18 | 84.9 | 121.6 | 154.5 | 328.3 |
|  | P19 | 77.9 | 177.8 | 254.8 | 309.0 |

TABLE 7-continued

Thermal characterization of poly(ether-amide)s by DSC and TGA

| Polymer | $T_g$ (° C.)[a] | $T_{d5}$ (° C.)[b,c] | $T_{d10}$ (° C.)[b,d] | $T_{d25}$ (° C.)[b,e] |
|---|---|---|---|---|
| P20 | 84.8 | 170.8 | 192.8 | 248.8 |
| P21 | 81.1 | 204.8 | 247.4 | 333.7 |

[a]Determined by DSC;
[b]Determined by TGA;
[c]$T_{d5}$ = temperature at 5% mass loss;
[d]$T_{d10}$ = temperature at 10% mass loss;
[e]$T_{d25}$ = temperature at 25% mass loss All of the poly(ether-amide)s were shown to be amorphous by DSC, as only a single glass transition temperature ($T_g$) was observed. Due to high backbone flexibility, polyethers typically exhibit extremely low $T_g$. In contrast, the poly(ether-amide)s synthesized featured moderately high $T_g$, as seen in Table 7. The glass transition temperature ($T_g$) should decrease as the length of the aliphatic spacer increases due to increased chain mobility and backbone flexibility, while the utilization of aromatic diamines as linkers should increase the observed $T_g$. While these trends are generally seen throughout the series of isolated poly(ether-amide)s, there are also several significant exceptions.

Figure 24:
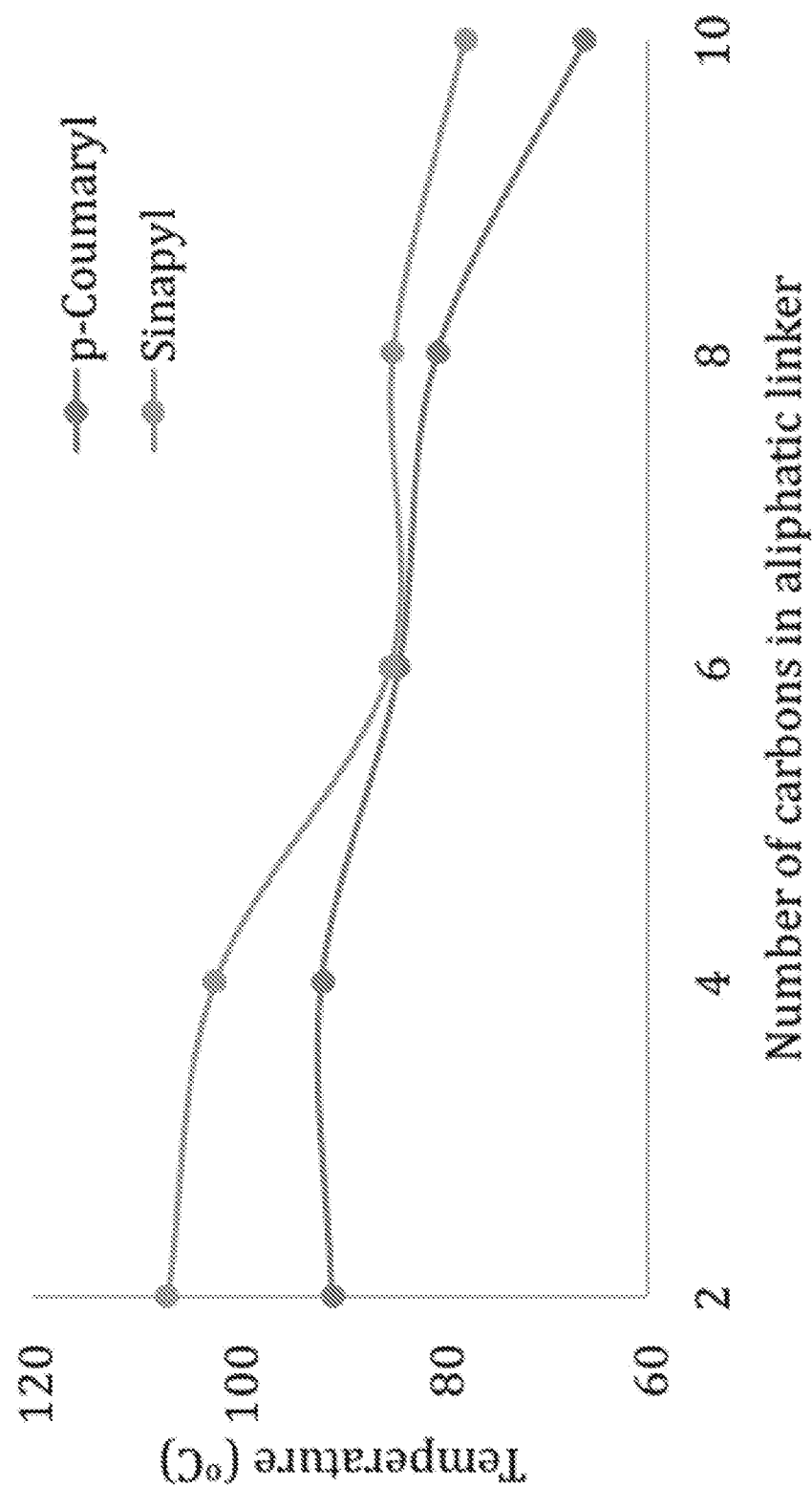
FIG. 24 shows glass transition temperature as a function of aliphatic linker length, in accordance with one or more embodiments of the invention.

As seen in FIG. 24, both the length of the aliphatic linker, as well as the identity of the monolignol dimer, have large effects on the observed $T_g$. The incorporation of substituted aromatic dimers (sinapyl-based dimers instead of p-coumaryl-based dimers), increases the observed $T_g$ by limiting the rotational flexibility of the polymer chains. As expected, $T_g$ generally increased with increasing degrees of methoxy substitution, as seen in the overall increase in $T_g$ between P1-P7 and P15-P21. Similarly to our previous study, poly(ether-amide)s with long aliphatic linkers (such as hexamethylenediamine, 1,8-diaminooctane, 1,10-diaminodecane) exhibited $T_g$ higher than expected, as seen in P10 and P11. These deviations in glass transition temperature likely occurred due increased chain interactions, which prevent polymer chain movement. Wang et al. saw a similar effect in the synthesis of poly(ether-amide)s with polyethylene glycol spacers [83]. As the length of the PEG spacer increased, the observed $T_g$ also increased due to increased interchain interactions. In addition to effects seen by the incorporation of longer aliphatic spacers, the substitution pattern of aromatic diamines also significantly affected the observed glass transition temperature. The use of m-phenylenediamine instead of p-phenylenediamine showed a decrease in the observed $T_g$, seen in a comparisons between P13 and P14. The meta-substitution pattern causes a non-linear structure, which will minimize π-π interactions and prevent the formation of strong hydrogen bonds between chains. In turn, the reduced interchain interactions cause a significant reduction in the observed $T_g$.

Molecular weight also played a significant role in the observed $T_g$ of the poly(ether-amide)s. Polymer chain ends are less dense than interchain units, exhibiting greater free volume. A larger concentration of chain ends in a polymer sample (by the presence of smaller molecular weight polymers or a greater fraction of smaller molecular weight polymers) will lower the observed $T_g$, as free volume is inversely proportional to glass transition temperature. With this in mind, a large fraction of smaller molecular weight polymers in a non-monodisperse sample can have effects similar to that observed with the addition of plasticizers. As exemplified by their higher dispersity, P9 and P12 feature an increased fraction of smaller molecular weight polymers, which yields lower glass transition temperatures than would expected based on the length of their linker and $T_g$ observed for other ferulyl-based polymers. As seen in Table 7, P11 featured a higher $T_g$ than P18. While both polymers are synthesized with 1,8-diaminooctane, P11 is synthesized with the ferulyl-based dimer (single methoxy substitution) and should feature a lower glass transition temperature than P18. However, P11 exhibits a weight-average molecular weight more than 5 kDa greater than P18. This difference in molecular weight, and thus decreased number of chain ends present, is responsible for the observed increase in $T_g$. Additionally, P18 is more polydisperse with a dispersity of 2.16, in comparison to P11 which features a dispersity of 1.58. The higher dispersity of this sample causes broadening of the glass transition, which may play a role in the observed decreased Tg, as glass transition temperature is defined as the midpoint of the glass transition.

Figure 33:
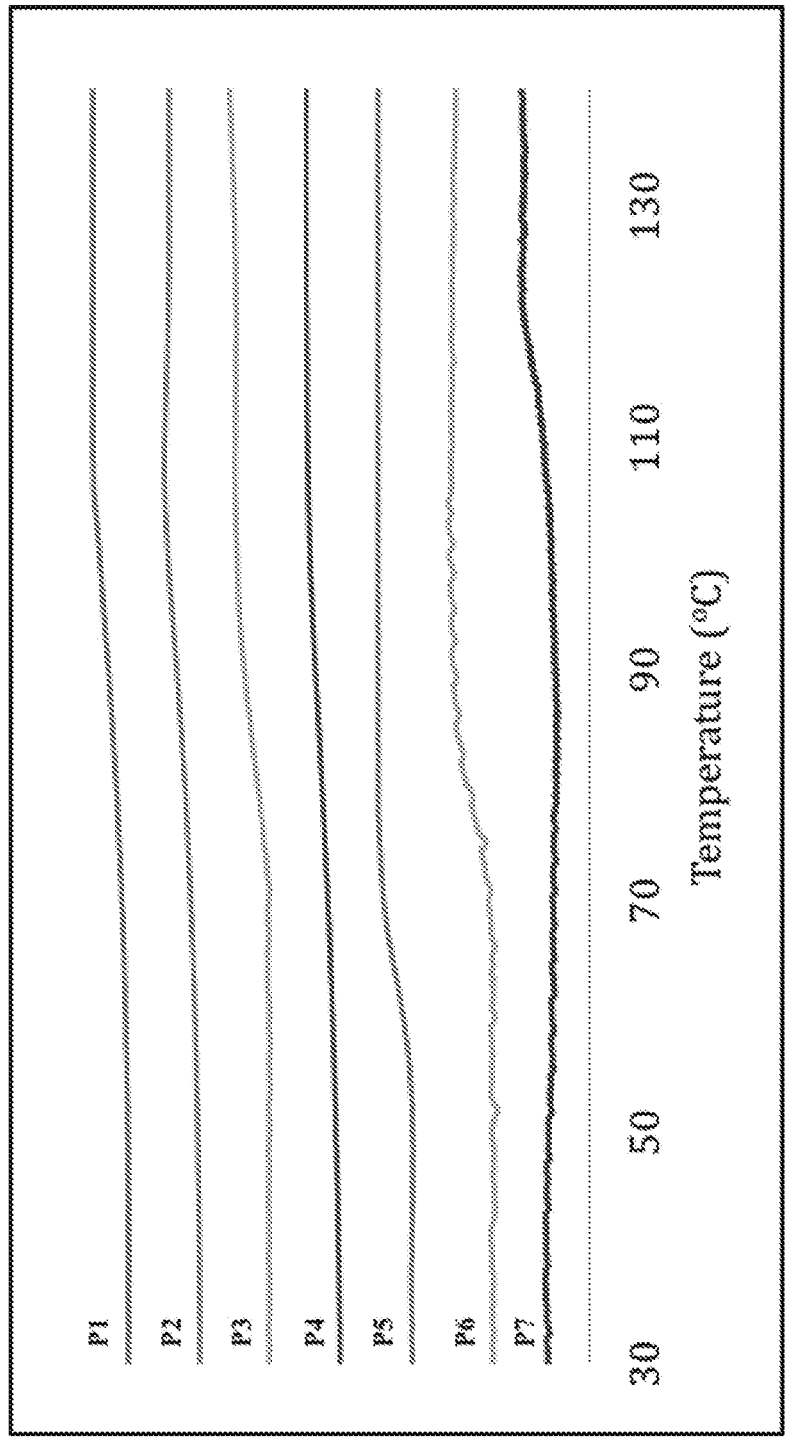
FIG. 33 shows the stacked DSC traces of p-Coumaryl-based poly(ether-amide)s (P1-P7), in accordance with one or more embodiments of the invention.
Figure 34:
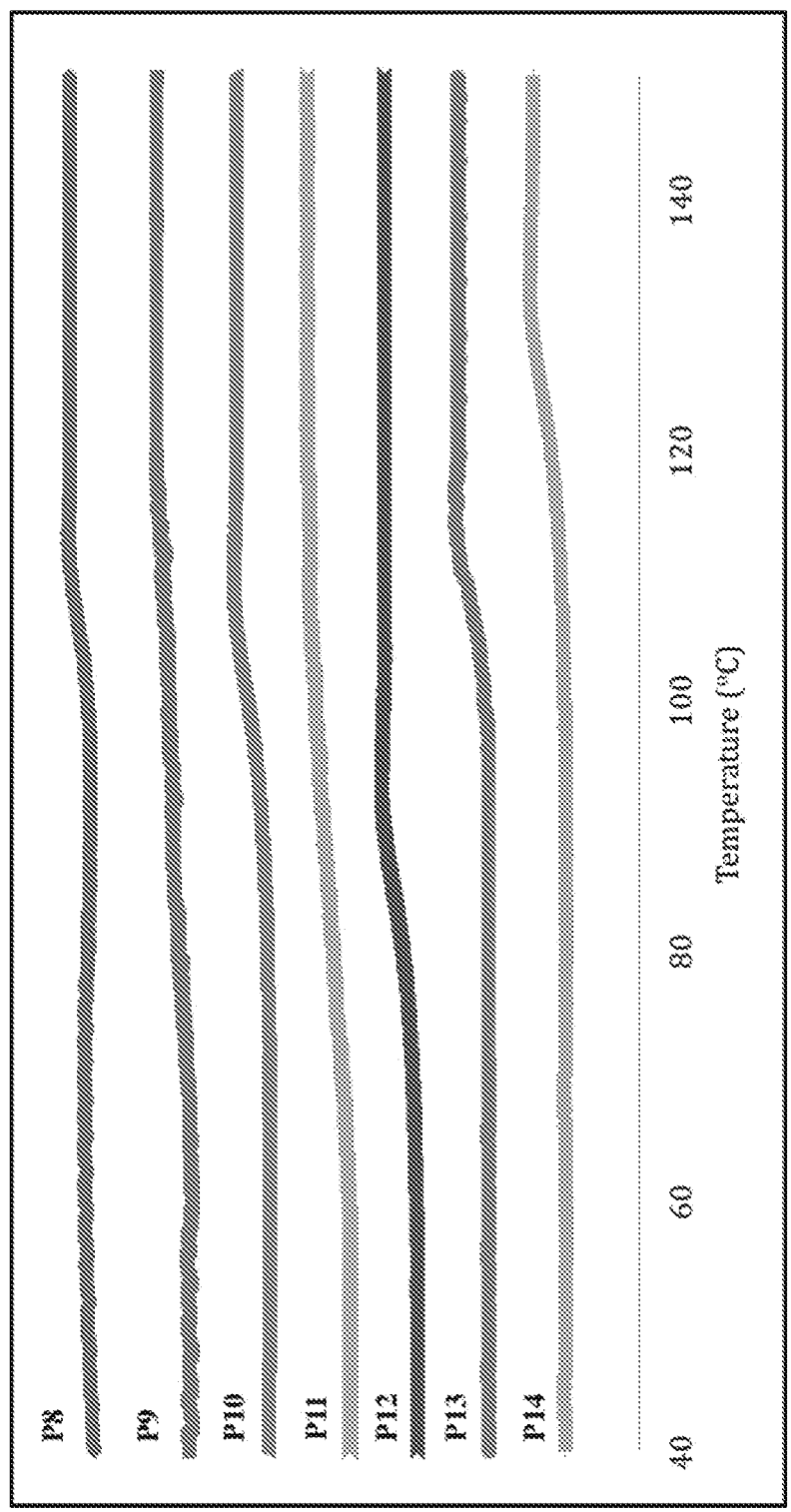
FIG. 34 shows the stacked DSC traces of ferulyl-based poly(ether-amide)s (P8-P14), in accordance with one or more embodiments of the invention.
Figure 35:
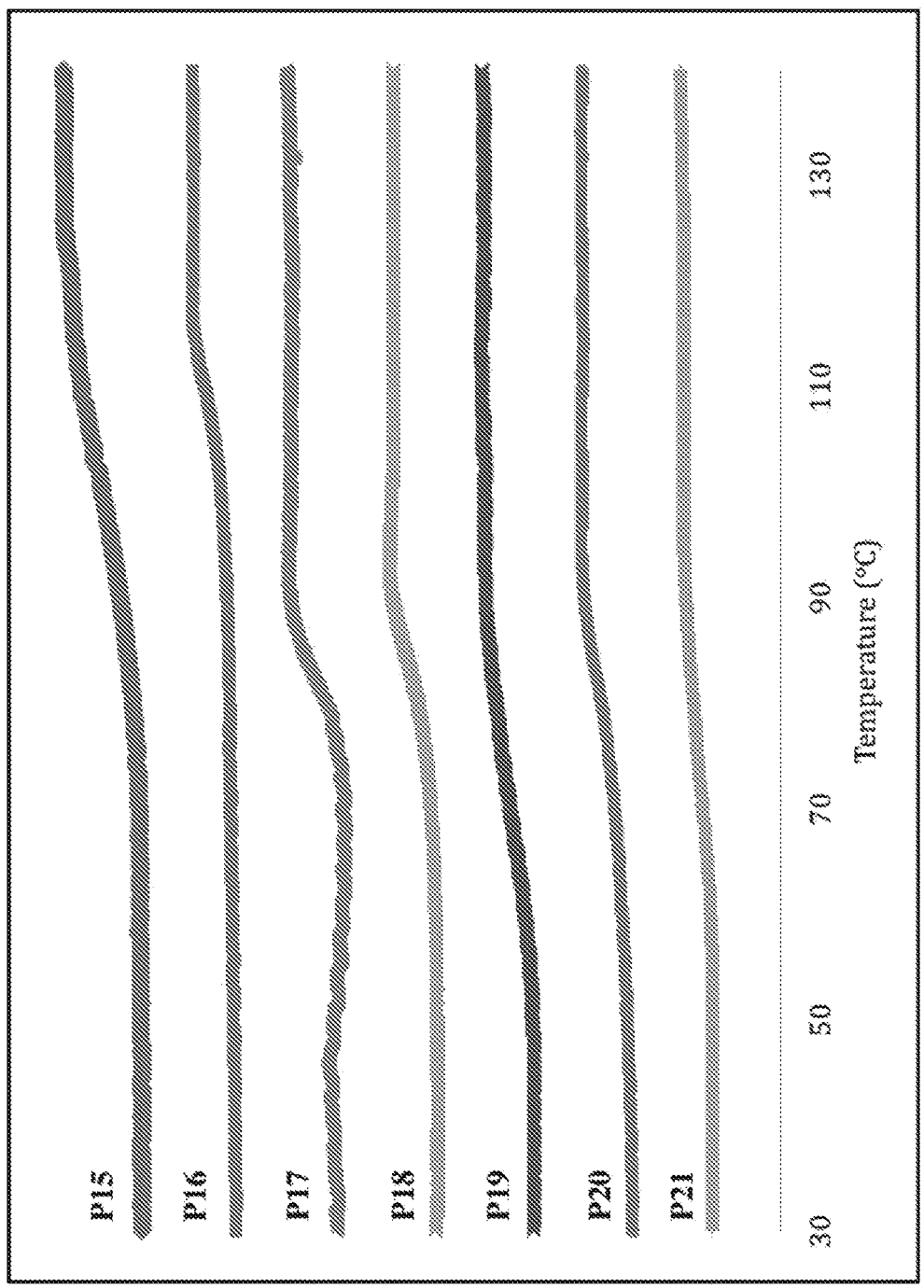
FIG. 35 shows the stacked DSC traces of sinapyl-based poly(ether-amide)s (P15-P21), in accordance with one or more embodiments of the invention.

The thermal stability of the poly(ether-amides) was studied using thermogravimetric analysis (TGA). Polymer samples were heated from 30 to 800° C. under a nitrogen atmosphere (FIGS. 33-35). Most of the polymers in this series featured initial mass loss ($T_{d5}$) between 120 and 210° C., lower temperatures than would be typically expected for these materials (Table 7). Despite efforts to remove water prior to the thermal decomposition studies, water loss was likely the cause of low initial decomposition temperatures. As these materials contain amide linkages, they are inherently hydroscopic and the retention of water is not surprising. The presence of water in the polymer samples can be further exemplified by the high temperatures required to reach 25% mass loss ($T_{d25}$). For example, P6 exhibits an initial decomposition temperature ($T_{d5}$) of 150.3° C. but requires the polymer sample to be heated to 410.8° C. to cause 25% mass loss. The length of the aliphatic diamine linker appeared to have no significant effect on the thermal stability of the poly(ether-amide)s. The incorporation of aromatic diamine linkers also did not have a substantial effect on thermal stability, regardless of the pattern of substitution. Overall, the polymers have mild thermal stability and potential for use in melt processing. Most commercial thermoplastics are processed between 100 and 250° C., depending on their melting temperature [84]. Prior to large scale thermal processing, these poly(ether-amide)s should undergo more rigorous methods to remove residual water. After removal of the residual water, these materials will likely exhibit increased thermal stability in contrast to the data discussed here.

In this example, we have described the synthesis of a series of aromatic-aliphatic poly(ether-amide)s from monolignol-based ether dimers and various aliphatic and aromatic diamines. Aliphatic diamines were chosen as co-monomers to improve the solubility and processability of monolignol-based polymers. Additionally, the five aliphatic diamines used in this study are available from biological sources. While the isolated poly(ether-amide)s were insoluble in standard organic solvents (excluding DMF), the moderate glass transition temperatures and thermal stability observed offer promise for these materials in melt processing applications. Additionally, the modularity of this synthetic approach could be used to rapidly generate a series of diverse polymers with well-tuned properties. The versatility of this method increases the potential applications for this polymer system industrially.

In the future, our group will explore processing options with the series of poly(ether-amide)s generated, as well as utilizing these polymers as a framework for the creation of higher-order materials. With two grafting sites per monolignol-based ether dimer, these materials could easily be used in the preparation of densely grafted copolymers or three-dimensional polymer networks. Additionally, the distance between grafting sites could be well-controlled and tuned by altering either the length of the aliphatic spacer in the monolignol-based dimer or the length of the aliphatic diamine linker. In conclusion, this system allowed for the rapid preparation of a series of poly(ether-amide)s from biological-based components, which can easily be adapted and used for a variety of purposes. This targeted upgrading of underutilized bio-based materials has provided a unique set of functional materials, with the prospect of their use in the development of other novel materials.

Experimental Section

Materials.

4-hydroxybenzaldehyde (98%, TCI America), vanillin (99%, Alfa Aesar), 3,5-dimethoxy-4-hydroxybenzaldehyde (98%, Acros), malonic acid (99%, Alfa Aesar), tert-butanol (99%, Alfa Aesar), acetic anhydride (99.5%, Fisher), acetone (ACS Grade, Fisher), sulfuric acid (conc., ACS Grade, Fisher), piperidine (99%, Spectrum), trifluoroacetic acid (99.5%, Fisher) 1,4-diaminobutane (98+%, Alfa Aesar), 1,8-diaminooctane (98%, Acros), 1,10-diaminodecane (97%, Acros), p-phenylenediamine (99+%, Acros), m-phenylenediamine (99+%, Acros), sodium hydroxide (ACS Grade, Fisher), and N,N-dimethylformamide (HPLC grade, Alfa Aesar) were purchased and used as received. Pyridine (99%, Fisher) was distilled over KOH prior to use. Dichloromethane (ACS Grade, Fisher) was distilled from $CaH_2$ prior to use. Hexamethylene diamine (99.5%, Acros) was sublimed under reduced pressure prior to use. Ethylenediamine (98%, Acros) was distilled prior to use to remove discoloration. Meldrum's acid [85], tert-butyl malonate [86], and 1,4-dibromobutane [87] were synthesized according to published procedures. Silica gel 60 (230-400 mesh, Fisher) was used for column chromatography. Thin layer chromatography (TLC) was conducted with silica gel 60-F245 plates and visualized with a handheld UV lamp. NMR solvents $d_6$-DMSO, $CDCl_3$, and $C_6D_6$ were obtained from Cambridge Isotope Laboratories and used as received.

$^1$H, $^{13}$C, and FTIR Spectroscopy.

$^1$H NMR spectra were recorded on Bruker AV-300 or Bruker DRX-500 spectrometers at room temperature in $d_6$-DMSO, unless either wise noted. Chemical shifts are reported with respect to internal solvent, 2.50 ppm ($d_6$-DMSO), 7.16 ($C_6D_6$), or 7.26 ($CDCl_3$) for $^1$H NMR spectra. $^{13}$C NMR spectra were recorded on a Bruker AV-500 spectrometer with a dual cryoprobe ($^{13}$C, $^1$H). Chemical shifts are reported with respect to internal solvent, 39.52 ppm ($d_6$-DMSO), 128.06 ppm ($C_6D_6$), or 77.16 ppm ($CDCl_3$) for $^{13}$C NMR spectra. Infrared absorption spectra were collected using a Jasco 4210-FT/IR spectrometer from 4000 to 400 $cm^{-1}$ from KBr pellets. All samples were dried at 100° C. in a vacuum oven overnight (at least 12 h) prior to characterization.

Molecular Weight Characterization.

Molecular weight ($M_n$ and $M_w$) and dispersity (Đ=$M_w$/$M_n$) were determined using gel permeation chromatography (GPC). Samples were dissolved in 0.01 M LiBr in N,N-dimethylformamide (DMF) at a concentration of 2-5 mg/mL and were passed through a 0.20 µm PTFE filter before injection. GPC for all polymers was conducted on a Jasco system equipped with a refractive index detector, a UV detector, a Waters Styragel guard column, and four Waters HR Styragel 5 µm columns (100-5K, 500-30K, 50-100K, 5-600 K) using 0.01 M LiBr in N,N-dimethylformamide (DMF) at 40° C. and a flow rate of 1.0 mL/min. Calibration was performed using near-monodisperse polystyrene standards ($M_n$=1,250 to 549,000 Da) from Jordi Laboratories and chromatograms were analyzed using ChromNAV chromatography software.

Thermal Characterization.

All samples were dried at 100° C. in a vacuum oven overnight (at least 12 h) prior to all thermal characterization. Thermogravimetric analysis (TGA) was conducted on a Perkin Elmer Pyris Diamond TG/DTA Thermogravimetric/Differential Thermal Analyzer. The TGA instrument was operated under an argon atmosphere, using platinum crucibles. Samples (6-12 mg) were heated from 25° C. to 800° C. at a rate of 10° C. min/mL. Pyris Manager was used to analyze the data. Decomposition temperatures $T_{d5}$, $T_{d10}$, and $T_{d25}$ were measured at 5, 10, and 25% mass loss, respectively. Differential scanning calorimetry (DSC) was performed on a Perkin Elmer DSC 8000 to determine glass transition temperature ($T_g$). Samples (5-8 mg) were heated from −30 to 200° C. at a rate of 10° C./min and cooled to −30° C. at a rate of 10° C./min. A minimum of two heating and cooling cycles were performed and $T_g$ was measured from the second heating cycle. Pyris Manager was used to analyze the data.

Tert-Butyl Ester Monomer Synthesis.

p-Coumaroyl Tert-Butyl Ester (2a).

4-hydroxybenzaldehyde (6.99 g, 57.3 mmol, 1 eq) was weighed and added to a round bottom flask along with tert-butyl malonate (11.01 g, 68.7 mmol, 1.2 eq). 30.0 mL of pyridine and 0.3 mL of piperidine were added to the reaction mixture and the reaction was heated to reflux overnight. After refluxing, the reaction was cooled to room temperature and concentrated under reduced pressure. The resulting residue was dissolved in diethyl ether (70 mL) and washed with saturated sodium bicarbonate (2×70 mL), 1 M HCl (2×40 mL), and deionized water (1×40 mL). The organic layer was dried over $MgSO_4$ and the solvent was removed via rotary evaporation to yield the crude product. The crude product was purified on silica gel via flash column chromatography using 3:2 hexanes:ethyl acetate as the elutant. Yield: 4.04 g, 32.1% $^1$H NMR (300 MHz, $d_6$-DMSO): δH 7.67 (d, 2H, Ar—H), 7.62 (d, 1H, CCH═CHCOO(CH$_3$)$_3$), 7.20 (d, 2H, Ar—H), 6.54 (d, 1H, CCH═CHCOO(CH$_3$)$_3$), 1.48 (s, 9H, COO(CH$_3$)$_3$).

Feruloyl Tert-Butyl Ester (2b).

Yield: 6.49 g, 65.3% $^1$H NMR (300 MHz, $d_6$-DMSO): δH 7.48 (d, 1H, CCH═CHCOO(CH$_3$)$_3$), 7.27 (s, 1H, Ar—H), 7.08 (d, 1H, Ar—H), 6.80 (d, 1H, Ar—H), 6.37 (d, 1H, CCH═CHCOO(CH$_3$)$_3$), 3.81 (s, 3H, Ar—OCH$_3$), 1.47 (s, 9H, COO(CH$_3$)$_3$).

Sinapoyl Tert-Butyl Ester (2c).

3,5-dimethoxy-4-hydroxybenzaldehyde (3.17 g, 17.4 mmol, 1 eq) was weighed and added to a round bottom flask along with tert-butyl malonate (3.90 g, 24.4 mmol, 1.2 eq). 20.0 mL of pyridine and 0.2 mL of piperidine were added to the reaction mixture and the reaction was heated to reflux overnight. After refluxing, the reaction was cooled to room temperature and concentrated under reduced pressure. The resulting residue was dissolved in diethyl ether (50 mL) and washed with saturated sodium bicarbonate (2×50 mL), 1 M HCl (2×30 mL), and deionized water (1×30 mL). The organic layer was dried over $MgSO_4$ and solvent was removed using a rotary evaporator to yield the product as a white solid. Yield: 3.57 g, 73.1% $^1$H NMR (300 MHz, $d_6$-DMSO): δH 8.89 (s, 1H, Ar—OH), 7.47 (d, 1H, CCH═CHCOO(CH$_3$)$_3$), 6.98 (s, 2H, Ar—H), 6.44 (d, 1H, CCH═CHCOOtBu), 3.79 (s, 6H, Ar—OCH$_3$), 1.48 (s, 9H, COOC(CH$_3$)$_3$). $^{13}$C NMR (500 MHz, $d_6$-DMSO): δC 166.46 (CCH=CHCOO(CH$_3$)$_3$), 148.46 (C—OCH$_3$), 144.87 (CCH=CHCOO(CH$_3$)$_3$), 138.50 (C—OH), 124.97 (CCH=CHCOO(CH$_3$)$_3$), 117.26 (CCH=CHCOO(CH$_3$)$_3$), 106.49 (Ar C—H), 79.90 (C(CH$_3$)$_3$), 56.53 (OCH$_3$), 28.39 (C(CH$_3$)$_3$).

Tert-Butyl Ether Dimer Synthesis.

p-Coumaroyl Tert-Butyl Ether Dimer (3a).

p-Coumaroyl tert-butyl ester (4.04 g, 18.4 mmol, 2.2 eq) was weighed and added to a two-necked round bottom flask along with 30 mL of N,N-dimethylformamide (DMF). The reaction mixture was cooled to 0° C. and sodium hydride (0.44 g, 18.4 mmol, 2.2 eq) was added portionwise. After 30 minutes, a solution of 1,4-dibromobutane (1.0 mL, 8.3 mmol, 1 eq)) in 5 mL DMF was added dropwise over 30 minutes via an addition funnel. The reaction was allowed to slowly warm to room temperature and stir overnight. After 12 hours at room temperature, the reaction was then heated to reflux for 6 hours. The reaction was then cooled to room temperature, diluted with ethyl acetate (70 mL), washed with deionized water (2×70 mL) and brine (1×50 mL). The organic layer was separated, dried over MgSO$_4$, and volatiles were removed via rotary evaporation to yield the crude product as an off-white crystalline solid. The crude product was purified on silica gel via flash column chromatography using a gradient of 7:3 to 3:2 hexanes:ethyl acetate as the elutant. Yield: 2.08 g, 50.4%1H NMR (300 MHz, C$_6$D$_6$): δH 7.88 (d, 1H, CCH=CHCOOtBu), 7.15 (d, 2H, Ar—H), 6.63 (d, 2H, Ar—H), 6.45 (d, 1H, CCH=CHCOOtBu), 3.49 (br s, 2H, —OCH$_2$CH$_2$), 1.60 (br s, 2H, —OCH$_2$CH$_2$), 1.51 (s, 9H, C(CH$_3$)$_3$). $^{13}$C NMR (500 MHz, C$_6$D$_6$): δC 166.72 (COOC(CH$_3$)$_3$), 161.18 (COCH$_2$CH$_2$), 143.82 (CH=CHCOOtBu), 130.19 (Ar), 128.39 (CCH=CHCOOtBu, under C$_6$D$_6$), 118.75 (CH=CHCOOtBu), 115.32 (Ar), 80.04 (C(CH$_3$)$_3$), 67.66 (COCH$_2$CH$_2$), 28.66 (C(CH$_3$)$_3$), 26.34 (COCH$_2$CH$_2$).

Feruloyl Tert-Butyl Ether Dimer (3b).

Yield: 2.10 g, 52.5%$^1$H NMR (300 MHz, C$_6$D$_6$): 6H 8.04 (d, 1H, CCH=CHCOOtBu), 6.97 (d, 1H, Ar—H), 6.94 (s, 1H, Ar—H), 6.63 (d+d, 2H, Ar—H and CCH=CHCOOtBu), 3.70 (br s, 2H, OCH$_2$CH$_2$), 3.38 (s, 3H, Ar—OCH$_3$), 1.84 (br s, 2H, OCH$_2$CH$_2$), 1.64 (s, 9H, C(CH$_3$)$_3$). 13C NMR (500 MHz, C$_6$D$_6$): δC 166.75 (COOtBu), 151.56 (C—OCH$_3$), 150.58 (COCH$_2$CH$_2$), 144.43 (CCH=CHCOOtBu), 128.37 (CCH=CHCOOtBu), 122.69 (Ar), 118.61 (Ar), 113.10 (CH=CHCOOtBu), 110.81 (Ar), 80.08 (OC(CH$_3$)$_3$), 68.65 (COCH$_2$CH$_2$), 55.56 (C—OCH$_3$), 28.67 (OC(CH$_3$)$_3$), 26.60 (COCH$_2$CH$_2$).

Sinapoyl Tert-Butyl Ether Dimer (3c).

Yield: 1.98 g, 48.6%$^1$H NMR (300 MHz, C$_6$D$_6$): δH 7.88 (d, 1H, CCH=CHCOOtBu), 6.54 (d+s, 3H, CCH=CHCOOtBu and Ar—H), 4.15 (br m, 2H, OCH$_2$CH$_2$), 3.27 (s, 6H, Ar—OCH$_3$), 2.09 (br m, 2H, OCH$_2$CH$_2$), 1.52 (s, 9H, C(CH$_3$)$_3$). $^{13}$C NMR (500 MHz, C$_6$D$_6$): δC 166.26 (COOtBu), 154.43 (C—OCH$_3$), 144.34 (CCH=CHCOOtBu), 140.56 (COCH$_2$CH$_2$), 130.14 (CCH=CHCOOtBu), 119.52 (CCH=CHCOOtBu), 105.82 (Ar), 79.97 (OC(CH$_3$)$_3$), 73.14 (COCH$_2$CH$_2$), 55.68 (C—OCH$_3$), 28.32 (OC(CH$_3$)$_3$), 27.35 (COCH$_2$CH$_2$).

Diacid Ether Dimer Synthesis.

p-Coumaryl Diacid Ether Dimer (4a).

p-Coumaryl tert-butyl ether dimer (2.08 g, 4.2 mmol, 1 eq) was weighed and added to a round bottom flask along with trifluoroacetic acid (12.9 mL, 168.3 mmol, 40 eq). Reaction was stirred at room temperature for 4 hours. Volatiles were removed under vacuum to yield the product as a white solid. Yield: 1.52 g, 94.4%1H NMR (300 MHz, d$_6$-DMSO, sparingly soluble): δH 7.64 (d, 2H, Ar—H), 7.56 (d, 1H, CH=CHCOOH), 6.98 (d, 2H, Ar—H), 6.39 (d, 2H, CH=CHCOOH), 4.09 (br s, 2H, OCH$_2$CH$_2$), 1.88 (br s, 2H, OCH$_2$CH$_2$). $^{13}$C NMR (500 MHz, d$_6$-DMSO, sparingly soluble): δC 167.84 (COOH), 160.33 (COCH$_2$CH$_2$), 143.78 (CH=CHCOOH), 129.96 (Ar), 126.76 (CCH=CHCOOH), 116.44 (CH=CHCOOH), 114.83 (Ar), 67.30 (OCH$_2$CH$_2$), 25.29 (OCH$_2$CH$_2$).

Ferulyl Diacid Ether Dimer (4b).

Yield: 1.5433 g, 92.4% $^1$H NMR (300 MHz, d$_6$-DMSO): δH 7.55 (d, 1H, CH=CHCOOH), 7.31 (s, 1H, Ar—H), 7.20 (d, 1H, Ar—H), 6.99 (d, 1H, Ar—H), 6.46 (d, 1H, CH=CHCOOH), 4.08 (br s, 2H, OCH$_2$CH$_2$), 3.81 (s, 3H, Ar—OCH$_3$), 1.89 (br s, OCH$_2$CH$_2$). $^{13}$C NMR (500 MHz, d$_6$-DMSO, sparingly soluble): δC 167.90 (COOH), 150.12 (COCH$_3$), 149.09 (COCH$_2$CH$_2$), 144.19 (CCH=CHCOOH), 127.02 (CCH=CHCOOH), 122.64 (Ar), 116.65 (Ar), 112.48 (CCH=CHCOOH), 110.49 (Ar), 67.92 (OCH$_2$CH$_2$), 55.67 (COCH$_3$), 25.44 (OCH$_2$CH$_2$).

Sinapyl Diacid Ether Dimer (4c).

Yield: 1.59 g, 97.8%$^1$H NMR (300 MHz, d$_6$-DMSO): δH 7.56 (d, 1H, CH=CHCOOH), 7.02 (s, 2H, Ar—H), 6.56 (d, 1H, CH=CHCOOH), 3.93 (br s, 2H, OCH$_2$CH$_2$), 3.79 (s, 6H, Ar—OCH$_3$), 1.78 (br s, 2H, OCH$_2$CH$_2$). $^{13}$C NMR (500 MHz, d$_6$-DMSO): δC 167.76 (COOH), 153.27 (COCH$_3$), 144.25 (CCH=CHCOOH), 138.43 (COCH$_2$CH$_2$), 129.67 (CCH=CHCOOH), 118.37 (CCH=CHCOOH), 105.78 (Ar), 72.16 (COCH$_2$CH$_2$), 56.01 (COCH$_3$), 26.18 (COCH$_2$CH$_2$).

Poly(Ether-Amide) Synthesis.

General Polymerization Procedure.

The desired diacid ether dimer (1 eq) was weighed and added to a round bottom flask. Thionyl chloride (20 eq) was added to the flask along with a drop of DMF, and the reaction was heated to reflux for 6 hours. Volatiles were removed under vacuum to yield the diacid chloride dimer. The desired diamine (3 eq) was weighed and added to a 100 mL beaker along with 15 mL of 0.5 M NaOH and a stir bar. The isolated diacid chloride dimer was dissolved in 15 mL of distilled dichloromethane and added quickly to the rapidly stirring diamine solution. A solid precipitate formed immediately and the resulting slurry was allowed to stir for two minutes. The slurry was transferred to an Eppendorf tube and centrifuged at 4.4×10$^3$ rpm for 20 minutes. The biphasic solution was decanted from the Eppendorf tube and the residual solid was washed with water (2×15 mL). After each washing, the slurry (water & polymer) was centrifuged at 4.4×10$^3$ rpm for 10 minutes. The resulting solid was dried under reduced pressure to yield the corresponding polymer as a yellow solid. Characterization data for each poly(ether-amide) can be found in the Figures.

Polymer Characterization p-Coumaryl diacid+ethylenediamine (P1). Yield 0.2321 g, 77.2% p-Coumaryl diacid+1,4-diaminobutane (P2). Yield 0.2346 g, 71.6% p-Coumaryl diacid+1,6-diaminohexane (P3), Yield 0.2486 g, 68.7% p-Coumaryl diacid+1,8-diaminooctane (P4). Yield 0.2161 g, 55.2% p-Coumaryl diacid+1,10-diaminodecane (P5). Yield 0.2622 g, 64.5% p-Coumaryl diacid+m-phenylenediamine (P6). Yield 0.2604 g, 70.6% p-Coumaryl diacid+p-phenylenediamine (P7). Yield 0.2994 g, 81.9%

Ferulic diacid+ethylenediamine (P8). Yield 0.1977 g, 56.3%

Ferulic diacid+1,4-diaminobutane (P9). Yield 0.1789 g, 51.0%
Ferulic diacid+1,6-diaminohexane (P10). Yield 0.2637 g, 70.6%
Ferulic diacid+1,8-diaminooctane (P11). Yield 0.2529 g, 62.8%
Ferulic diacid+1,10-diaminodecane (P12). Yield 0.3104 g, 73.9%
Ferulic diacid+m-phenylenediamine (P13). Yield 0.1892 g, 51.3%
Ferulic diacid+p-phenylenediamine (P14). Yield 0.2494 g, 68.4%
Sinapyl diacid+ethylenediamine (P15). Yield 0.2228 g, 65.1%
Sinapyl diacid+1,4-diaminobutane (P16). Yield 0.2549 g, 68.6%
Sinapyl diacid+1,6-diaminohexane (P17). Yield 0.2219 g, 56.5%
Sinapyl diacid+1,8-diaminooctane (P18). Yield 0.4804 g, 87.9%
Sinapyl diacid+1,10-diaminodecane (P19). Yield 0.4164 g, 74.4%
Sinapyl diacid+m-phenylenediamine (P20). Yield 0.4564 g, 78.7%
Sinapyl diacid+p-phenylenediamine (P21). Yield 0.3877 g, 78.8%

REFERENCES

Note: This application references a number of different publications as indicated throughout the specification by reference numbers enclosed in brackets, e.g., [x]. A list of these different publications ordered according to these reference numbers can be found below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

[1] Lebo, S. E. et al. *Kirk-Othmer Encyclopedia of Chemical Technology*, John Wiley & Sons, Inc.: New York, 2001; pp 1-32.
[2] Doherty, W. O. S. et al. *Ind. Crops Prod.*, 2011, 33, 259-276.
[3] Uraki, Y. et al. *Biomacromolecules*, 2012, 13, 867-872.
[4] Bertini, F. et al. *Polym. Degrad. Stab.*, 2012, 97, 1979-1987.
[5] Pinkert, A. et al. *Green Chem.*, 2011, 13, 3124-3136.
[6] Takeichi, T. et al. *Polym. J.*, 2008, 40 (12), 1121-1131.
[7] Zhu, M. Q. et al. *Chem. Comm.*, 2001, 365-366.
[8] Ouimet, M. A. et al. *Biomacromolecules*, 2013, 14(3), 854-61.
[9] Comi, M. et al. *J. Polym. Sci., Part A: Polym. Chem.* 2013, 51(22), 4894-903.
[10] Dros, A. B. et al. *Green Chem.*, 2015 DOI:10.1039/c5g01549a.
[11] Isikgor, F. H. et al. *Polym. Chem.*, 2015, 6, 4497.
[12] J. E. Holladay, J. F. White, J. J. Bozell, D. Johnson and U. S. D. of Energy, *Top Value-Added Chemicals from Biomass-Volume II—Results of Screening for Potential Candidates from Biorefinery Lignin*, Pacific Northwest National Laboratory, Richland, Wash., 2007, vol. 2.
[13] D. Kai, M. J. Tan, P. L. Chee, Y. K. Chua, Y. L. Yap and X. J. Loh, *Green Chem.*, 2016, 1175-1200.
[14] J. H. Lora and W. G. Glasser, *J. Polym. Environ.*, 2002, 10, 39-48.
[15] V. K. Thakur, M. K. Thakur, P. Raghavan and M. R. Kessler, *ACS Sustain. Chem. Eng.*, 2014, 2, 1072-1092.
[16] E. Ten and W. Vermerris, *J. Appl. Polym. Sci.*, 2015.
[17] S. Sen, S. Patil and D. S. Argyropoulos, *Green Chem.*, 2015.
[18] B. Lochab, S. Shukla and I. K. Varma, *RSC Adv.*, 2014, 4, 21712-21752.
[19] S. Farigrieve, *Degredation and Stabilization of Aromatic Polyesters*, iSmithers, Shropshire, United Kingdom, 2009.
[20] R. J. Müller, I. Kleeberg and W.-D. Deckwer, *J. Biotechnol.*, 2001, 86, 87-95.
[21] C. Fonseca, M. H. Gil and P. N. Simões, *Prog. Polym. Sci.*, 2014, 39, 1291-1311.
[22] Rodriguez-Galan, L. Franco and J. Puiggali, *Polymers (Basel)*, 2010, 3, 65-99.
[23] M. Vert, J. Feijen, G. Albtersson, G. Scott and E. Chiellini, *Biodegradable polymers and plastics*, The Royal Society of Chemistry, Whiltshire, England, 1992.
[24] S. K. Murase and J. Puiggali, in *Natural and Synthetic Biomedial Polymers*, Elsevier Inc., 2014, pp. 145-166.
[25] N. Yonezawa, F. Toda and M. Hasegawa, *Die Makromol. Chemie, Rapid Commun.*, 1985, 6, 607-611.
[26] T. Fey, H. Keul and H. Höcker, *Macromolecules*, 2003, 36, 3882-3889.
[27] T. Lebarbé, L. Maisonneuve, T. H. Nga Nguyen, B. Gadenne, C. Alfos and H. Cramail, *Polym. Chem.*, 2012, 3, 2842.
[28] J. Zuo, S. Li, L. Bouzidi and S. S. Narine, *Polymer (Guildf)*, 2011, 52, 4503-4516.
[29] R. Triki, M. Abid, M. Tessier, S. Abid, R. El Gharbi and A. Fradet, *Eur. Polym. J.*, 2013, 49, 1852-1860.
[30] M. Pinilla, M. B. Martinez and J. A. Galbis, *J. Polym. Sci. Part A Polym. Chem.*, 2010, 48, 4711-4720.
[31] R. Wang, T. Ren, Y. Bai, Y. Wang, J. Chen, L. Zhang and X. Zhao, *J. Appl. Polym. Sci.*, 2016, 133, n/a-n/a.
[32] F. H. Isikgor and C. R. Becer, *Polym. Chem.*, 2015, 6, 4497-4559.
[33] T. G. Tilley, *Ann. der Chemie and Pharm.*, 1841, 39, 160-168.
[34] Brehmer, in *Bio-based plastics: Materials and applications*, ed. S. Kabasci, Wiley-Interscience, 2013, pp. 275-293.
[35] Davidson and S. A. Bernhard, *J. Am. Chem. Soc.*, 1948, 70, 3426-3428.
[36] M. R. Smith, H. S. Rzepa, A. J. P. White, D. Billen and K. K. Hii, *J. Org. Chem.*, 2010, 75, 3085-3096.
[37] M. A. Ouimet, N. D. Stebbins and K. E. Uhrich, *Macromol. Rapid Commun.*, 2013, 34, 1231-1236.
[38] M. A. Ouimet, J. Griffin, A. L. Carbone-Howell, W. H. Wu, N. D. Stebbins, R. Di and K. E. Uhrich, *Biomacromolecules*, 2013, 14, 854-861.
[39] T. Mekonnen, P. Mussone, H. Khalil and D. Bressler, *J. Mater. Chem. A*, 2013, 1, 13379.
[40] S. S. Kuhire, C. V. Avadhani and P. P. Wadgaonkar, *Eur. Polym. J.*, 2015, 71, 547-557.
[41] F. Pion, P.-H. Ducrot and F. Allais, *Macromol. Chem. Phys.*, 2014, 215, 431-439.
[42] M. Z. Oulame, F. Pion, S. Allauddin, K. V. S. N. Raju, P. H. Ducrot and F. Allais, *Eur. Polym. J.*, 2015, 63, 186-193.
[43] P. W. Morgan and S. L. Kwolek, *J. Chem. Educ.*, 1959, 36, 182.

[44] L. Wittbecker and P. W. Morgan, *J. Polym. Sci. Part A Polym. Chem.*, 1996, 34, 521-529.
[45] P. W. Morgan, in *Condensation Polymers: By Interfacial and Solution Methods*, Interscience, New York, 1965, pp. 65-115.
[46] M. Vera, A. Almontassir, A. Rodriguez-Galan and J. Puiggali, *Macromolecules,* 2003, 36, 9784-9796.
[47] Vlachopoulos and D. Strutt, *Mater. Sci. Technol.,* 2003, 19, 1161-1169.
[48] Wang, Y. Wang and L. Ren, *J. Appl. Polym. Sci.,* 2008, 109, 1310-1318.
[49] Chen and H. G. Zachmann, *Polymer (Guildf).,* 1991, 32, 1612-1621.
[50] J. Rieger, *J. Therm. Anal.,* 1996, 46, 965-972.
[51] Okada, *Prog. Polym. Sci.,* 2002, 27, 87-133.
[52] A. Ouimet, J. J. Faig, W. Yu and K. E. Uhrich, *Biomacromolecules,* 2015, 16, 2911-2919.
[53] Berezina, N.; Martelli, S. M. In Renewable Resources for Biorefineries; 2014; pp 1-28.
[54] Jambeck, J. R.; Geyer, R.; Wilcox, C.; Siegler, T. R.; Perryman, M.; Andrady, A.; Narayan, R.; Law, K. L. Science (80-.). 2015, 347 (6223), 768.
[55] Mialon, L.; Pemba, A. G.; Miller, S. A. Green Chem. 2010, 12, 1704.
[56] Mialon, L.; Vanderhenst, R.; Pemba, A. G.; Miller, S. A. Macromol. Rapid Commun. 2011, 32, 1386.
[57] Hillmyer, M. A.; Tolman, W. B. Acc. Chem. Res. 2014, 47 (8), 2390.
[58] Diaz, A.; Katsarava, R.; Puiggali, J. Int. J. Mol. Sci. 2014, 15 (5), 7064.
[59] Gandini, A.; Lacerda, T. M.; Carvalho, A. J. F.; Trovatti, E. Chem. Rev. 2016, 116 (3), 1637.
[60] Thakur, V. K.; Thakur, M. K.; Raghavan, P.; Kessler, M. R. ACS Sustain. Chem. Eng. 2014, 2, 1072.
[61] Ten, E.; Vermerris, W. J. Appl. Polym. Sci. 2015.
[62] Sen, S.; Patil, S.; Argyropoulos, D. S. Green Chem. 2015.
[63] Pion, F.; Ducrot, P.-H.; Allais, F. Macromol. Chem. Phys. 2014, 215, 431.
[64] Mialon, L.; Vanderhenst, R.; Pemba, A. G.; Miller, S. A. Macromol. Rapid Commun. 2011, 32 (17), 1386.
[65] Oulame, M. Z.; Pion, F.; Allauddin, S.; Raju, K. V. S. N.; Ducrot, P.-H.; Allais, F. Eur. Polym. J. 2015, 63, 186.
[66] Kuhire, S. S.; Avadhani, C. V.; Wadgaonkar, P. P. Eur. Polym. J. 2015, 71, 547.
[67] Ouimet, M. A.; Griffin, J.; Carbone-Howell, A. L.; Wu, W. H.; Stebbins, N. D.; Di, R.; Uhrich, K. E. Biomacromolecules 2013, 14 (3), 854.
[68] Ouimet, M. A.; Stebbins, N. D.; Uhrich, K. E. Macromol. Rapid Commun. 2013, 34 (15), 1231.
[69] Ouimet, M. A.; Faig, J. J.; Yu, W.; Uhrich, K. E. Biomacromolecules 2015, 16 (9), 2911.
[70] Nguyen, H. T. H.; Reis, M. H.; Qi, P.; Miller, S. A. Green Chem. 2015, 17 (9), 4512.
[71] Hatfield, G. R.; Guo, Y.; Killinger, W. E.; Andrejak, R. A.; Roubicek, P. M. Macromolecules 1993, 26 (24), 6350.
[72] Delaviz, Y.; Gungor, A.; McGrath, J. E.; Gibson, H. W. Polymer (Guildf). 1993, 34 (1), 210.
[73] Gutch, P. K.; Banerjee, S.; Jaiswal, D. K. J. Appl. Polym. Sci. 2003, 89 (3), 691.
[74] Hajibeygi, M.; Shabanian, M. Des. Monomers Polym. 2013, 16 (3), 222.
[75] Onciu, M. J. Appl. Polym. Sci. 2007, 103 (3), 2013.
[76] Hsiao, S.-H.; Lin, K.-H. Polymer (Guildf). 2004, 45 (23), 7877.
[77] Garcia, J. M.; de la Campa, J. G.; de Abajo, J. J. Polym. Sci. Part A Polym. Chem. 1996, 34(4), 659.
[78] Garcia, J. M.; Alvarez, J. C.; De La Campa, J. G.; De Abajo, J. J. Appl. Polym. Sci. 1998, 67(6), 975.
[79] Wittbecker, E. L.; Morgan, P. W. J. Polym. Sci. Part A Polym. Chem. 1996, 34 (4), 521.
[80] Morgan, P. W.; Kwolek, S. L. J. Chem. Educ. 1959, 36 (4), 182.
[81] Morgan, P. W. In Condensation Polymers: By Interfacial and Solution Methods; Interscience: New York, 1965; pp 65-115.
[82] Morgan, P. W.; Kwolek, S. L. Macromolecules 1975, 8 (2), 104.
[83] Wang, L.; Wang, Y.; Ren, L. J. Appl. Polym. Sci. 2008, 109 (2), 1310.
[84] Vlachopoulos, J.; Strutt, D. Mater. Sci. Technol. 2003, 19 (9), 1161.
[85] Davidson, D.; Bernhard, S. A. J. Am. Chem. Soc. 1948, 70 (10), 3426.
[86] Smith, A. M. R.; Rzepa, H. S.; White, A. J. P.; Billen, D.; Hii, K. K. J. Org. Chem. 2010, 75(9), 3085.
[87] Botkin, J. H.; Forsyth, D. A.; Sardellaib, D. J. J. Am. Chem. Soc. 1986, 108 (11), 2797.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein are hereby incorporated by reference in their entirety for all purposes.

The invention claimed is:

1. A method of forming a poly(ester-amide) comprising the steps of:
    (a) disposing an aromatic aldehyde selected from vanillin, 4-hydroxybenzaldehyde and 4-hydroxy-3,5-dimethoxybenzaldehyde in a reaction vessel;
    (b) disposing a t-butyl malonate in the reaction vessel;
    (c) reacting the aromatic aldehyde with the t-butyl malonate in a Doebner modification of a Knoevenagel condensation reaction so as to generate an ester compound;
    (d) reacting the ester compound of (c) with a deprotonating agent in situ so as to generate a salt of the ester compound;
    (e) reacting the salt of the ester compound of (d) with a diacid chloride or bromide in a salt metathesis reaction so as to generate an ester of a monolignol dimer; and
    (f) converting the ester of a monolignol dimer of (e) into a carboxylic acid via a reaction with trifluoroacetic acid (TFA);
    a so that a dicarboxylic acid ester dimer is formed;
    converting the dicarboxylic acid ester dimer to a diacid chloride via a reaction with thionyl chloride;
    removing excess thionyl chloride under vacuum;
    dissolving the diacid chloride ester dimer in a halogenated organic solvent; and
    combining the halogenated organic solvent solution with an aqueous basic solution comprising a diamine in a condensation polymerization reaction so as to form a poly(ester-amide).

2. The method of claim 1, wherein the diamine is:

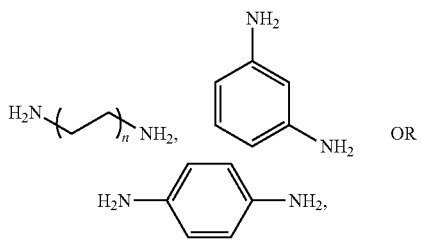

wherein n=1, 2, 3, 4 or 5.

3. The method of claim 1, wherein the poly(ester-amide) is formed via an interfacial polymerization reaction.

4. The method of claim 1, further comprising reacting the poly(ester-amide) in:
an atom-transfer radical-polymerization (ATRP) reaction; or
a reversible addition-fragment chain transfer (RAFT) reaction.

5. The method of claim 1, further comprising concentrating the poly(ester-amide) via a precipitation process.

6. The method of claim 5, further comprising:
dissolving the poly(ester-amide) precipitate in a solution comprising toluene combined with itaconic acid or Tulipalin A;
adding azobisisobutyronitrile (AIBN) to the solution;
degassing the solution;
heating the solution; and
purifying the resulting copolymer via precipitation.

7. The method of claim 1, wherein the poly(ester-amide) exhibits:
an onset of thermal decomposition ($T_{d5}$) between 220° C. and 260° C.; and/or
a glass transition temperature ($T_g$) between 64.7 and 138.2° C.

8. A method of forming a poly(ester-amide) comprising the steps of:
(a) reacting an aromatic aldehyde with a malonic ester in a Doebner modification of a Knoevenagel condensation reaction so as to generate an ester compound;
(b) reacting the ester compound of (a) with a deprotonating agent in situ so as to generate a salt of the ester compound;
(c) reacting the salt of the ester compound of (b) with a diacid chloride or bromide in a salt metathesis reaction so as to generate an ester of a monolignol dimer; and
(d) converting the ester of a monolignol dimer of (c) into a carboxylic acid via a reaction with trifluoroacetic acid (TFA);
so that a dicarboxylic acid ester dimer is formed;
converting the dicarboxylic acid ester dimer to a diacid chloride via a reaction with thionyl chloride;
removing excess thionyl chloride under vacuum;
dissolving the diacid chloride ester dimer in a halogenated organic solvent; and
combining the halogenated organic solvent solution with an aqueous basic solution comprising a diamine in a condensation polymerization reaction so as to form a poly(ester-amide).

* * * * *